United States Patent
Chang et al.

(10) Patent No.: US 11,400,189 B2
(45) Date of Patent: Aug. 2, 2022

(54) BREAST PUMP SYSTEM WITH CONTROLLER

(71) Applicant: EXPLORAMED NC7. INC., Mountain View, CA (US)

(72) Inventors: John Y Chang, Los Altos, CA (US); Joshua Makower, Los Altos Hills, CA (US); Brendan M Donohoe, Fairfax, CA (US); Michele Torosis, Los Altos, CA (US)

(73) Assignee: Willow Innovations, Inc., Mountain View, CA (US)

( * ) Notice: Subject to any disclaimer, the term of this patent is extended or adjusted under 35 U.S.C. 154(b) by 936 days.

(21) Appl. No.: 15/719,896

(22) Filed: Sep. 29, 2017

(65) Prior Publication Data
US 2018/0021490 A1    Jan. 25, 2018

Related U.S. Application Data

(63) Continuation of application No. 15/406,923, filed on Jan. 16, 2017, now Pat. No. 10,434,228, which is a
(Continued)

(51) Int. Cl.
*A61M 1/00* (2006.01)
*A61M 1/06* (2006.01)
(Continued)

(52) U.S. Cl.
CPC .............. *A61M 1/06* (2013.01); *A61M 1/064* (2014.02); *A61M 1/74* (2021.05); *A61M 1/84* (2021.05);
(Continued)

(58) Field of Classification Search
CPC ........ A61M 1/06; A61M 1/062; A61M 1/064; A61M 1/066; A61M 1/068; A61M 1/007;
(Continued)

(56) References Cited

U.S. PATENT DOCUMENTS

| 1,197,011 A | 9/1916 | Cilino |
| 4,263,912 A | 4/1981 | Adams |

(Continued)

FOREIGN PATENT DOCUMENTS

| CN | 2628060 Y | 7/2004 |
| CN | 201692384 | 1/2011 |

(Continued)

OTHER PUBLICATIONS

Chiu et a. , Development of a plezoelectric polyvinylldene fluoride (PVDF) polymer based sensor patch for simultaneous heartbeat and respiration monitoring, Sensors and Actuators A: Physical, vol. 189, Jan. 15, 2013, pp. 328-334.
(Continued)

*Primary Examiner* — William R Carpenter
*Assistant Examiner* — William R Frehe

(57) ABSTRACT

Systems and methods for pumping milk from a breast responsive to a controller, wherein the milk is expressed from the breast under suction and milk is expulsed from the pumping mechanism to a collection container under positive pressure.

18 Claims, 25 Drawing Sheets

Related U.S. Application Data continuation of application No. PCT/US2015/041285, filed on Jul. 21, 2015.

(60) Provisional application No. 62/138,650, filed on Mar. 26, 2015, provisional application No. 62/027,685, filed on Jul. 22, 2014.

(51) Int. Cl.
*A61J 13/00* (2006.01)
*A61B 18/00* (2006.01)

(52) U.S. Cl.
CPC ..... *A61B 2018/00333* (2013.01); *A61J 13/00* (2013.01); *A61M 2205/3331* (2013.01); *A61M 2210/1007* (2013.01)

(58) Field of Classification Search
CPC ........ A61M 2210/1007; A61M 1/0031; A61M 1/0037; A61B 2018/00333; A61J 13/00; F04B 43/08; F04B 43/082; F04B 43/1223
See application file for complete search history.

(56) References Cited

U.S. PATENT DOCUMENTS

| | | | |
|---|---|---|---|
| 4,311,141 A | 1/1982 | Diamond | |
| 4,768,547 A | 9/1988 | Danby et al. | |
| 4,821,580 A * | 4/1989 | Jorrilsma | G01F 1/34 702/47 |
| 5,542,921 A | 8/1996 | Meyers et al. | |
| 5,634,468 A | 6/1997 | Platt et al. | |
| 5,658,133 A | 8/1997 | Anderson et al. | |
| 5,810,772 A | 9/1998 | Niederberger | |
| 5,827,191 A | 10/1998 | Rosenfeld | |
| 6,273,868 B1 | 8/2001 | Nordvik | |
| 6,287,252 B1 | 9/2001 | Lugo | |
| 6,328,082 B1 | 12/2001 | Lafond | |
| D459,233 S | 6/2002 | Young | |
| 6,440,100 B1 | 8/2002 | Prentiss | |
| 6,547,756 B1 * | 4/2003 | Greter | A61M 1/06 604/74 |
| 6,579,258 B1 | 6/2003 | Atkin et al. | |
| 6,712,785 B2 | 3/2004 | Morton et al. | |
| 6,840,918 B1 | 1/2005 | Britto et al. | |
| 7,201,735 B2 | 4/2007 | Atkin et al. | |
| 7,223,255 B2 | 5/2007 | Myers et al. | |
| 7,621,797 B1 | 11/2009 | Hershkovich | |
| 7,824,363 B2 | 11/2010 | Myers | |
| 7,972,297 B2 | 7/2011 | Bryan et al. | |
| 7,988,661 B2 | 8/2011 | Silver et al. | |
| 8,057,425 B1 | 11/2011 | Myers et al. | |
| 8,070,715 B2 | 12/2011 | Quackenbush et al. | |
| 8,070,716 B2 | 12/2011 | Sutrina et al. | |
| 8,262,606 B2 | 9/2012 | Greter et al. | |
| 8,282,596 B2 | 10/2012 | Greter et al. | |
| 8,353,865 B2 | 1/2013 | Thilwind et al. | |
| 8,357,116 B2 | 1/2013 | Simdon | |
| 8,376,986 B2 | 2/2013 | Van Schijndel et al. | |
| 8,671,701 B2 | 3/2014 | McKendry | |
| 8,684,961 B2 | 4/2014 | Gottenbos et al. | |
| 8,801,495 B1 | 8/2014 | Guidon | |
| 9,050,404 B2 | 6/2015 | Silver et al. | |
| 9,162,016 B2 | 10/2015 | Geddes | |
| 9,173,587 B2 | 11/2015 | Van Schijndel et al. | |
| 9,199,017 B2 | 12/2015 | Greter | |
| 9,278,167 B2 | 3/2016 | Aalders et al. | |
| 2003/0191433 A1 | 10/2003 | Prentiss | |
| 2004/0024351 A1 | 2/2004 | Greter et al. | |
| 2004/0101414 A1 | 5/2004 | Gharib et al. | |
| 2004/0127845 A1 | 7/2004 | Renz et al. | |
| 2005/0059928 A1 | 3/2005 | Larsson | |
| 2005/0131332 A1 | 6/2005 | Kelly et al. | |
| 2005/0234370 A1 | 10/2005 | Beal et al. | |
| 2006/0106334 A1 | 5/2006 | Jordan et al. | |
| 2008/0009815 A1 * | 1/2008 | Grabenkort | A61M 1/74 604/74 |
| 2008/0045888 A1 | 2/2008 | Edwards et al. | |
| 2008/0177224 A1 * | 7/2008 | Kelly | A61M 1/742 604/74 |
| 2008/0243059 A1 | 10/2008 | Yamashita et al. | |
| 2009/0024080 A1 | 1/2009 | Rohrig | |
| 2010/0106082 A1 * | 4/2010 | Zhou | A61M 5/14232 604/67 |
| 2010/0217148 A1 | 8/2010 | Binder | |
| 2011/0071466 A1 * | 3/2011 | Silver | A61M 1/82 604/74 |
| 2011/0196291 A1 | 8/2011 | Vischer et al. | |
| 2011/0245763 A1 | 10/2011 | Myers | |
| 2011/0270162 A1 | 11/2011 | Guo | |
| 2012/0101575 A1 | 4/2012 | Horne et al. | |
| 2012/0277636 A1 | 11/2012 | Blondheim et al. | |
| 2012/0277728 A1 | 11/2012 | Weber et al. | |
| 2013/0023821 A1 * | 1/2013 | Khalil | A61M 1/064 604/74 |
| 2013/0123688 A1 | 5/2013 | Bosman et al. | |
| 2013/0131588 A1 | 5/2013 | Silver et al. | |
| 2013/0177455 A1 | 7/2013 | Kamen et al. | |
| 2014/0031744 A1 * | 1/2014 | Chen | A61M 1/066 604/74 |
| 2014/0066734 A1 | 3/2014 | Zdeblick | |
| 2014/0378895 A1 | 12/2014 | Barack | |
| 2014/0378946 A1 | 12/2014 | Thompson et al. | |
| 2015/0065994 A1 | 3/2015 | Fridman et al. | |
| 2015/0100016 A1 | 4/2015 | Liao | |
| 2015/0148709 A1 | 5/2015 | Mardiks et al. | |
| 2015/0196247 A1 * | 7/2015 | Lau | A61B 5/14542 600/301 |
| 2015/0292500 A1 * | 10/2015 | Girard | F04B 49/065 417/53 |
| 2016/0015876 A1 | 1/2016 | Tattersfield et al. | |
| 2016/0058928 A1 * | 3/2016 | Nowroozi | A61M 1/066 604/74 |
| 2016/0256618 A1 | 9/2016 | Embleton | |
| 2017/0143879 A1 * | 5/2017 | Okaguchi | A61M 1/064 |
| 2018/0296741 A1 * | 10/2018 | Hill | A61M 1/062 |
| 2020/0078503 A1 * | 3/2020 | Bartlett | A61M 1/062 |
| 2020/0375839 A1 * | 12/2020 | Kim | A61M 1/80 |
| 2021/0393861 A1 * | 12/2021 | Mathew | A61M 1/06 |

FOREIGN PATENT DOCUMENTS

| | | |
|---|---|---|
| EP | 2456482 B1 | 11/2016 |
| EP | 3151876 B1 | 11/2017 |
| GB | 2342446 A | 4/2000 |
| JP | 2005279044 | 10/2005 |
| RU | 2012 107356 | 5/2012 |
| WO | WO1996022116 | 7/1996 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO2012037848 A1 | 3/2012 |
| WO | WO 2013076055 | 5/2013 |
| WO | WO2013088310 | 6/2013 |
| WO | WO 2013/187763 | 12/2013 |
| WO | WO2013184004 | 12/2013 |
| WO | WO2015120321 | 8/2015 |

OTHER PUBLICATIONS

Double Electric Breast Pump/Dr. Brown's, http://www.drbrownsbaby.com/breastfeeding-product/breast-pumps/double-electric, May 15, 2014.

* cited by examiner

Useful Tubing Actuation Range
Tubing Deflection: vs. Vacuum / vs. Loading

| Run Time | minutes | hours | sessions |
|---|---|---|---|
| Single Session | 15 | 0.250 | 1 |
| Full Day | 60 | 1.000 | 4 |

| | Voltage (V) | MAX Current (A) | Average Current (mA) | Required capacity-single session (mAh) | Required Capacity-full day (mAh) |
|---|---|---|---|---|---|
| Alkaline - C(x4) | 6 | 0.83 | 440 | 110 | 440 |
| | 330 | 334 | 332 | 336 | 338 |

| Tubing Dimension | | Option 1 | Option 2 | Option 3 | Option 4 |
|---|---|---|---|---|---|
| | ID (in) | 0.375 | 0.313 | 0.250 | 0.375 |
| | OD (in) | 0.563 | 0.439 | 0.376 | 0.563 |
| Tubing Dead Volume(cc) | | 2.36 | 1.56 | 0.63 | 10.7 |
| Length of compression member 38 (mm) | | 23 | 35 | 40 | 62 |
| Active Pumping Volume(cc)-A | | 1.64 | 1.73 | 1.30 | 4.8 |
| Total Tubing Volume (cc)-B | | 4.00 | 3.29 | 1.93 | 15.5 |
| Nipple Dead Volume(cc)-B-C | | 1.80 | 1.80 | 1.80 | 14.1 |
| Pump/ Total Volume Ratio: A/(B+C) | | 28.3% | 34.0% | 34.9% | 16.2% |

FIG. 19

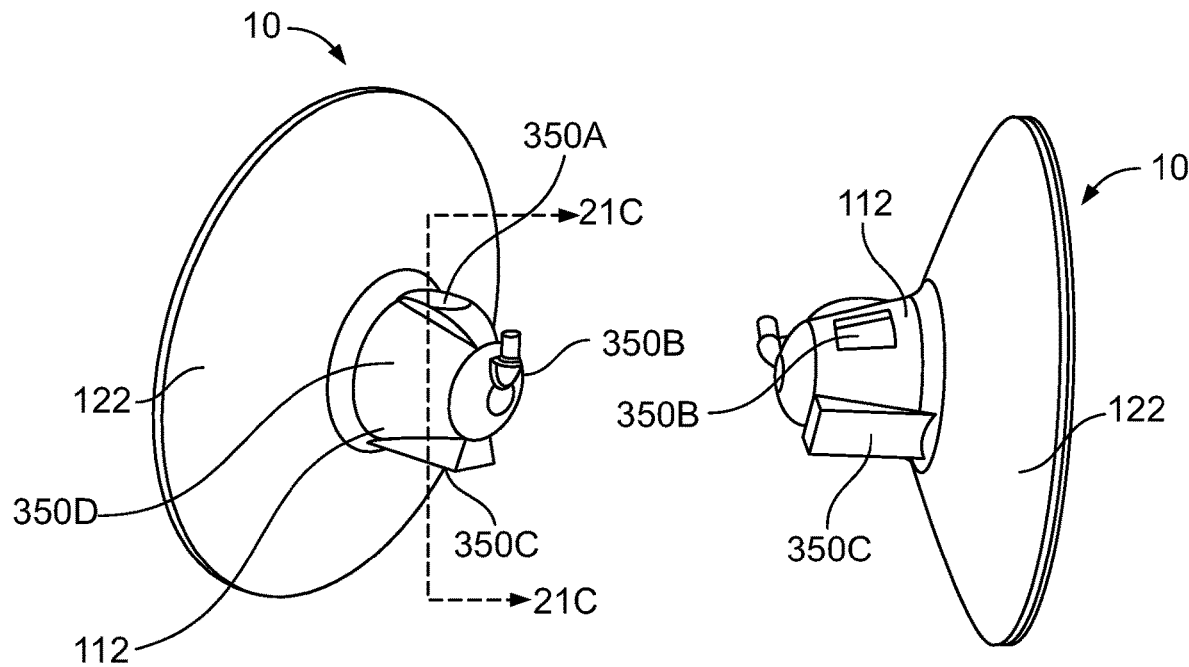
FIG. 21A  FIG. 21B
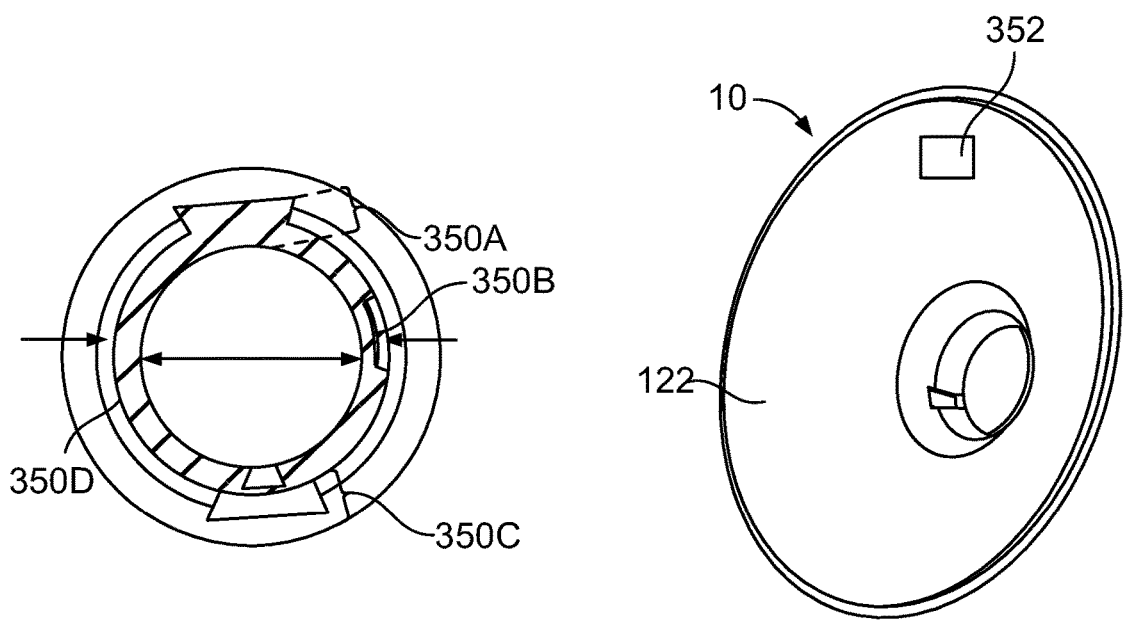
FIG. 21C  FIG. 22

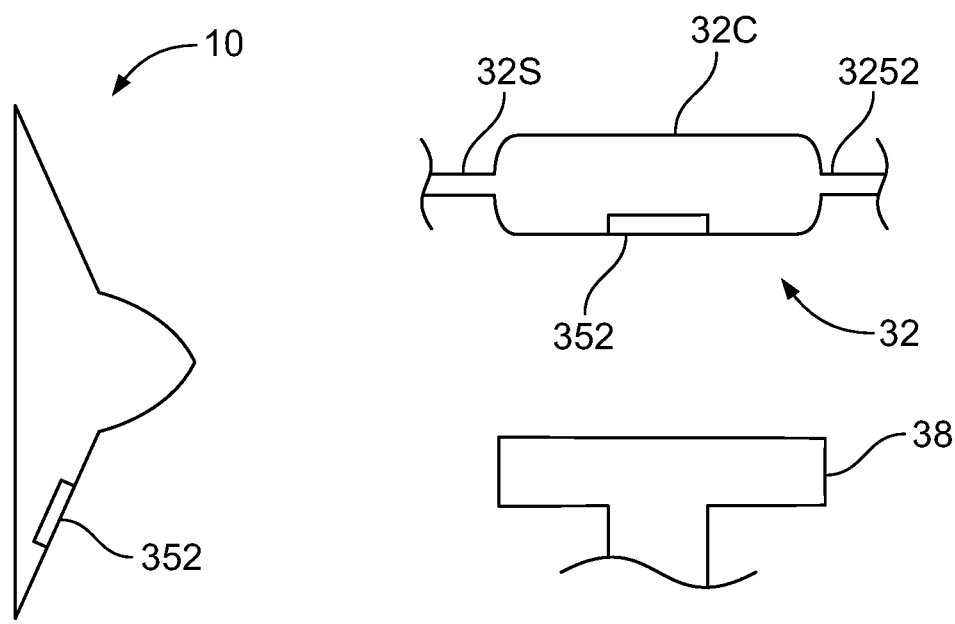
FIG. 27
FIG. 26
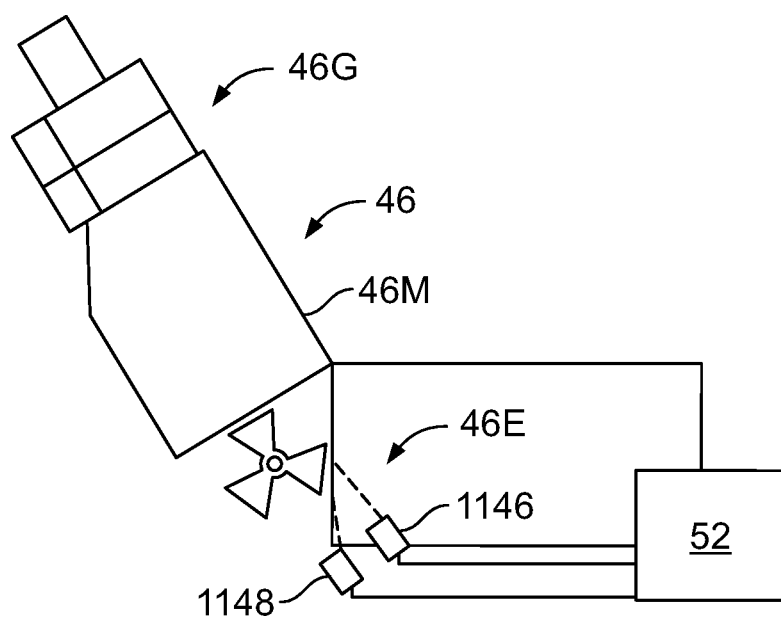
FIG. 28

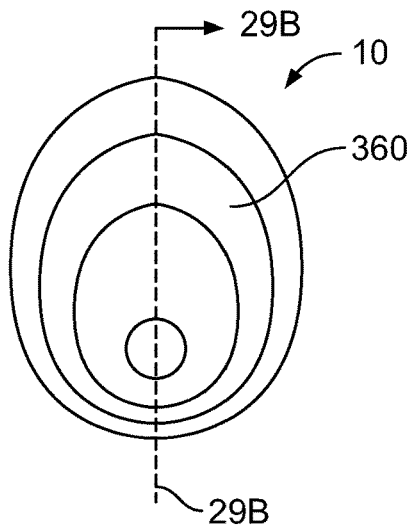
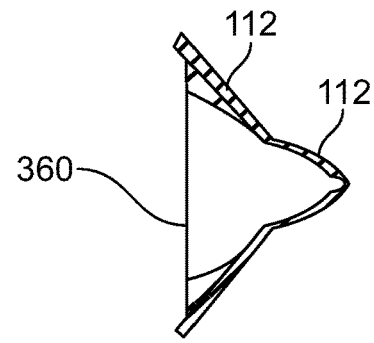
FIG. 29A
FIG. 29B
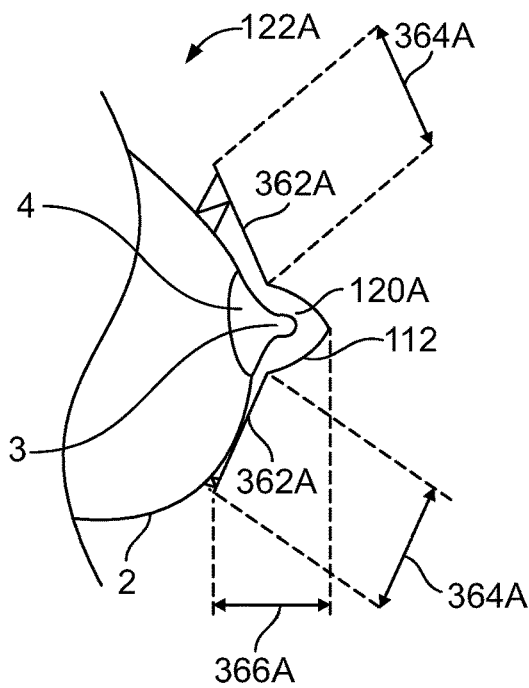
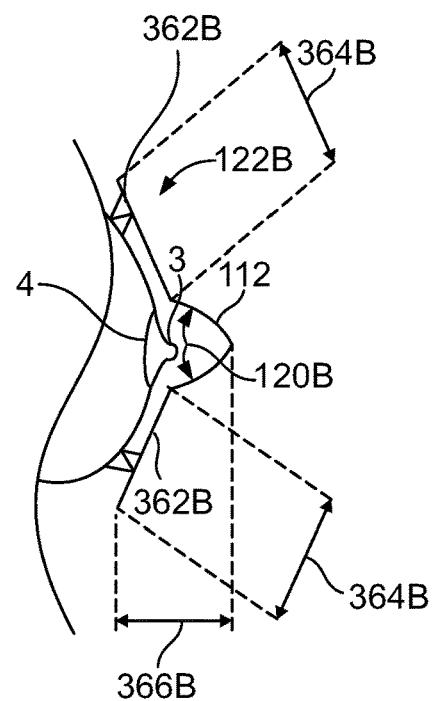
FIG. 30A
FIG. 30B
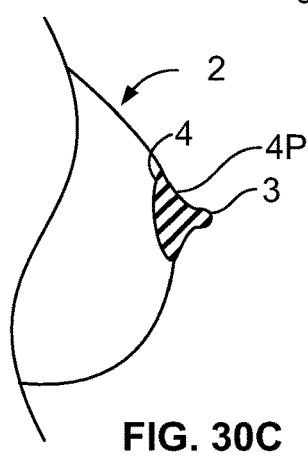
FIG. 30C

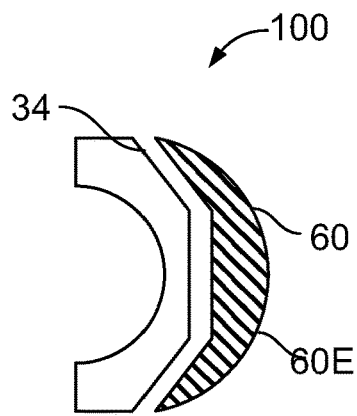
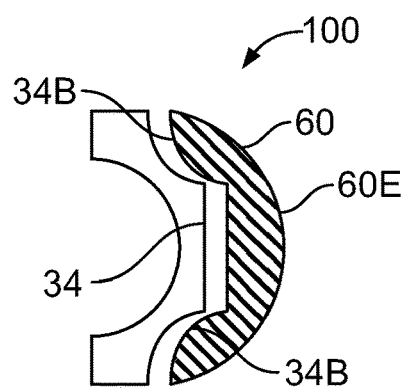
FIG. 31A  FIG. 31B
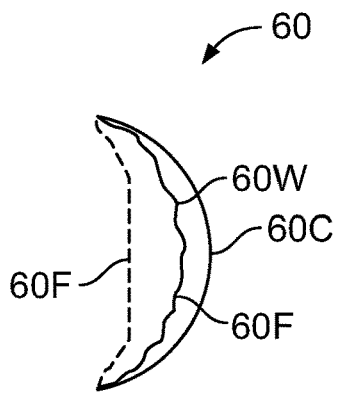
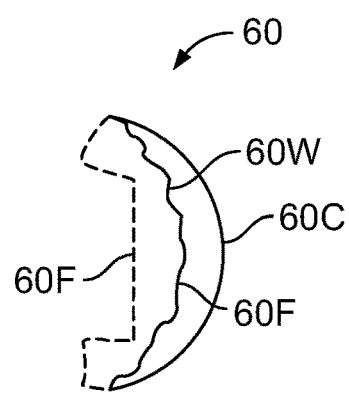
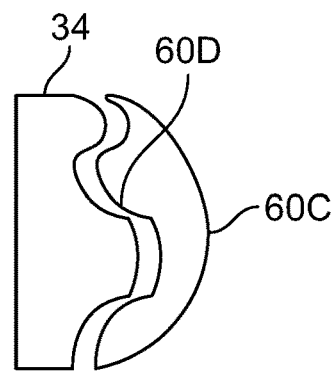
FIG. 32A  FIG. 32B  FIG. 32C
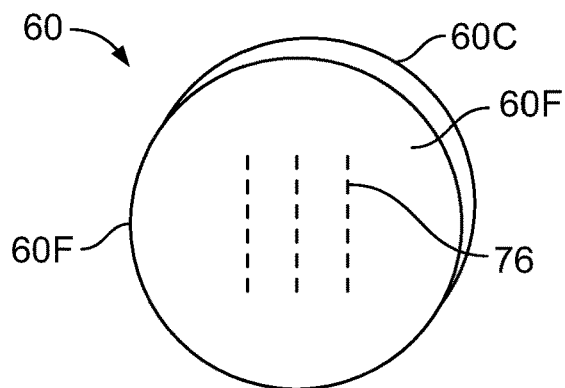
FIG. 33

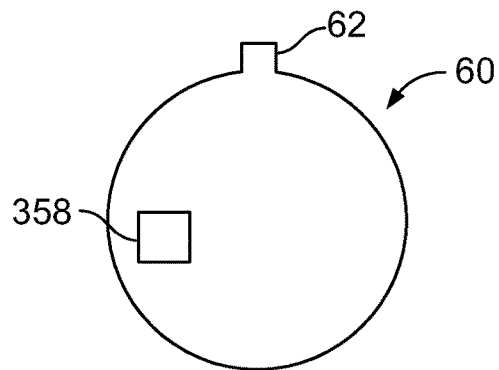
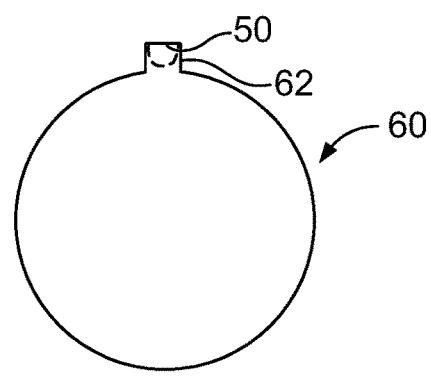
FIG. 34     FIG. 35
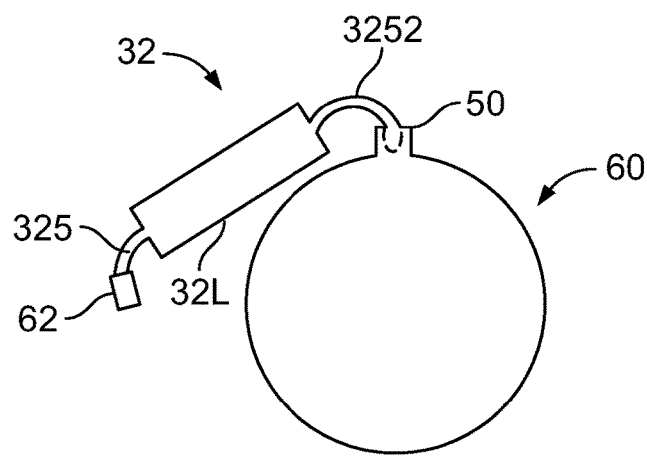
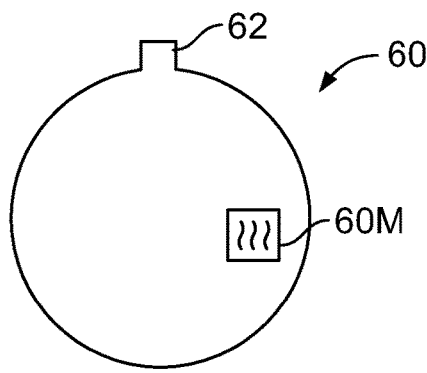
FIG. 36     FIG. 37

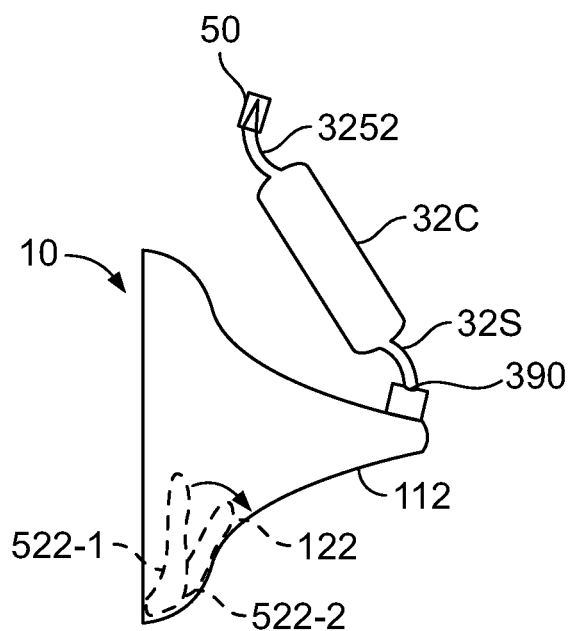
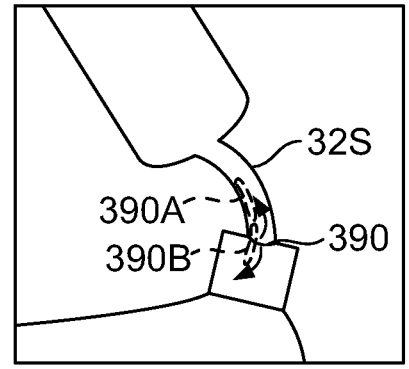
FIG. 39A            FIG. 39B
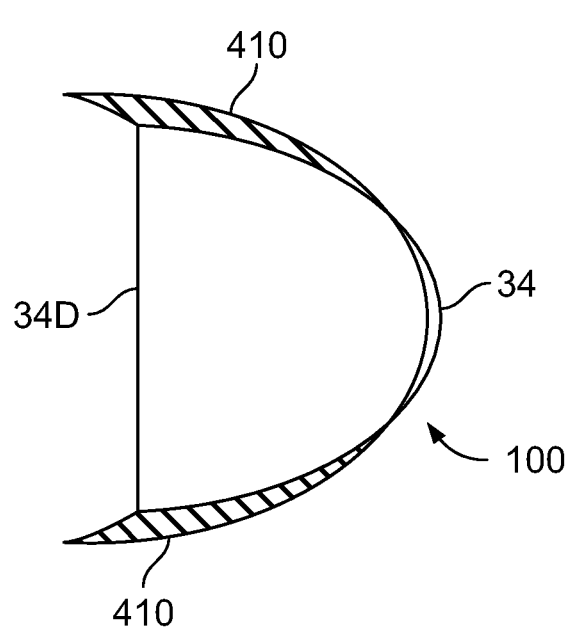
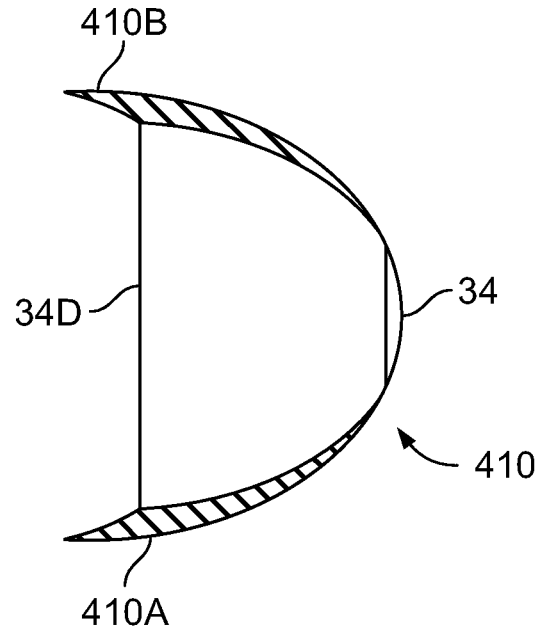
FIG. 40A            FIG. 40B

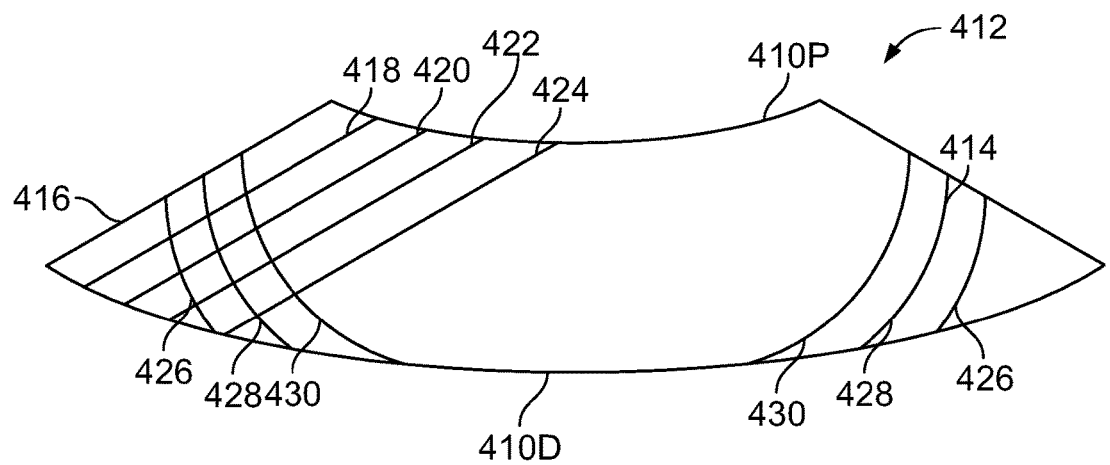
FIG. 44
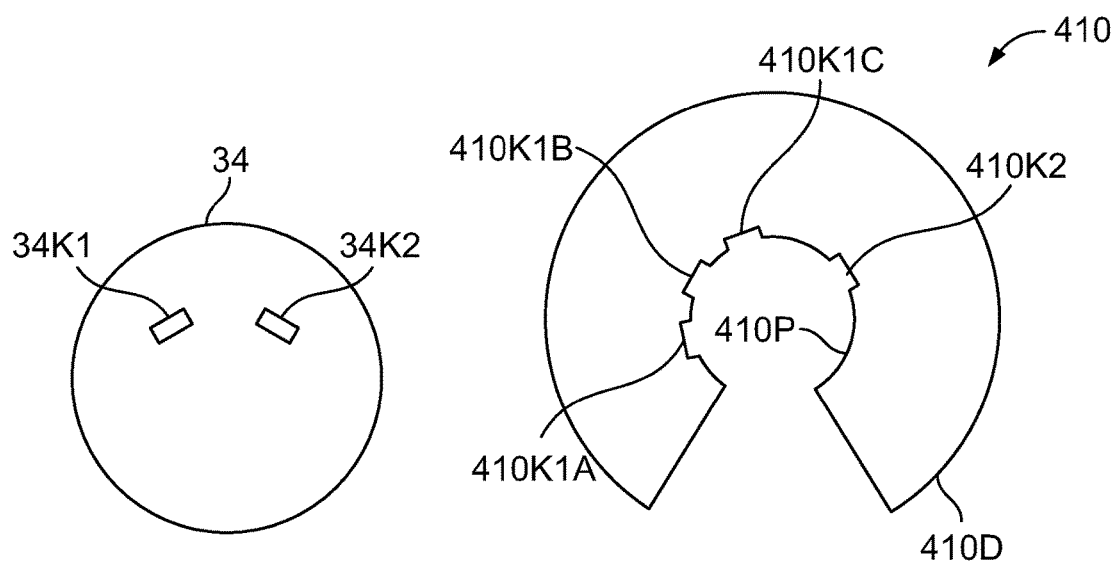
FIG. 45A  FIG. 45B

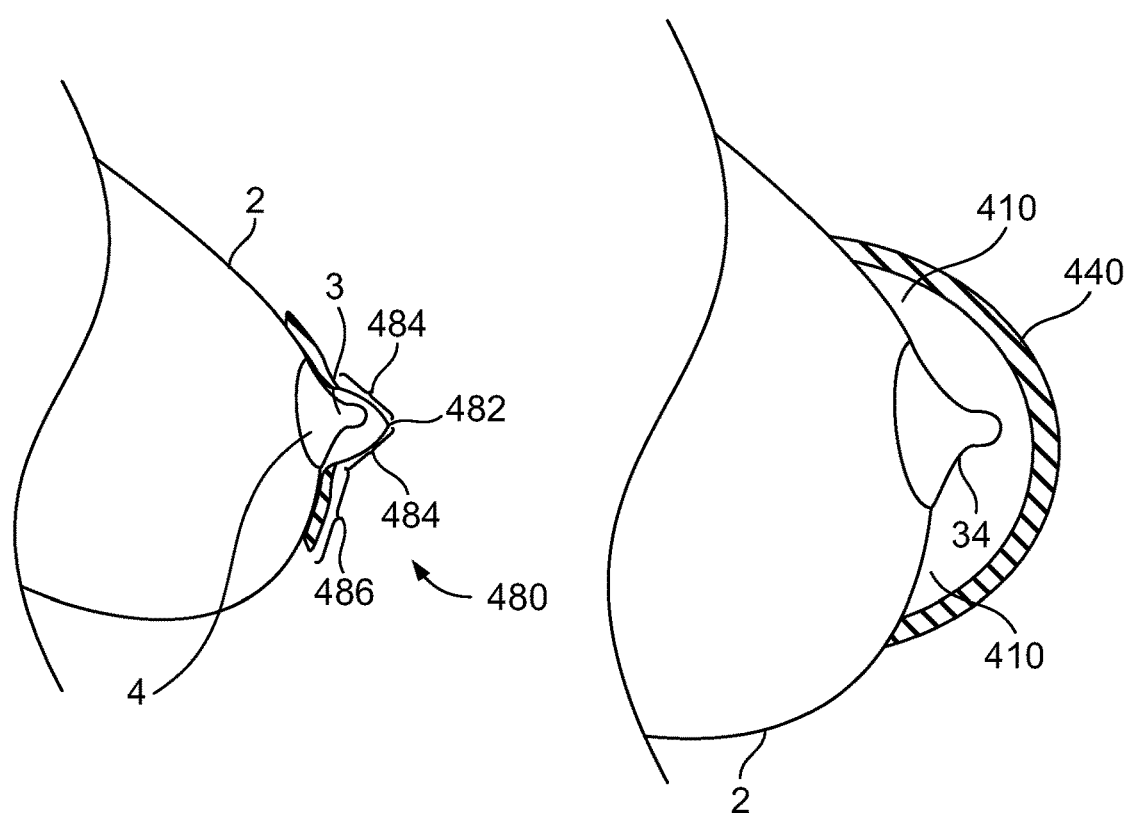
FIG. 48
FIG. 46B
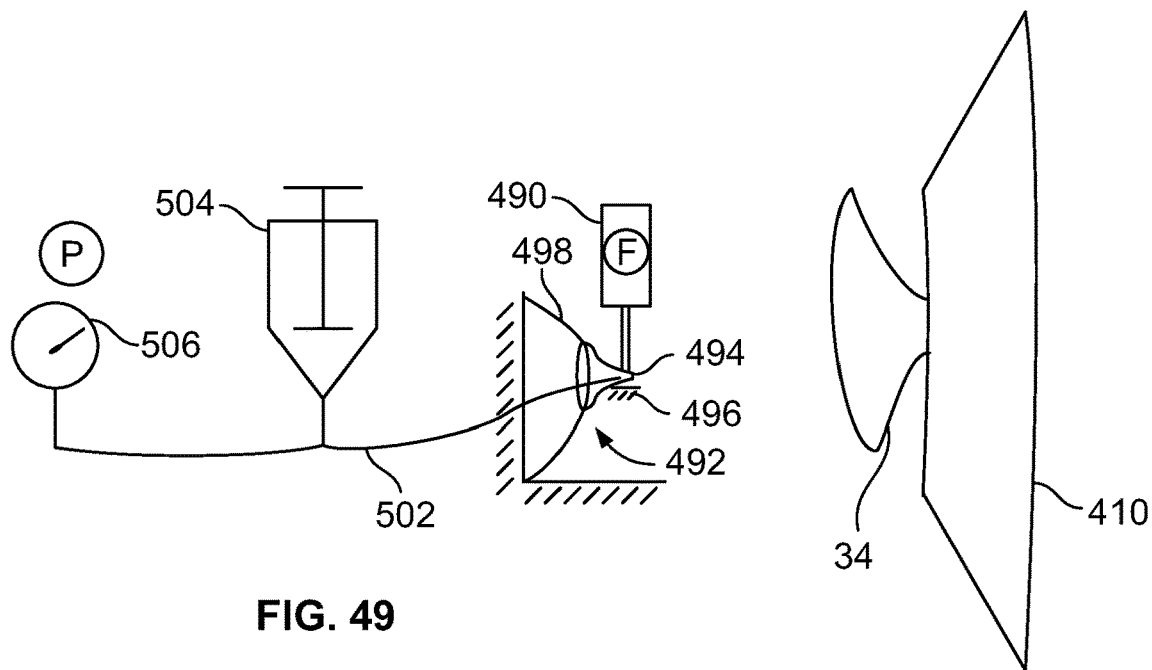
FIG. 49
FIG. 46A

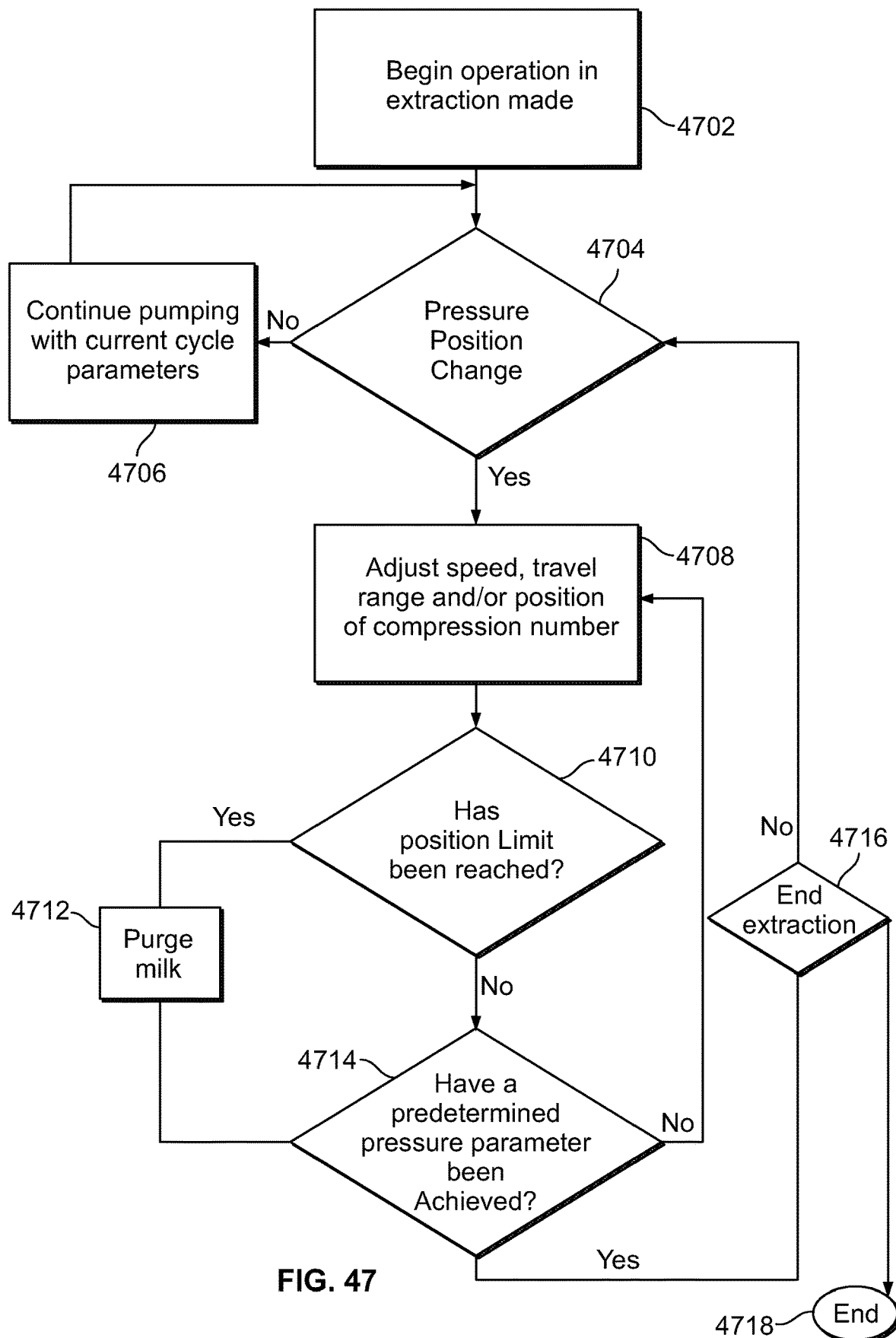

BREAST PUMP SYSTEM WITH CONTROLLER

FIELD OF THE DISCLOSURE

The present disclosure generally relates to portable, energy efficient breast pump systems and methods for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, most are awkward and cumbersome, requiring many parts and assemblies and being difficult to transport. Hand pump varieties that are manually driven are onerous to use and can be painful to use. Some powered breast pumps require an AC power source to plug into during use. Some systems are battery driven, but draw down the battery power fairly rapidly as the motorized pump continuously operates to maintain suction during the milk extraction process. Many of the breast pumps available are clearly visible to an observer when the mother is using it, and many also expose the breast of the mother during use.

There is a continuing need for a small, portable, self-powered, energy efficient, wearable breast pump system that is easy to use and is discrete by not exposing the breast of the user and being invisible or nearly unnoticeable when worn.

To ensure that the nursing baby is receiving adequate nutrition, it is useful to monitor the baby's intake. It would be desirable to provide a breast pump system that easily and accurately monitors the volume of milk pumped by the system, to make it convenient for the nursing mother to know how much milk has been extracted by breast pumping. It would also be desirable to track milk volume pumped per session, so that the volume of milk contained in any particular milk collection container can be readily known.

Many existing breast pump systems can cause considerable discomfort to the user over time. One cause of such discomfort is chafing of the nipple against the nipple flange/housing as the nipple stretches and contracts during the pumping session. There is a continuing need for a breast pump system that is more comfortable to the user, even over repeated pumping sessions.

SUMMARY OF THE DISCLOSURE

Briefly and in general terms, the present disclosure is directed toward breast pump systems or methods. The system includes breast contacting structure and a storage container, and structure that delivers milk from a breast to the storage container. The method involves pumping milk from a breast and delivering the pumped milk into the storage container.

According to one aspect of the present disclosure, a system for pumping milk from a breast includes one or more of: a skin contact member configured to form a seal with the breast; a conduit in fluid communication with and connected to the skin contact member; a driving mechanism configured to establish a vacuum profile within the conduit; an external shell; and a milk collection container; wherein the external shell comprises a compartment facing a distal end of the external shell, the external shell further comprising a proximal end surface facing away from the proximal end; wherein the skin contact member, the conduit and the driving mechanism are received in the compartment of the external shell; wherein the milk collection container is positionable over the distal end surface of the shell; and wherein the system is shaped and configured to be contoured to the breast of a user.

In various of the disclosed embodiments, the system defines a natural breast profile. The natural breast profile is contemplated to fit comfortably and conveniently into a bra of a user and to present a natural look. As such, the profile is characterized by having a non-circular base. Moreover, like natural breasts, the profile of the device or system is contemplated to define one or more asymmetric curves and off-center inertial centers.

In at least one embodiment, the skin contact member, the conduit, the driving mechanism, the external shell and the milk collection container are all contained within a cup of a brassiere.

In at least one embodiment, the system is battery powered, the system comprising a battery, wherein the battery is received in the compartment of the external shell.

In at least one embodiment, the proximal surface of the external shell is shaped and configured to be contoured to the breast of a user and to thus provide a more natural appearance when under clothing worn by the user.

In at least one embodiment, the proximal surface of the external shell comprises a polygonal, flat, irregular or discontinuously curved shape dissimilar to the curvature of the breast; and the milk collection container is configured to interface with the proximal surface and to be shaped and configured to be contoured to the breast of a user and to thus provide a more natural appearance when under the clothing of the user.

In at least one embodiment, the proximal surface comprises flat surfaces that form an angular external surface.

In at least one embodiment, the proximal surface comprises a flat central portion and convex portions extending radially from the flat central portion.

In at least one embodiment, the milk collection container is configured and dimensioned to have variable volume when filled, so as to conform to the proximal surface of the external shell as the milk collection container is being filled with milk, while providing a convex shape externally, so as to mimic a natural shape of the breast.

In at least one embodiment, the milk collection container is pre-shaped to follow contours of the proximal surface of the external shell and to providing a convex shape externally, so as to mimic a natural shape of the breast.

In at least one embodiment, the milk collection container comprises a rigid distal surface that mates with contours of the proximal surface of the external shell, and a flexible proximal surface that moves as milk enters the milk collection container, to provide a convex shape that mimics a natural shape of the breast.

In at least one embodiment, the milk collection container comprises a flexible distal surface that changes shape to mate with contours of the proximal surface of the external shell as milk enters the milk collection container, the milk collection container further comprising a rigid proximal surface that provides a convex shape that mimics a natural shape of the breast.

In at least one embodiment, the milk collection container comprises a rigid distal surface pre-shaped to mate with contours of the proximal surface of the external shell as milk enters the milk collection container.

In at least one embodiment, the milk collection container comprises at least one structural element configured to restrict an amount of expansion of the milk collection container or provide shape to the milk collection container even when empty.

In at least one embodiment, the at least one structural element is selected from the group consisting of baffles, heat seals, struts and restrictions.

In at least one embodiment, the milk collection container comprises a unique identifier configured to be read by a computer processor and that uniquely distinguished the milk collection container from all other milk collection containers.

In at least one embodiment, the unique identifier comprises a sensor.

In at least one embodiment, the sensor comprises a passive sensor.

In at least one embodiment, the system further includes a controller positioned within the external shell and configured to control operations of the driving mechanism.

In at least one embodiment, the milk collection container comprises a unique identifier configured to be read by at least one of the controller and an external computer processor and that uniquely distinguished the milk collection container from all other milk collection containers.

In at least one embodiment, the unique identifier comprises a sensor.

In at least one embodiment, the sensor comprises a passive sensor.

In at least one embodiment, the sensor is selected from the group consisting of: RFID device, NFC device, Wi-Fi device, BLUETOOTH device and BLUETOOTH Low Energy (BTLE) device.

In at least one embodiment, the sensor is selected from the group consisting of: RFID devices and NFC devices.

In at least one embodiment, the milk collection container comprises a one-way valve that permits milk inflow into the milk collection container but prevents milk backflow from the milk collection container to the conduit.

In at least one embodiment, the conduit is integral with the milk collection container.

In at least one embodiment, the system further includes a contour element; wherein the contour element extends distally from a distal perimeter of the external shell and proximally extends over a distal portion of the external shell to provide a contoured extension of the external shell that provides a visually more appealing appearance that more closely mimics a natural appearance of the breast supported by a bra.

In at least one embodiment, the contour element tapers distally to form a smooth transition with the breast when the system is mounted on the breast.

In at least one embodiment, the contour element is removably attached to the external shell using at least one of snaps, hook-and-loop type fasteners, buttons, magnets adhesive, or friction fit.

In at least one embodiment, the contour element comprises a lateral portion that extends distally from the distal perimeter by a first length, and a medial portion that extends distally from the distal perimeter by a second length, wherein the first length is greater than the second length.

In at least one embodiment, the contour element is formed of lightweight material comprising at least one of foam, plastic or fabric.

In at least one embodiment, the contour element is formed of a single thin layer of plastic or fabric.

In at least one embodiment, the external shell comprises a key and the contour element comprises a mating key; wherein the mating key mates with the key when the contour element is mounted on the external shell and ensures that the contour element is positioned relative to the external shell consistently so that orientation of the contour element relative to the external shell upon successive mountings does not vary rotationally, superiorly, inferiorly, laterally or medially.

In at least one embodiment, the contour element is adjustable to accommodate different breast sizes.

In at least one embodiment, the contour element comprises a first edge and a second edge, wherein the first edge overlaps the second edge and can be adjusted to reduce, increase or maintain a circumference of a distal perimeter of the contour element.

In at least one embodiment, the overlap of the first edge relative to the second edge can be adjusted to reduce, increase or maintain a circumference of a proximal perimeter of the contour element.

In at least one embodiment, the contour element comprises a material that facilitates cutting a portion of a distal perimeter thereof for tailoring a fit of the contour element to the breast.

In at least one embodiment, the contour element comprises predetermined markings to assist in adjusting the contour element to various predetermined sizes.

In at least one embodiment, the external shell comprises at least one key and the contour element comprises multiple mating keys that mate with each the at least one key, respectively, to allow adjustment of a size of the contour element.

In at least one embodiment, the contour element is made of a resilient material that conforms to a shape of an object that the contour element is compressed against.

In at least one embodiment, the contour element is substantially flat-shaped in an unbiased configuration.

In at least one embodiment, the contour element is attachable to a proximal end portion of the external shell.

In at least one embodiment, the contour element, when supported by a bra, contours to the external shell and the bra.

In at least one embodiment, the system further includes a valve in the conduit adjacent the skin contact member, wherein the valve is configured to open in a first direction when vacuum is generated in the conduit, to close when positive pressure up to a predetermined positive pressure is applied to the valve, and to open in a second direction when positive pressure exceeding the predetermined positive pressure is applied to the valve.

According to another aspect of the present disclosure, a system for pumping milk from a breast includes one or more of: an external shell including a compartment facing a distal end of the external shell, the external shell further comprising a proximal end surface facing away from the proximal end; the external shell carrying a self-contained power source and a pump mechanism; a skin contact member supported by the external shell; an outlet for expelling breast milk received from the breast interfaced with the skin contact member; and a milk collection container in fluid communication with the outlet and positioned against the distal end surface of the external shell; wherein the system is shaped and configured to be contoured to the breast of a user.

In at least one embodiment, the system is contained within a cup of a brassiere.

In at least one embodiment, the skin contact member, the external shell and the milk collection container are sized and configured to be supported between the breast and a breast cup of a bra while the system is actively pumping milk from the breast and expelling the milk through the outlet and into the milk collection container.

According to another aspect of the present disclosure, a milk collection container for use with a breast pump system includes one or more of: a preformed surface shaped to mimic the natural appearance of a breast; and a flexible surface opposing the preformed convex surface, the flexible surface being configured to expand as milk enters the milk collection container.

In at least one embodiment, the milk collection container is mounted to an external surface of an external shell of a milk pump, wherein upon milk entering the milk collection container, the flexible surface moves outwardly and conforms to a conformation of the external shell.

In at least one embodiment, the milk collection container comprises at least one structural element configured to restrict an amount of expansion of the milk collection container or provide shape to the milk collection container even when empty.

In at least one embodiment, the at least one structural element is selected from the group consisting of baffles, heat seals, struts and restrictions.

According to another aspect of the present disclosure, a system for pumping milk from a breast includes one or more of: a skin contact member configured to form a seal with the breast; a conduit in fluid communication with and connected to the skin contact member; a driving mechanism configured to establish a vacuum profile within the conduit by cyclically compressing and allowing decompression of a portion of the conduit; and an external shell containing the conduit and the driving mechanism and supporting the skin contact member.

In at least one embodiment, the system further includes a milk collection container, wherein the milk collection container is in fluid communication with the conduit.

In at least one embodiment, the milk collection container is positionable over the distal end surface of the shell; and the system is shaped and configured to be contoured to the breast of a user.

In at least one embodiment, the skin contact member includes: a breast contact portion configured and dimensioned to fit over a form a seal with a portion of the breast; and a nipple receiving portion extending from the breast contact portion.

In at least one embodiment, the nipple receiving portion comprises a non-tapering portion attached to the breast contact portion, and a tapering portion extending from the non-tapering portion, the tapering portion configured and dimensioned to receive the nipple of the breast.

In at least one embodiment, the non-tapering portion is cylindrical and the tapering portion is conical.

In at least one embodiment, the non-tapering portion is ovular or elliptical in cross section.

In at least one embodiment, the tapering portion is ovular or elliptical in cross section.

In at least one embodiment, both the non-tapering and the tapering portions are ovular or elliptical in cross section.

In at least one embodiment, the breast contact portion comprises a first central longitudinal axis and the nipple receiving portion comprises a second central longitudinal axis; and the first and second central longitudinal axes are collinear.

In at least one embodiment, the breast contact portion comprises a first central longitudinal axis and the nipple receiving portion comprises a second central longitudinal axis; and the first and second central longitudinal axes are parallel.

In at least one embodiment, the breast contact portion comprises a first central longitudinal axis and the nipple receiving portion comprises a second central longitudinal axis; and the first and second central longitudinal axes intersect.

In at least one embodiment, a top part of the nipple receiving portion is configured to contact an upper surface of the nipple and a bottom part of the nipple receiving portion is configured to contact a lower surface of the nipple; wherein the top part is formed a material having a first hardness and the bottom part is formed of a material having a second hardness; and wherein the first hardness is greater than the second hardness.

In at least one embodiment, the breast contact portion comprises at least one region on an inner surface thereof, the at least one region configured to contact the breast and provide friction thereagainst that is greater than friction provided by a remainder of the inner surface of the breast contact portion.

In at least one embodiment, the system further includes a resilient flap extending radially inwardly from a portion of the breast contact member; wherein when the breast is inserted into the breast contact member, the breast folds down the flap against an inner wall of the breast contact member; and wherein when the breast is removed from the breast contact member, the flap resiliently returns to an unbiased position and extends radially inwardly, thereby retaining milk within the breast contact member that would otherwise have spilled out of the breast contact member.

In at least one embodiment, the flap comprises a tacky or roughened surface configured to increase friction against the breast when contacting the breast.

In at least one embodiment, the system further includes a sensor mounted in or on the skin contact member or the conduit; and a controller configured to control operation of the driving mechanism and to receive signals from the sensor.

In at least one embodiment, the system further includes a first sensor mounted in or on the skin contact member or the conduit, wherein a thickness of the skin contact member or conduit at a location of mounting the first sensor comprises a first thickness; and a second sensor mounted in or on the skin contact member or the conduit, wherein a thickness of the skin contact member or conduit at a location of mounting the second sensor comprises a second thickness; wherein the second thickness is greater than the first thickness.

In at least one embodiment, the system further includes one or more of: a controller configured to control operation of the driving mechanism; and a switch in electrical communication with the controller, the switch extending into the skin contact member or the conduit at a distance from an inner wall of the skin contact member or the conduit predetermined as a distance by which the inner wall deflects when a predetermined vacuum pressure has been attained; wherein, upon attaining the predetermined vacuum pressure, the switch is activated by contact with the inner wall and sends a signal to the controller.

In at least one embodiment, the switch extends into the nipple receiving portion of the skin contact member.

According to another aspect of the present disclosure, a method of operating a system for pumping milk includes one or more of: providing the system comprising a skin contact member configured to form a seal with the breast, a conduit in fluid communication with and connected to the skin contact member; a driving mechanism including a compression member configured to compress and allow decompression of the conduit in response to inward and outward movements of the compression member, a sensor, and a controller configured to control operation of the driving mechanism; sealing the skin contact member to the breast; operating the driving mechanism to generate predetermined pressure cycles within the conduit; monitoring by the controller of at least one of position and speed of movement of the compression member relative to the conduit; measuring or calculating pressure within the conduit; maintaining or modifying motion of the compression member as needed, based upon feedback from the calculated pressure and at least one of position and speed of movement of the compression member, to ensure that the predetermined pressure cycles continue to be generated.

In at least one embodiment, the predetermined pressure cycles comprise extraction mode pressure cycles, the method further including: manually adjusting a maximum suction pressure to modify the predetermined pressure cycles.

In at least one embodiment, the predetermined pressure cycles comprise extraction mode pressure cycles, the method further including: purging milk from the conduit when the controller identifies that the compression member has reached a location that is a predetermined percentage of a predetermined outward motion limit of the compression member relative to the conduit.

In at least one embodiment, the purging includes: controlling the compression member by the controller to drive the compression member to a predetermined inward motion limit of the compression member thereby driving milk out of a portion of the conduit compressed by the compression member.

In at least one embodiment, the method further includes controlling the compression member to carry out the compression mode cycles after performing the purging.

In at least one embodiment, the predetermined pressure cycles comprise extraction mode pressure cycles, and the controller increases a stroke distance of the compression member relative to an amount of milk entering the conduit, to maintain predetermined pressures during the extraction mode pressure cycles.

In at least one embodiment, the predetermined pressure cycles comprise latch mode cycles, wherein upon determination that milk has entered the conduit or after a predetermined period of time, the controller operates the compression member to achieve predetermined extraction mode pressure cycles, wherein the predetermined extraction mode cycles differ from the predetermined latch mode cycles by at least one of maximum suction level or cycle frequency.

In at least one embodiment, the predetermined pressure cycles comprise extraction mode pressure cycles, and the method further includes: monitoring, by the controller, pressure waves within at least one of the conduit and the skin contact member; monitoring, by the controller, at least one of position and speed of the compression member relative to pressure levels monitored by the monitoring pressure waves; and changing at least one of speed, stroke length and position of the compression member when a predetermined amount of change in the monitored pressure versus monitored position or speed of the compression member is identified, so as to maintain execution of the predetermined pressure cycles.

In at least one embodiment, the controller monitors positions of the compression member; and wherein, upon detecting that the compression member has reached a location that is a predetermined percentage of a predetermined outward motion limit of the compression member relative to the conduit, the controller controls the compression member to purge milk from the conduit.

According to another aspect of the present disclosure, a system for pumping milk includes one or more of: a skin contact member configured to form a seal with a breast; a conduit in fluid communication with and connected to the skin contact member; a driving mechanism including a compression member configured to compress and allow decompression of the conduit in response to inward and outward movements of the compression member; a sensor; and a controller configured to control operation of the driving mechanism; wherein upon sealing the skin contact member to the breast, the controller operates the driving mechanism to generate predetermined pressure cycles within the conduit, monitors at least one of position and speed of movement of the compression member relative to the conduit, measures or calculates pressure within the conduit based upon signals received from the sensor, and maintains or modifies motion of the compression member as needed, based upon feedback from the calculated pressure and at least one of position and speed of movement of the compression member, to ensure that the predetermined pressure cycles continue to be generated.

In at least one embodiment, the predetermined pressure cycles comprise extraction mode pressure cycles, and the system is configured to allow manual adjustment of a maximum suction pressure to modify the predetermined pressure cycles.

In at least one embodiment, the predetermined pressure cycles comprise extraction mode pressure cycles, and the controller operates the driving mechanism to purge milk from the conduit when the controller identifies that the compression member has reached a location that is a predetermined percentage of a predetermined outward motion limit of the compression member relative to the conduit.

In at least one embodiment, the purging includes controlling the compression member by the controller to drive the compression member to a predetermined inward motion limit of the compression member thereby driving milk out of a portion of the conduit compressed by the compression member.

In at least one embodiment, the controller is further configured to control the compression member to carry out the compression mode cycles after performing the purging.

In at least one embodiment, the predetermined pressure cycles comprise extraction mode pressure cycles, and the controller increases a stroke distance of the compression member relative to an amount of milk entering the conduit, to maintain predetermined pressures during the extraction mode pressure cycles.

In at least one embodiment, the predetermined pressure cycles comprise latch mode cycles and, upon determination that milk has entered the conduit or after a predetermined period of time, the controller operates the compression member to achieve predetermined extraction mode pressure cycles, wherein the predetermined extraction mode cycles differ from the predetermined latch mode cycles by at least one of maximum suction level or cycle frequency.

In at least one embodiment, the predetermined pressure cycles comprise extraction mode pressure cycles, and the controller is further configured to: monitor pressure waves within at least one of the conduit and the skin contact member; monitor at least one of position and speed of the compression member relative to pressure levels monitored by the monitoring pressure waves; and change at least one of speed, stroke length and position of the compression member when a predetermined amount of change in the monitored pressure versus monitored position or speed of the compression member is identified, so as to maintain execution of the predetermined pressure cycles.

In at least one embodiment, the controller monitors positions of the compression member and, upon detecting that the compression member has reached a location that is a predetermined percentage of a predetermined outward motion limit of the compression member relative to the conduit, the controller controls the compression member to purge milk from the conduit.

According to another aspect of the present disclosure, a method of purging milk from a milk pumping system after completion of a milk extraction process includes one or more of: providing the system comprising a skin contact member configured to form a seal with the breast, a conduit in fluid communication with and connected to the skin contact member; and a driving mechanism including a compression member configured to compress and allow decompression of the conduit for pumping milk from a breast during the milk extraction process, wherein the skin contact member is sealed to the breast during the milk extraction process; upon completion of the milk extraction process, reversing a direction the driving mechanism to operate in an opposite direction to a direction of the driving mechanism executed to perform the milk extraction process, to decrease suction within the conduit; breaking the seal of the skin contact member with the breast; and reversing the direction of the driving mechanism again, after breaking the seal, to the direction of the driving mechanism executed to perform the milk extraction process, thereby driving milk from the conduit.

In at least one embodiment, upon breaking the seal, the reversing the direction of the driving mechanism again is initiated manually by an operator.

In at least one embodiment, the system detects when the seal is broken and automatically reverses the direction of the driving mechanism upon the detection when the seal is broken.

In at least one embodiment, the method further includes ending the driving milk from the conduit by ceasing operation of the driving mechanism.

In at least one embodiment, the ending is initiated manually by an operator.

In at least one embodiment, the system initiates the ending automatically at a predetermined time after the reversing the direction of the driving mechanism again is initiated.

In at least one embodiment, the system initiates the ending automatically, by measuring a compliance of the conduit and initiating the ending when the compliance reaches a predetermined compliance value.

In at least one embodiment, the reversing a direction of the driving mechanism to decrease suction within the conduit comprises decreasing the suction to greater than −20 mmHg.

In at least one embodiment, the reversing a direction of the driving mechanism to decrease suction within the conduit comprises decreasing the suction and establishing a slight positive pressure.

In at least one embodiment, the reversing a direction of the driving mechanism to decrease suction within the conduit comprises decreasing the suction to about 0 mmHg.

In at least one embodiment, the reversing a direction of the driving mechanism to decrease suction within the conduit, comprises establishing a pressure in the conduit to a value in the range of from about −20 mmHG to about −50 mmHg.

According to another aspect of the present disclosure, a system for pumping milk includes one or more of: a pair of breast pumps, each breast pump comprising: a skin contact member configured to form a seal with a breast; a conduit in fluid communication with and connected to the skin contact member; a driving mechanism configured to establish a vacuum profile within the conduit; a controller configured to control operation of the driving mechanism; and means for indicating whether the breast pump is attached to a left breast or a right breast, when both of the breast pumps are attached to the left and right breasts.

In at least one embodiment, each driving mechanism comprises a compression member configured to compress and allow decompression of the conduit in response to inward and outward movements of the compression member.

In at least one embodiment, the means for indicating is configured to receive a signal by one of the breast pumps from the other of the breast pumps to establish relative locations of the breast pumps.

In at least one embodiment, each breast pump further comprises a magnetic coil, wherein a signal sent to one of the magnetic coils by the controller associated with the magnetic coil in one of the breast pumps induces a signal in the magnetic coil of the other of the breast pumps, the signal being interpretable by the controllers to identify relative positioning of the breast pumps.

According to another aspect of the present disclosure, a system for pumping milk includes one or more of: a skin contact member configured to form a seal with a breast; a conduit in fluid communication with and connected to the skin contact member; a driving mechanism configured to establish a vacuum in the conduit; and means for indicating an amount of wear of at least one of the skin contact member and the conduit.

In at least one embodiment, the means for indicating comprises a time-based indicator.

In at least one embodiment, the time-based indicator comprises a marking that fades or appears over time.

In at least one embodiment, the time-based indicator comprises a clocking mechanism that provides at least one of a visual or audible indication at the end of a predetermined time period.

In at least one embodiment, the time-based indicator comprises an indicator provided with a plurality of LCD bars that darken upon pressing and holding a reset button and the bars lighten sequentially over predetermined time periods.

In at least one embodiment, the means for indicating an amount of wear comprises a wear indicator configured such that at least one of a color change or marking appears or fades to indicate wear.

In at least one embodiment, the system further includes a computer processor, wherein the means for indicating an amount of wear comprises the computer processor configured to track cumulative time of use of at least one of the skin contact member and the conduit.

In at least one embodiment, the means for indicating amount of wear comprises a processor; wherein the processor is configured to: track a position of the driving mechanism relative to the conduit; correlate pressure changes in the conduit relative to the position of the driving mechanism when the conduit is first used; continue to correlate the pressure changes relative to the position during continued uses of the conduit; compare correlation values from the continued correlations with correlation values from the correlations when the conduit is first used; and indicate an amount of wear of the conduit based on the comparison of correlation values.

In at least one embodiment, the processor is included in the breast pump system.

In at least one embodiment, the processor is in an external computer, external to the breast pump system.

In at least one embodiment, the time-based indicator comprises a processor configured to track usage time of at least one of the skin contact member and the conduit.

In at least one embodiment, at least one of the skin contact member and the conduit is provided with a passive sensor, and the processor is configured to track the passive sensor during use of the system.

According to another aspect of the present disclosure, a method of operating a system for pumping milk includes one or more of: providing the system comprising a skin contact member configured to form a seal with the breast, a conduit in fluid communication with and connected to the skin contact member; a driving mechanism including a compression member configured to compress and allow decompression of the conduit in response to inward and outward movements of the compression member, a sensor, a controller configured to control operation of the driving mechanism and to receive signals from the sensor, and a milk collection container in fluid communication with the conduit; sealing the skin contact member to the breast; operating the driving mechanism to extract milk from the breast and pumping the milk into the milk collection container; and calculating a volume of milk pumped into the milk collection container, based on dimensions of the conduit and positions of the compression member.

In at least one embodiment, the calculating a volume of milk pumped comprises: calculating a total volume pumped based on the dimensions of the conduit and the positions of the compression member; calculating the volume of milk pumped as a percentage of the total volume, based on a compliance assessment of the conduit performed by comparing pressure changes of the conduit to positions of the compression member.

In at least one embodiment, the system further includes a one-way valve interconnecting the conduit and the milk collection container, and the method further includes: monitoring the one-way valve to determine when milk begins to flow into the milk collection container and stops flowing into the milk collection container; wherein the calculating a volume of milk pumped into the milk collection container, is based on dimensions of the conduit and positions of the compression member over a time period during which milk is flowing into the milk collection container.

According to another aspect of the present disclosure, a nipple shield includes one or more of: a central region configured to cover a nipple of a breast and having a first thickness; an attachment portion surrounding the central region, the attachment region being configured to attach to the breast and having a second thickness; wherein the second thickness is greater than the first thickness; and wherein the central region comprises one or more openings to allow milk to pass therethrough.

In at least one embodiment, the first thickness is a thickness in the range of about 0.2 mm to about 1 mm and the second thickness is a thickness in the range of about 2 mm to about 5 mm.

In at least one embodiment, the first thickness is about 0.25 mm.

These and other features of the disclosure will become apparent to those persons skilled in the art upon reading the details of the systems and methods as more fully described below.

BRIEF DESCRIPTION OF THE DRAWINGS

FIG. 19 shows characteristics of systems using various tubing dimensions, according to various embodiments of the present disclosure.

FIG. 21A shows a proximal perspective view of a skin contact member according to an embodiment of the present disclosure.

FIG. 21B shows a side view of a skin contact member according to an embodiment of the present disclosure.

FIG. 21C is a cross-sectional view of FIG. 21C taken along line 21C-21C in FIG. 21A.

FIG. 22 shows an indicator mounted on the inside of a breast contact member so that it can be readily viewed by a user prior to mounting the system to the breast, according to an embodiment of the present disclosure.

FIG. 26 shows a wear indictor located on a tubing portion, according to an embodiment of the present disclosure.

FIG. 27 illustrates a wear indicator on a skin contact member, according to an embodiment of the present disclosure.

FIG. 28 illustrates an example of an arrangement for tracking a compression member position, according to an embodiment of the present disclosure.

FIG. 29A illustrates one or more tacky regions provided to facilitate restriction of the breast, according to an embodiment of the present disclosure.

FIG. 29B illustrates one or more tacky regions provided to facilitate restriction of the breast, according to an embodiment of the present disclosure.

FIG. 30A illustrates a skin contact member having a relatively larger internal angle.

FIG. 30B illustrates a skin contact member having a relatively smaller internal angle.

FIG. 30C illustrates a portion of the areola at the juncture with the nipple that needs ample room to expand for optimal extraction of milk.

FIG. 31A schematically illustrates a breast pump system according to alternative embodiments of the present disclosure.

FIG. 31B schematically illustrates a breast pump system according to alternative embodiments of the present disclosure.

FIG. 32A illustrates a milk collection container for use in a system according to another embodiment of the present disclosure.

FIG. 32B illustrates a milk collection container for use in a system according to another embodiment of the present disclosure.

FIG. 32C illustrates a milk collection container that is formed so that the distal surface of the container, when filled with milk has a shape that matches the proximal surface contour of the external shell of the system, according to an embodiment of the present disclosure.

FIG. 33 shows a milk container having baffles that internally connect to the internal walls of portions of the container, according to an embodiment of the present disclosure.

FIG. 34 illustrates a milk collection container that includes a passive sensor, according to an embodiment of the present disclosure.

FIG. 35 illustrates a milk collection container wherein the connector contains a one-way valve, according to an embodiment of the present disclosure.

FIG. 36 illustrates a milk collection container according to another embodiment of the present disclosure.

FIG. 37 illustrates a milk container provided with an easily identifiable marking, according to an embodiment of the present disclosure.

FIG. 39A illustrates various arrangements that may be provided to the system to help prevent loss of milk out of the system upon detachment of the system from the breast, according to embodiments of the present disclosure.

FIG. 39B illustrates various arrangements that may be provided to the system to help prevent loss of milk out of the system upon detachment of the system from the breast, according to embodiments of the present disclosure.

FIG. 40A illustrates a different cross-sectional view of a contour element provided with a breast pump system according to an embodiment of the present disclosure.

FIG. 40B illustrates a different cross-sectional view of a contour element provided with a breast pump system according to an embodiment of the present disclosure.

FIG. 44 illustrates a contour element provided with predetermined markings that may be provided to assist the user in adjusting the contour element to better contour to the breast that it is to be used on, according to an embodiment of the present disclosure.

FIG. 45A illustrates an external shell provided with two keys, according to an embodiment of the present disclosure.

FIG. 45B illustrates a contour element provided with mating keys that are configured to mate with the keys of the external shell of FIG. 45A.

FIG. 46A illustrates a contour element according to another embodiment of the present disclosure.

FIG. 46B illustrates a contour element according to another embodiment of the present disclosure.

FIG. 47 illustrates events that may be carried out by a system during an extraction mode of pumping milk from a breast, according to an embodiment of the present disclosure.

FIG. 48 illustrates a nipple shield according to an embodiment of the present disclosure.

FIG. 49 schematically illustrates apparatus used to perform testing on a light body vinylpolysiloxane breast flange.

DETAILED DESCRIPTION OF THE DISCLOSURE

Figure 1:
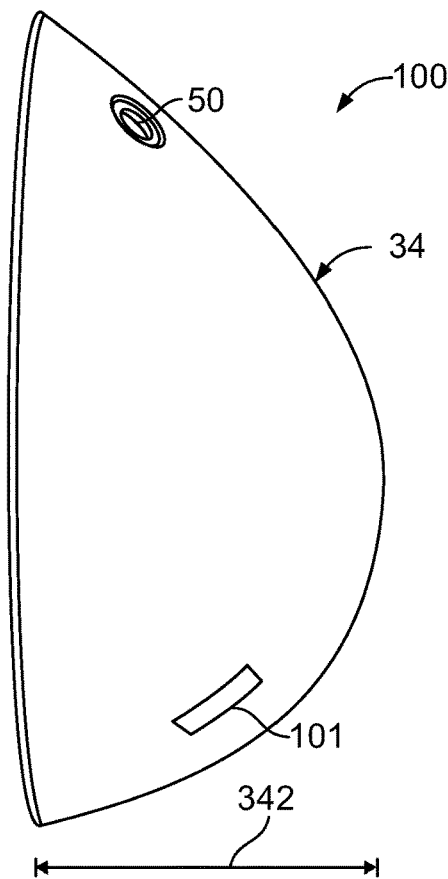
FIG. 1 shows a side view of a breast pump system (without milk collection container) according to an embodiment of the present disclosure.

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a sensor" includes a plurality of such sensors and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

The term "dead space" as used herein refers to volume within the system that is not directly acted upon by the pump of the system. Dead space is calculated by the total volume minus the active pump volume. The total volume is the volume in the skin contact member 10 and tubing 32, from the nipple receiving portion 112 to the one-way valve 50, when the system 100 has been attached and sealed to a breast 2, such that the total volume is the space in the nipple receiving portion 112 not occupied by the nipple 3/areola 4, and the remaining volume from there to the one-way valve 50. The active pumping volume is the volume displaced by the compression member (e.g., compression member 38) when the compression member is moved from one limit of a full stroke to the other limit. The nipple will also move with a changing pressure; the total system volume change is the combination of these two (plus any minor system compliance). The dead space is the non-pumping volume of the system.

"Let down mode", as used herein, refers to a mode where the vacuum profile is characterized by higher frequency and shallower (smaller) magnitude changes in vacuum level. Let down mode may also be referred to as "non-nutritive suction mode" or "non-nutritive mode".

"Extraction mode", as used herein, refers to a mode where the vacuum profile is characterized by lower frequency and deeper magnitude changes in vacuum, relative to "let down mode" (non-nutritive mode). Extraction mode may also be referred to as "nutritive suction mode" or "nutritive mode".

"Purging" refers to an act of transferring milk from the active pumping region of the pump tube into the collection chamber or bag.

"Latch suction" or "latch vacuum" refers to a minimum vacuum level established when the pump is attached to the breast. This is set at the lowest level of vacuum, a pressure which is below atmospheric pressure, which is effective to attach the system to the breast.

Detailed Description

Figure 2:
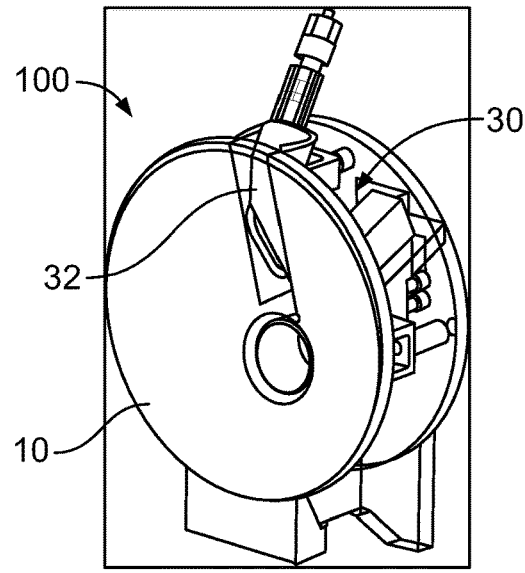
FIG. 2 shows a distal, perspective view of the system of FIG. 1, with the outer shell having been removed/made transparent to show components otherwise covered by the outer shell.
Figure 3:
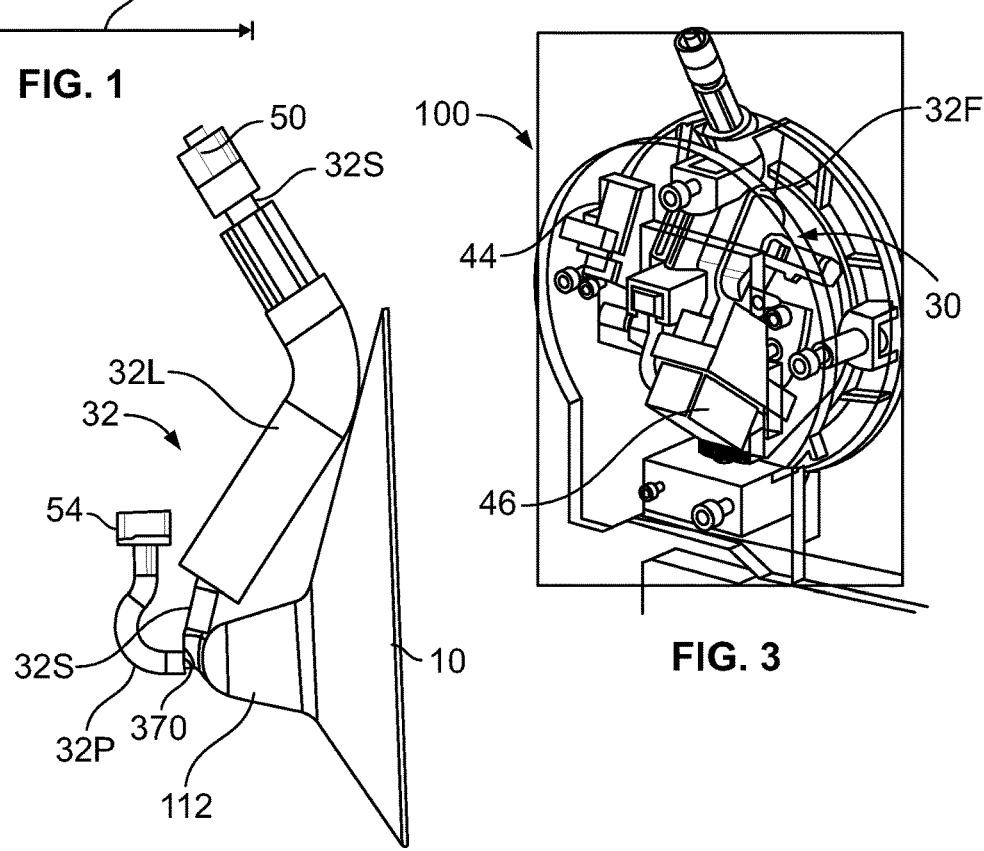
FIG. 3 shows a view as in FIG. 2, but with the skin contact member removed to illustrate more details of the pumping region.

FIG. 1 is a side view of a breast pump system 100 (without milk collection container) according to an embodiment of the present disclosure. The outer shell 34 of system 100 is shaped and configured to be contoured to the breast of a user and to thus provide a more natural appearance when under the clothing of the user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from to the tastes and needs of a user. FIG. 2 is a distal, perspective view of the system 100 of FIG. 1, with the outer shell 34 having been removed/made transparent to show components otherwise covered by the outer shell 34. System 100 includes a skin contact member 10 (such as the breast flange shown in FIG. 2, or member having a different shape, but configured to seal to the breast of a wearer and provide fluid communication with the pump) a pumping region 30 and a conduit 32. FIG. 3 shows a view as in FIG. 2, but with the skin contact member 10 removed to illustrate more details of the pumping region 30.

Figure 4:
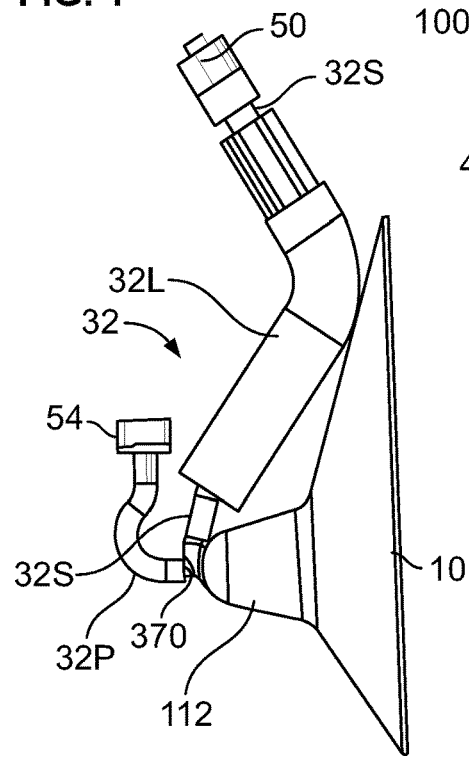
FIG. 4 illustrates components of a system according to an embodiment of the present disclosure.

FIG. 4 illustrates components of a system 100 according to an embodiment of the present disclosure. Conduit 32 includes a large conduit portion 32L that is relatively larger in cross-sectional inside area than the cross-sectional inside area of small conduit portion 32S. Although both portions 32S and 32L are shown as tubular portions being circular in cross-section, the present disclosure is not limited to such, as one or both portions could be shaped otherwise. For example, the conduit region 32L in the embodiment of FIG. 3 is not cylindrical, but is formed as a pump chamber having a substantially oval face 32F and walls that extend substantially perpendicular thereto. Further details of this embodiment of conduit region 32L can be found in U.S. Provisional Application Nos. 62/052,476 filed Sep. 19, 2014 and 62/053,095 filed Sep. 10, 2014, both of which are hereby incorporated herein, in their entireties, by reference thereto. The conduit region 32S2, which joins one way valve 50 and large conduit region 32L in fluid communication, may be, but is not necessarily of the same dimensions as small conduit region 32S. Like regions 32S and 32L, region 32S2 may be cylindrical and circular in cross section, but need not be. When tubular, the cross-sections may be oval square, other polyhedral shape, non-symmetrical, or non-geometric shape.

Figure 5:
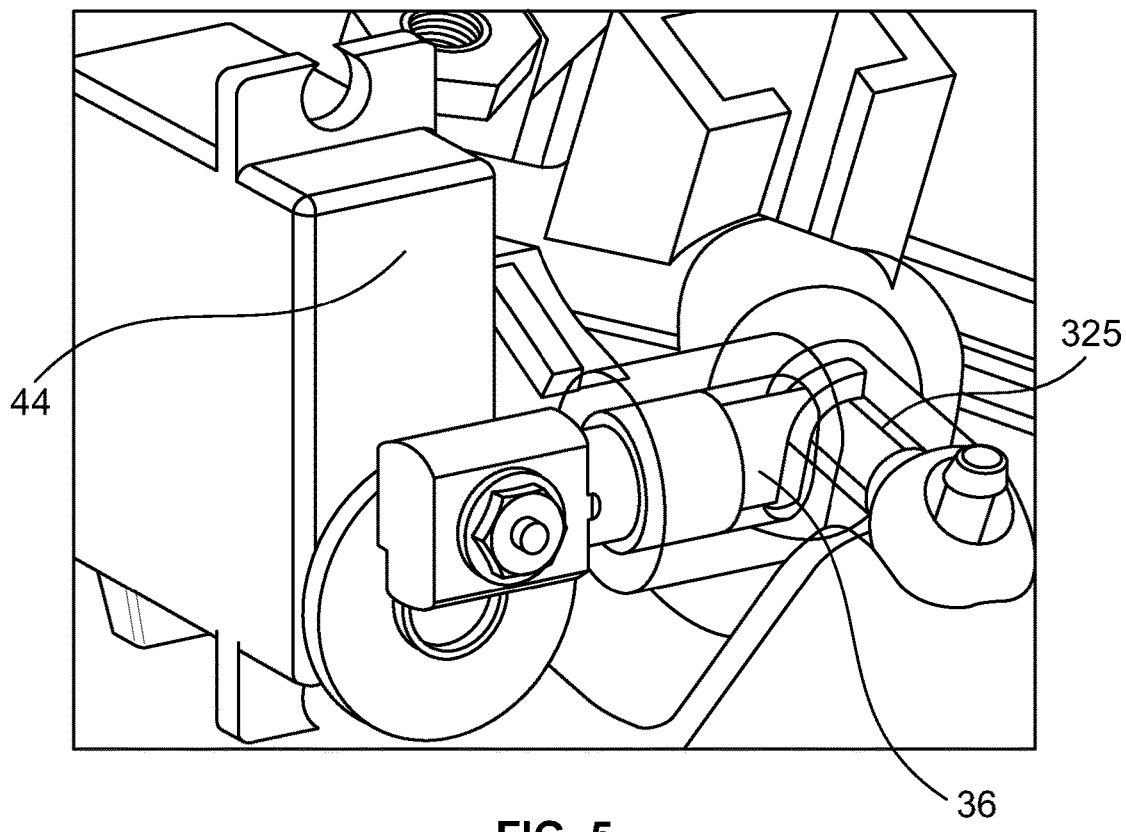
FIG. 5 is a partial view of the system of FIGS. 2-3 showing a compression member and driver in more detail.
Figure 6:
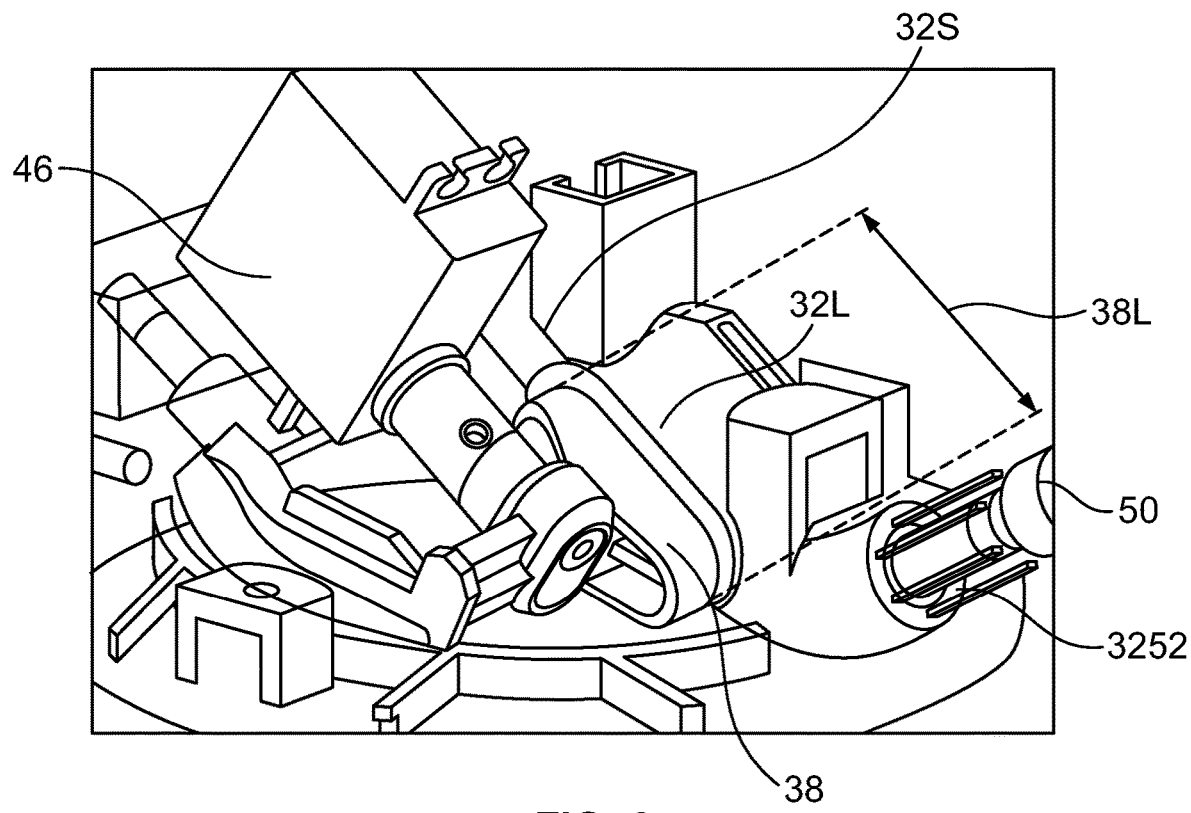
FIG. 6 is a partial view of the system of FIGS. 2-3 showing another compression member and driver in more detail.

In the embodiment of FIGS. 2-3, latching, pumping and extraction forces are established by two compression members 36, 38 which are actively driven by drivers 44 and 46 respectively. Although more than two compression members could be used and one or more than two drivers could be used, the currently preferred embodiment uses two compression members respectively driven by two drivers as shown. FIG. 5 is a partial view of the system 100 of FIGS. 2-3 showing compression member 36 and driver 44 in more detail. FIG. 6 is a partial view of the system 100 of FIGS. 2-3 showing compression member 38 and driver 46 in more detail.

Figure 7A:
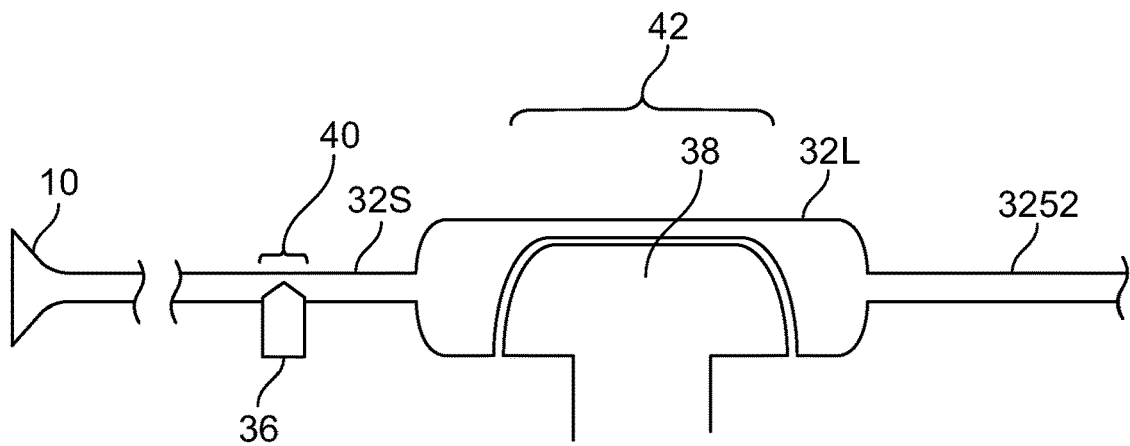
FIG. 7A schematically illustrates one exemplary operation mode of the compression members according to an embodiment of the present disclosure.
Figure 7B:
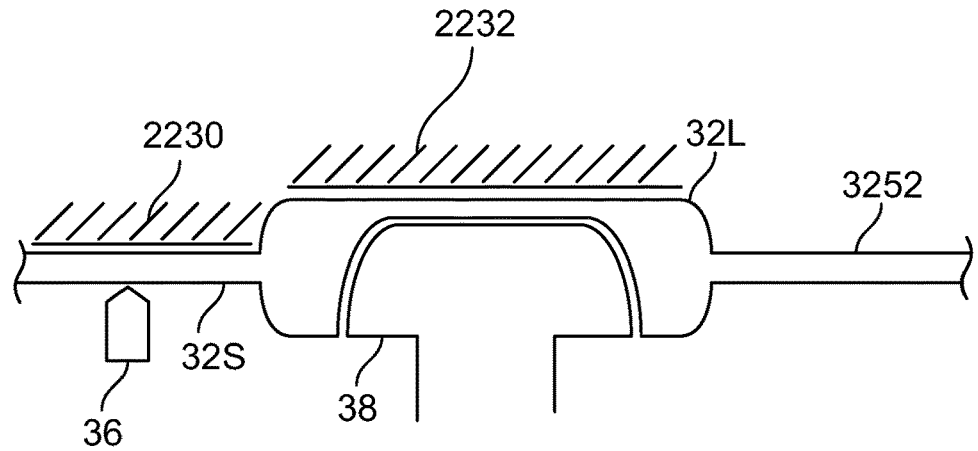
FIG. 7B schematically illustrates one exemplary operation mode of the compression members according to an embodiment of the present disclosure.
Figure 7C:
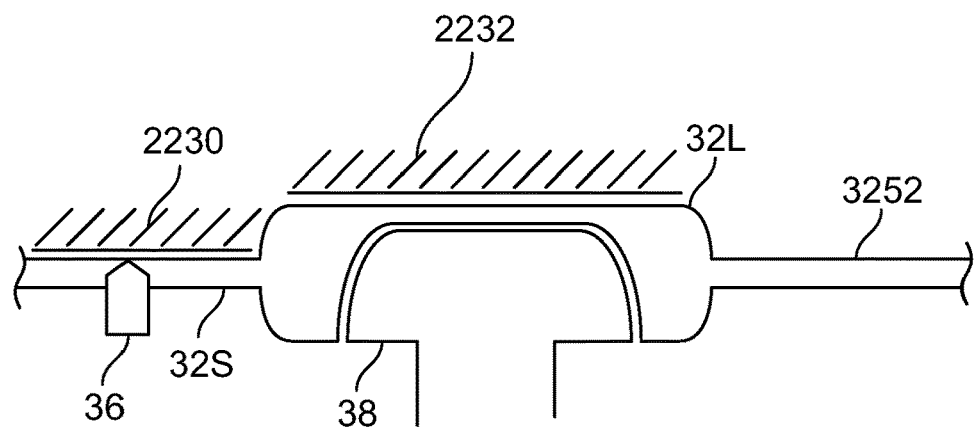
FIG. 7C schematically illustrates one exemplary operation mode of the compression members according to an embodiment of the present disclosure.

FIGS. 7A-7C schematically illustrate one exemplary operation mode of the compression members 36, 38 according to an embodiment of the present disclosure. In FIG. 7A, tubing portions 32S and 32L are closed off, or substantially closed off by compression members 36 and 38, respectively. Upon powering up the system 100 the compression member 36 opens as illustrated in FIG. 7B and the compression member 38 begins to withdraw away from anvil surface 2232 which gradually increases the suction level within tubing 32. When a predetermined maximum suction level is achieved (as confirmed by pressure readings taken from a pressure sensor, described below), the compression member 38 ceases its travel in the current direction, and either maintains that position for a predetermined period of time (or moves slightly in the same direction to compensate for decreasing suction as milk enters the system) when the operating mode of the system 100 has a predetermined time to maintain maximum suction, or reverses direction and compresses the tube 32L until the latch suction level is achieved. If the maximum suction level has not yet been achieved by the time that the compression member is fully retracted away from the anvil surface 2232 on the first stroke, then the compression member 36 again compresses the tube 32S to seal off the current vacuum level in the environment of the breast, and the compression member 38 fully compresses the tube portion 32L to squeeze more air out of the system (out through one-way valve 50). Then the compression member 36 reopens to fully open tube portion 32S and compression member carries out another stroke, again moving away from the anvil surface 2232 to generate a greater suction level. This cycling continues until the maximum suction level is achieved. It is noted that it is possible in some cases to achieve the maximum suction level on the first stroke, whereas in other cases, multiple strokes may be required.

FIG. 7B shows the tubing portion 32S fully open as the compression member 36 is released and compression member 38 is moving away from anvil surface 2232 to increase suction within the tubing 32. Upon achieving the maximum suction, the system may be designed and programmed so that the compression member 38 does not travel to its fullest possible extent in either direction to achieve the maximum and latch suction levels, so as to allow some reserve suction and pressure producing capability. When the maximum suction level has been achieved, and the pumping profile is programmed to return to latch pressure, the compression member 38 advances toward the anvil surface 2232, compressing tubing portion 32L, thereby raising the pressure in the tubing 32. Upon achievement of the latch suction pressure, compression member 36 closes off the tubing 32S again to ensure that the latch pressure is maintained against the breast, so that sufficient suction is maintained. At this stage, the compression member 38 again begins moving away from the anvil surface 2232 to increase the suction level back to maximum suction, and compression member 36 opens (moves away from anvil surface 2230) to allow tube 32S to open and the breast 2 to be exposed to the maximum suction. Alternatively, the system may be programmed so that the compression member 38 cycles between maximum and latch suction levels without the compression member 36 closing during a point in each cycle, with the compression member 36 closing when the latch pressure is exceeded.

Upon selection of a milk extraction mode, the compression member 36 and compression member 38 function in the same manners as in the latch mode, but in a manner that follows an extraction waveform determined by the selected extraction mode. During the compression stroke of compression member 38, compression member 36 closes when the latch pressure/suction level is achieved. Continued compression by the compression member 38 (FIG. 7C) increases the pressure in the tubing 32 downstream of the compression member 36 to establish a positive pressure to drive the contents (milk) of tube portion 32L out of the tube portion 32L through smaller tubing portion 32S2 downstream of 32L and out through one-way valve 50. The positive pressure attained is sufficient to open the one-way valve for delivery of the milk out of the tubing 32 and into a milk collection container. In one embodiment, the positive pressure is in the range of 20 mm Hg to 40 mm Hg, typically about 25 mm Hg. Upon reversing the motion of compression member 38, compression member 36 opens when the suction level returns to the latch suction level and compression member 38 continues to open to increase the suction level to the maximum suction level.

Prior art breast pump systems typically cycle between 0 mmHg (or close to 0) and peak vacuum, which is typically up to 250 mmHg vacuum. The flanges of the prior art systems (i.e., the component that contacts and seals to the breast) typically have a shaped, distal portion and a large cylinder section to accommodate the nipple of the breast as it is drawn forward into the cylinder by the application of vacuum. During pumping with these prior art pump systems, the nipple cycles back and forth significantly matching the cycling of vacuum from 0 to peak set vacuum. This motion is typically at least 1 cm of motion (nipple extends and contracts by at least 1 cm) and can be significantly greater. Studies have shown that the nipple motion resulting from a nursing baby is not very large, e.g., on the order of about 4-5 mm of motion total (Elad paper, other Hartman group papers).

The present disclosure establishes a latch vacuum to cause the skin contact member/breast flange 10 to seal to the breast. The latch vacuum established by the system is currently about 60 mmHg, but can be any value in a range of from about 20 mmHg to about 80 mmHg. Once the system 100 has been latched to the breast via skin contact member 10, the system then cycles between the latch vacuum and a target (also referred to as "peak" or "maximum") suction level. Due to the fact that the system 100 does not cycle down to 0 mmHg, but maintains suction applied to the breast, with the minimum end of the suction cycle being the latch suction level (e.g., about 60 mm Hg), the nipple does not contract as much as it would with use of a prior art breast pump system. It has been observed that the nipple draws into the skin attachment member 10 with the initial latch achievement in an analogous fashion as the formation of a teat during breastfeeding. Once the vacuum cycles between the latch and target vacuum levels, there is significantly less motion of the nipple back and forth with the vacuum changes, as compared to what occurs with use of prior art systems. The nipple motion (distance between fully extended and fully retracted) during use of the present system is typically less than about 2 mm, and in some cases less than about 1 mm.

This greatly reduced motion of the nipple during cycling results from establishment of the latch at latch vacuum level, and then limiting the range of vacuum swing between latch vacuum (suction) and peak vacuum (suction). Typically the difference in vacuum between latch vacuum and peak vacuum is less than 200 mmHg, more typically less than 150 mmHg. In one example, the latch vacuum was 50 mmHg and the peak vacuum was 200 mmHg, resulting in a vacuum difference of 150 mmHg.

Limiting the nipple motion as described with use of the present system offers several benefits to the user. One benefit is that there is less friction on the side of the nipple against the flange wall, thereby greatly reducing the risk of irritation, skin damage, pain, swelling, etc. As a result, the present system is significantly more comfortable to use by a nursing mother, and this benefit is increasingly noticeable over repeated uses. By maintaining at least a latch suction level at all times, the present system provides a more secure and persistent seal to the breast and significantly reduces the potential for leaks of air and/or milk. Because the nipple moves significantly less, this provides a more "natural" feel to the user that more closely simulates the feel of a nursing baby. Because the nipple travels less, this allows for the skin attachment member/flange 10 to be designed as a lower profile component, as its length can be shorter since it does not need to accommodate the greater length in nipple movement experienced by prior art systems. This allows the overall amount of protrusion of the system 100 from the breast to less than that in the prior art, as the overall length of the system is reduced by the reduction in length of the skin contact member/flange 10. Thus, the distance from the tip of nipple to exposed end of the housing the system is reduced.

Figure 8:
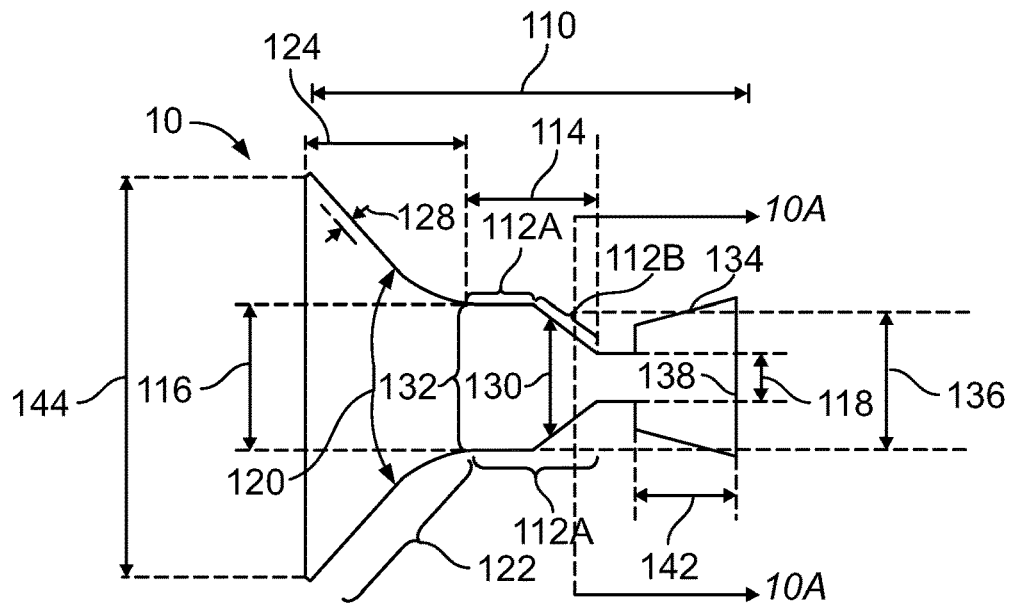
FIG. 8 illustrates a side view of a skin contact member according to an embodiment of the present disclosure.
Figure 9:
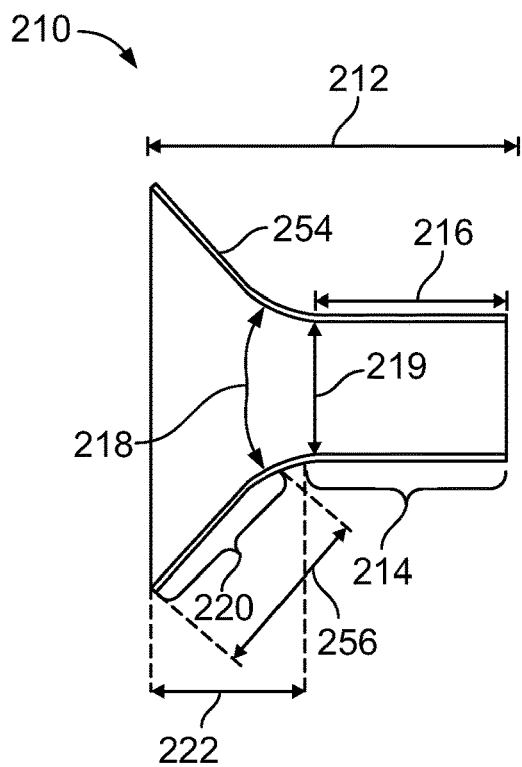
FIG. 9 illustrates a side view of a prior art breast flange.

FIG. 8 illustrates a side view of a skin contact member 10 according to an embodiment of the present disclosure. As shown, the breast contact portion 122 is symmetrical about the nipple receiving portion 112, although, alternatively, the nipple receiving portion 112 could be offset in a manner as described herein. The overall length 110 of the skin contact member 10 in this embodiment is about 63.75 mm. FIG. 9 illustrates a longitudinal sectional view of a prior art breast flange 210. The overall length 212 of flange 210 is about 60.6 mm. The skin contact member 10 is designed to reduce the internal volume of the nipple receiving portion 112 relative to the internal volume of the nipple receiving portion 214 of the prior art device, which is enabled by the significantly reduced amount of motion experienced by the nipple 3 during a milk extraction process using a system 100 including skin contact member 10, according to the present disclosure. The nipple receiving portion 112 of the skin contact member 10 is contoured to more closely match the natural shape of the nipple, thereby eliminating or significantly reducing dead space that exists around the nipple in prior art systems. In the example shown, the nipple receiving portion 112 is cylindrical in the portion 112A adjoining the breast contact portion 122, and then tapers conically in the portion 112B that extends from portion 112A to the connector 134. This design allows for receiving a portion of the areola 4 into the nipple receiving portion 112A while also limiting dead space by providing the conical portion 112B. The diameters of all cross-sections of the nipple receiving portion 112 are large enough to allow nipple dilation. The inside diameter of the conically tapering portion 112B tapers from an inside diameter equal to the inside diameter of the cylindrical portion, down to a smaller inside diameter. As noted, the length of the nipple receiving portion 112 is significantly less than that of the prior art. In the example shown in FIG. 8, the length 114 of the nipple receiving portion 112 is about 23 mm, as compared to the length 216 of 36.9 mm (may be in the range of about 350 mm to about 500 mm) of the prior art nipple receiving portion 214. Length 112 may vary within a range of about 22 mm to about 29 mm. The length 114 of the nipple receiving portion 112 is sufficient to allow engorgement of the nipple 3 under vacuum, without the distal tip of the nipple 3 contacting the proximal end of the nipple receiving portion 112.

Experimentation with the present system 100 has shown that the majority of women's nipples extend into the nipple receiving portion 112 with a length of about 1.6 cm under latch suction of about 50 mmHg (−50 mmHg pressure). The extra length provided by the nipple receiving portion 112 (beyond the length of the nipple under latch vacuum is provided to allow for a small amount of extension of the nipple under target vacuum, typically about 1-2 mm under maximum suction of about 150 mmHg, and to allow for a small amount of additional forward motion the nipple may experience as the pump primes. Accordingly, there is provided at least about 2 mm, up to about 6 mm of space in the nipple receiving portion that extends lengthwise proximally of the tip of the nipple 3 when it is under latch pressure.

The diameter 116 of the nipple entrance to the nipple receiving portion 112 is large enough to accommodate the majority of nipple sizes so that the nipple is not constricted from some engorgement while under vacuum. The nipple 3 expands in diameter by a large amount at the base (the region that joins the areola 4) than it does at the tip, which allows the nipple receiving portion 112B to be made conical-shaped, as shown. The diameter 116 of the entrance opening of the nipple receiving portion 112, in the embodiment of FIG. 8 is about 24 mm, but may be in a range of about 22 mm to about 29 mm. The inside diameter 118 at the proximal end of the nipple receiving portion 112B is about 13.16 mm in FIG. 8, but can be in the range of about 9 mm to about 20 mm. In contrast, the inside diameter 218 of portion 214 of flange 210 is about 23.5 mm over the entire length of the portion 214.

A portion of the areola 4 may also be drawn into the nipple receiving portion 112, so that it is alternately compressed and at least partially relieved of compression by the pumping system 100 to simulate the way a baby naturally feeds. However, the skin contact member 10 is configured to restrict the areola 4 from completely entering the nipple receiving portion 112 and to restrict portions of the breast 2 other than the nipple 3 and areola 4 from entering the nipple receiving portion 112. This prevents the tip of the nipple 3 from contacting the proximal end of the nipple receiving portion 112, even under maximum vacuum.

In any of the embodiments of skin contact member 10 disclosed herein, the top part of the nipple receiving portion 112 may be formed of a relatively harder and/or stiffer material and the bottom part of the nipple receiving portion 112 may be formed of a relatively softer and/or more flexible material to better simulate a nursing baby during use, as the baby's tongue, which contacts the bottom of the nipple 3 is softer and more flexible than the baby's palate, which contacts the top of the nipple 3 during nursing.

To facilitate restriction of the breast 2, the breast contact portion 122 may be provided with one or more tacky regions 360, see FIGS. 29A-29B. Although shown as continuous ring about the interior surface of breast contact portion 122 in FIGS. 29A-29B, tacky region 360 may span one or more portions of this circumference and can be provided as one or a plurality of segments. The tacky region(s) provide more friction with the breast 2 than does the remainder of the skin contact member 10, thereby providing resistance to the portions of the breast 2 that contact it, preventing it from being drawn in toward nipple receiving portion 112. The tacky region 160 may be formed by a different material than the remainder of the skin contact member 10, and/or may be a coating or roughened area to provide the increase in friction. For example, the tacky region may be silicone, with the remainder of the skin contact member being formed of polyethylene, or one of the other materials described herein for using in making the skin contact member. By preventing these portions of the breast from sliding into the nipple receiving portion 112, this reduces incidences of pain from compression of too much breast tissue, and provides sufficient space in the nipple receiving portion 112 for the nipple 3 to naturally engorge for milk volume expression.

The internal angle 120 of the breast contact portion 122 of the skin contact member 10 is designed for use with the present system 100 and to maximize comfort of the user. The internal angle may also facilitate the ability to restrict portions of the breast 2 from moving forward too much into the nipple receiving portion 112. In the embodiment of FIG. 8, the internal angle 120 is about 112°, which is wider than the internal angle of prior art flanges. For example, the angle 218 of the breast contact portion 220 of the prior art flange 210 is ninety degrees. The wider angle 120 helps to prevent the breast tissue from being funneled into the nipple receiving portion 112, so that less breast tissue is received in the nipple receiving portion 112, making use of the present skin contact member 10 more comfortable than flanges of the prior art and providing space for nipple engorgement. By providing the wider angle 120, this also allows the overall system to be effectively shortened and allows the system to lie flatter against the breast to improve both comfort and appearance. In the embodiment of FIG. 8, the length 124 of the breast contact portion 122 is 15 mm, but may be in the range of from about 12 mm to about 19 mm. In contrast, the length 222 of breast contact portion 220 is 25.8 mm, which causes a system using flange 210 to extend further out from the breast than would a system using the skin contact member 10.

FIGS. 30A-30B illustrate differences between skin contact members 122A having a relatively larger internal angle 122A and skin contact member 122B having a relatively smaller internal angle 122B. The smaller angle 122B provides the ability to interact with relatively more breast tissue on more variations in breast sizes and shapes. The breast contact portion of 122A of the skin contact member shown in FIG. 30A has an internal angle 120A that is larger than the internal angle 120B of breast contact member 122B shown in FIG. 30B. As a result, when these skin contact members 10 are mounted to the breast 2, the initial contact of the breast tissue to the breast contact member 122A at 362A is lower on (or further into) the breast contact portion 122A than where the breast tissue initially contacts breast contact member 122B at 362B. The higher (or further out) initial contact location 362B of the breast 2 on the breast contact portion 122B provides more contact surface (compare length 364B to 364A) of the breast 2 on the breast contact portion 122, which better controls the tissue movement in the nipple receiving portion 112 and creates more tension on the teat as it forms, due to the increase surface contact area available. The teat starts to form sooner and the increased tension on the breast aids in holding back breast tissue 2 and the distal portion of the areola 4 from being sucked into the nipple receiving portion 112. A larger length 366B and area for the areola 4 and nipple 3 to form a teat are provided by the smaller angle 120B, relative to the length 366A and area of the embodiment in FIG. 30A, as length 366B is greater than length 366A by an amount sufficient to make the internal volume of the skin contact member over the length 366B greater than the internal volume of the skin contact member over the length 366A. With the larger angle 122A of the embodiment in FIG. 30A, the areola contacts the sides of the breast contact portion 122A upon initial contact of the breast 2 with portion 122A, so that there is no room for the areola 4 to expand. For optimal results, there needs to be a lengthening and widening of the areola 4 during milk extraction, as this is what occurs when a baby suckles. The space provided between the areola 4 and the opening to the nipple receiving portion 112 upon initial contact of the breast 2 to breast contact portion 122, allows the areola 4 to lengthen and expand (widen) as the nipple 3 is drawn into the nipple receiving portion 112. FIG. 30C illustrates the portion 4P of the areola 4 at the juncture with nipple 3 that needs ample room to expand for optimal extraction of milk, as this portion includes milk ducts that will not expel milk as efficiently, or at all, if they are not allowed to expand. The skin contact members 10 of the present disclosure are preferably configured to allow up to about 0.25 inches (about 0.5 cm) length of the areola 4 to be drawn into the nipple receiving portion 112, and to prevent additional portions of the areola from entering the nipple receiving portion 112.

The thickness of the material forming the breast contact portion 122 and nipple receiving portion 112 in the embodiment of FIG. 8B is about 1.5 mm, but the thickness may be in the range of from about 1 mm to about 4 mm. Alternatively, the thicknesses of the breast contact portion 122 and the nipple receiving portion 112 may be different from one another. The breast contact portion 122 and nipple receiving portion 112, as well as the tubing connector 134 can be made of silicone or other compliant, biocompatible material, such as, but not limited to polyurethane and/or polyether block amides (PEBAX) to provide a soft interface with the breast and also provide a seal around the areola and nipple of the breast The inner housing 126 of the breast contact portion 122 can be rigid, semi-rigid or compliant. Likewise, the nipple receiving portion 112 can be rigid, semi-rigid or compliant. Part of the breast contact portion 122 that adjoins and serves as an entrance to the nipple receiving portion 112, is configured to be in contact with at least the perimeter portions of the areola 4 and can be made of a less lubricious material (relative to the lubricity of the nipple receiving portion 112) to provide more frictional resistance on at least the perimeter of the areola to help prevent it from being drawn into the nipple receiving portion 112, and to provide tension on the breast tissue away from the nipple 3 and areola 4, to control the amount of areola 4 that is allowed into the nipple receiving portion 112. Since the present system 100 significantly reduces movement of the nipple 3 during pumping, the surface that provides more friction and tension reduces the risks of chafing or blistering of tissue that would be experienced in a currently available nipple flange, as they experience considerably more nipple 3 movement during pumping. The nipple receiving portion 112 and inner housing 126 can be made of different materials and/or hardnesses and/or rigidity. For example, the inner housing 126 can be rigid and the nipple receiving portion 112 can be compliant, or any other combination of materials, hardnesses and rigidities could be provided. Preferably the breast contact portion 122 and nipple receiving portion 112 are compliant and made from silicone, although other materials and combinations of materials could be used, including, but not limited to or polyethylene terephthalate (PET), polyurethanes, polyethylene, high density polyethylene (HDPE), low density polyethylene (LDPE), polyamides, polyethylene terephthalate (PET) and/or PEBAX. For the embodiments where there is compliance, the nipple receiving portion 112 may be capable of iteratively opening and closing during extraction of milk from the breast using system 100, thereby simulating a feeding cycle similar to the sequence of the tongue against the nipple when a baby is suckling.

In the embodiment of FIG. 8, the nipple receiving portion 112 includes portion 112A which is cylindrical and portion 112B, which is cone-shaped, with the internal angle 130 of cone-shaped portion 112B being about 60 degrees. The internal angle of the cone may be in the range of from about 55 degrees to about 65 degrees.

Figure 10A:
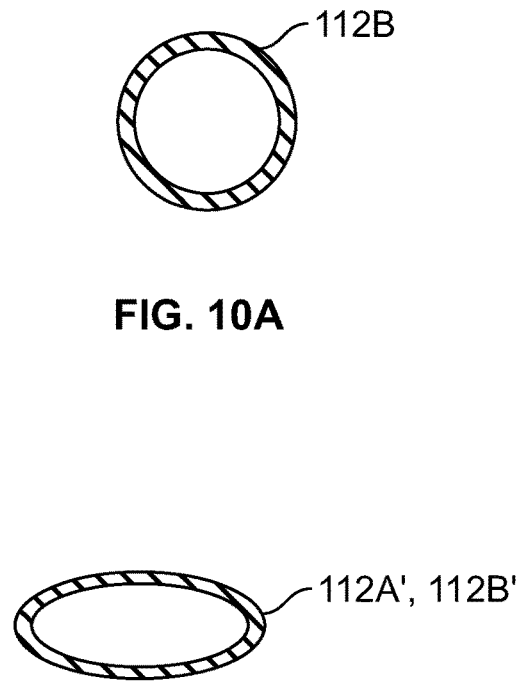
FIG. 10A is a sectional view of structure shown in FIG. 8.
Figure 10B:
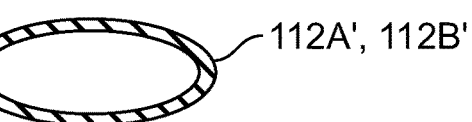
FIG. 10B is a sectional view of an alternative embodiment of a nipple receiving portion according to an embodiment of the present disclosure.

Both the cylindrical portion 112A and the cone-shaped portion 112B are circular in cross-section, as exemplified by the cross-section illustration of FIG. 10A, which is taken along line 10A-10A in FIG. 8. Alternatively, one or both of portions 112A, 112B may be ovular or elliptical in cross-section, as illustrated by 112A', 112B' in FIG. 10B. This ovular or elliptical cross-section more closely resembles the shape of a suckling baby's mouth and will therefore provide a pressure/force contour to the nipple that is more similar to the suckling of the baby.

Further alternatively, the skin contact member 10 may have an adjustable opening 132 to the nipple receiving portion 112 and also the flange angle 120 may be adjustable, so that both the breast contact portion 122 and opening can be sized to optimize the fit against the areola and reception of the nipple. In at least one embodiment, inserts are provided on the inside of the breast contact portion 122. Additionally or alternatively, inserts can be provided on the back of the breast contact portion 122 In any of these arrangements, inserts change the angle of breast contact portion 122 relative to the breast 2 as it is mounted on the breast. Still further, an insert can be provided to make the opening smaller. Different combinations of flange angle 120 and opening 132 diameter may be required for different sizes and shapes of breasts. For example, a relatively smaller opening 132 and relatively smaller angle 120 may be required for a breast that is relatively more elastic than average, while a relatively larger angle 120 and relatively larger opening 132 may be better for a breast that is more taut than average. Further alternatively, a series of skin contact members 10 may be provided to provide a range in angle 120 and opening 132 variations. The wall thickness 128 may also be varied to accommodate changes in the angle 120 of the breast contact portion 122.

Portion 134 is the tubing connector that is used to connect the skin contact member 10 in fluid communication with the tubing 32. The diameter 136 of the opening 138 that provides the fluid communication with the tube 32 is about 25 mm in FIG. 8, but may be in the range of from about 20 mm to about 28 mm. The length 142 of portion 134 is about 23.8 mm in FIG. 8, but may be in the range of from about 20 mm to about 28 mm.

Figure 11A:
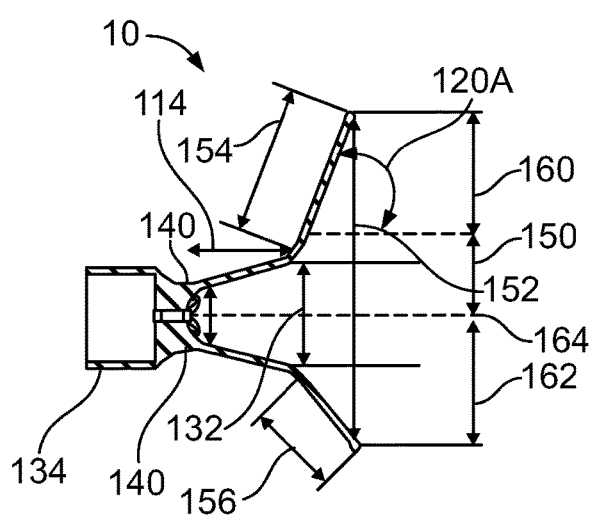
FIG. 11A is a longitudinal sectional view of structure shown in FIG. 11B.
Figure 11B:
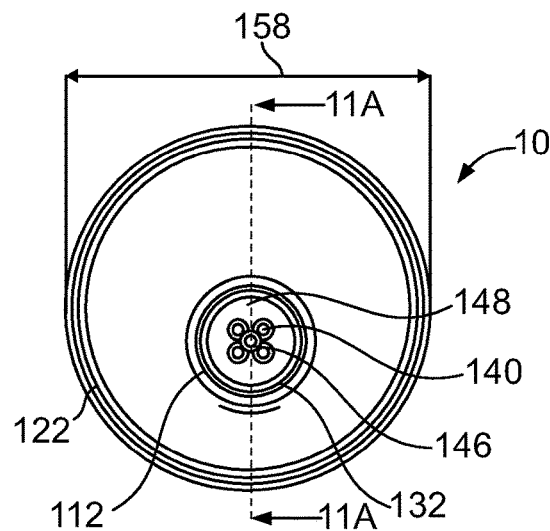
FIG. 11B is a distal end view of a skin contact member according to another embodiment of the present disclosure.

FIG. 11A is a longitudinal sectional view taken along line 11A-11A in FIG. 11B and FIG. 11B is a distal end view of a skin contact member 10 according to another embodiment of the present disclosure. In this embodiment, the nipple receiving portion 112 is not centered with respect to the breast contact portion 122, in contrast to the embodiment of FIG. 8 where the breast contact portion 122 is concentric with nipple receiving portion 112. Instead, in this embodiment, the central axis 146 of the nipple receiving portion 112 is positioned below the central axis 148 of the breast contact portion 122, when the skin contact portion is placed in the orientation in which it is used for attachment to the breast, see FIG. 11B. In this embodiment, the opening 132 to the nipple receiving portion 112 is slightly larger in diameter than that of the embodiment of FIG. 8, (25 mm vs. 23 mm) to accommodate users with slightly larger nipples. The opening diameter 219 of the prior art flange 210 shown in FIG. 9 can be in the range of about 21 mm to about 32 mm. Of course, the offset embodiments of the present disclosure could also use the smaller opening 132 size. Likewise, the embodiment of FIG. 8 could be provided with the larger opening 132 size. In this offset embodiment, the angle 120A of the breast contact portion 122 that is above the nipple receiving portion 112, relative to the central axis 150 of the breast contact portion 122 (and the central axis 164 of the nipple receiving portion 112 when the central axes 150 and 164 are parallel, as in the embodiment of FIG. 11A) is flatter than the angle 120B of the breast contact portion 122 that is below the nipple receiving portion 112, relative to the central axes 150 and 164, see FIG. 11A. In other embodiments, central axis 150 is not parallel with central axis 164. In the example shown in FIG. 11A, angle 120A is about 69 degrees and angle 120B is about 52 degrees. However, angle 120A may be any angle in the range of from about 32 degrees to about 85 degrees and angle 120B may be any angle in the range of from about 32 degrees to about 85 degrees. This configuration provides a better fit to the natural curvature of the breast to which the breast contact portion 122 is contacted, relative to a design where both angles 120A and 120B are equal. To maintain the plane of the perimeter around the distal opening 152 of the breast contact portion 122 substantially normal to the central axis 150 as shown in FIG. 11A, the distance 154 from the top of the opening 132 to the top of the perimeter of distal opening 152 is greater than the distance 156 from the bottom of the opening 132 to the bottom of the perimeter of distal opening 152, due to the difference in angles 120A and 120B. In the example shown in FIG. 11A, distance 154 is about 36.32 mm, but may be any value in the range of from about 15 mm to about 62 mm; and distance 156 is about 21.3 mm, but may be any value in the range of from about 10 mm to about 58 mm. The outside diameter 158 of the breast contact portion 122 at the distal opening (see FIG. 11B) is about 82.3 mm, but may be any value in the range of from about 60 mm to about 150 mm. The distance 160 from the top of the perimeter of the distal opening 152 to the central axis 164 of the nipple receiving portion is about 49.8 mm in the embodiment of FIG. 11A, but may be any value in the range of from about 30 mm to about 60 mm. The distance 162 from the bottom of the perimeter of the distal opening 152 to the central axis 164 of the nipple receiving portion in the embodiment of FIG. 11A is about 33 mm but may be any value in the range of from about 25 mm to about 40 mm. In contrast, the flange 210 of FIG. 9 is symmetrical, with the distance 254 from the top of the perimeter of the distal opening to the central axis of the flange 210 being 28.2 mm and the distance 256 from the bottom of the perimeter of the distal opening to the central axis of the flange 210 being 28.2 mm.

Multiple holes or ports 140 are provided at the interface of the nipple receiving portion 112 with the tubing connector 134 to allow the breast milk drawn from the nipple 3 to enter the tubing 32 connected to the tubing connector 134 and in fluid communication with holes/ports 140. These holes/ports 140 allow milk to be delivered into the tubing connector 134 and tubing 32, and also prevent the nipple 3 from being drawn into the tubing connector 134 and tubing 32.

Figure 12A:
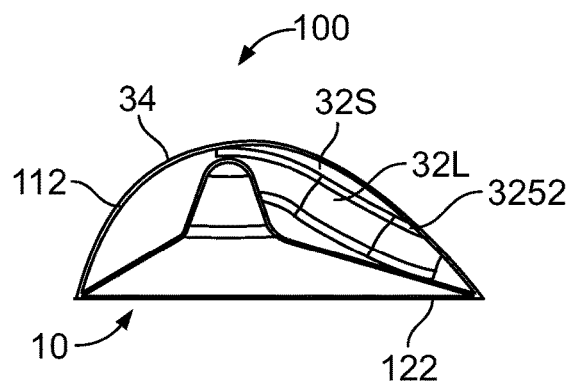
FIG. 12A is a side, cross-sectional view of a skin contact member according to an embodiment of the present disclosure.
Figure 12B:
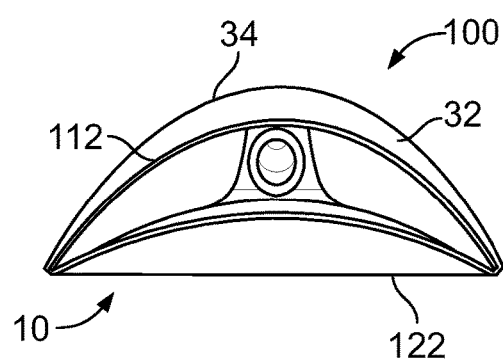
FIG. 12B is a transverse, cross-sectional view of the skin contact member of FIG. 12A taken from the bottom of the system, showing the skin contact member and tube with the outer shell.
Figure 12C:
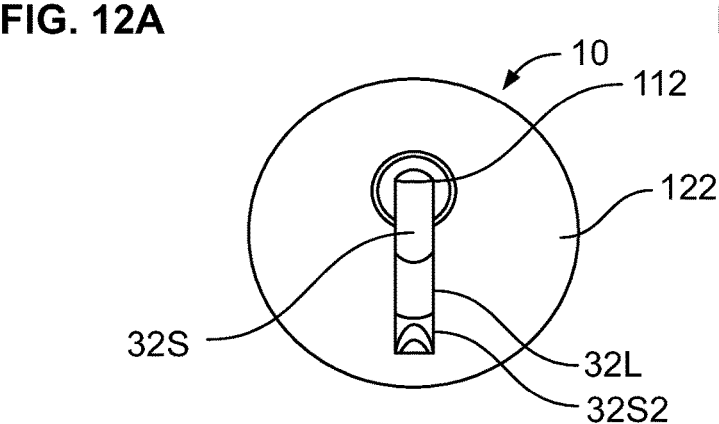
FIG. 12C is a proximal end view of the skin contact member of FIG. 12A showing a tube connected thereto.

FIG. 12A is a side, cross-sectional view of the skin contact member 10 and tube 32 with the outer shell 34. FIG. 12B is a transverse, cross-sectional view from the bottom of the system 100 showing the skin contact member 10 and tube 32 with the outer shell 34. Although tube 32 is shown schematically as a single sized tube for simplicity, the large portion 32L in this embodiment has an inside diameter larger than the inside diameter of smaller tube portions 32S. FIG. 12C is a proximal end view of the skin contact member 10 showing tube 32 connected thereto. In one embodiment, the inside diameter of the tube 32L is about ⅜". In another embodiment, the inside diameter of the tube 32L is about 7/16". In another embodiment, the inside diameter of the tube 32L is about ½". In another embodiment, the inside diameter of tube portion 32L is about 5/16". In one embodiment, the inside diameter of tube portions 32S and 32S2 is about ¼". In another embodiment, the inside diameter of tube portions 32S and 32S2 is about 3/32". In another embodiment, the inside diameter of tube portions 32S and 32S2 is about ⅛".

Figure 13:
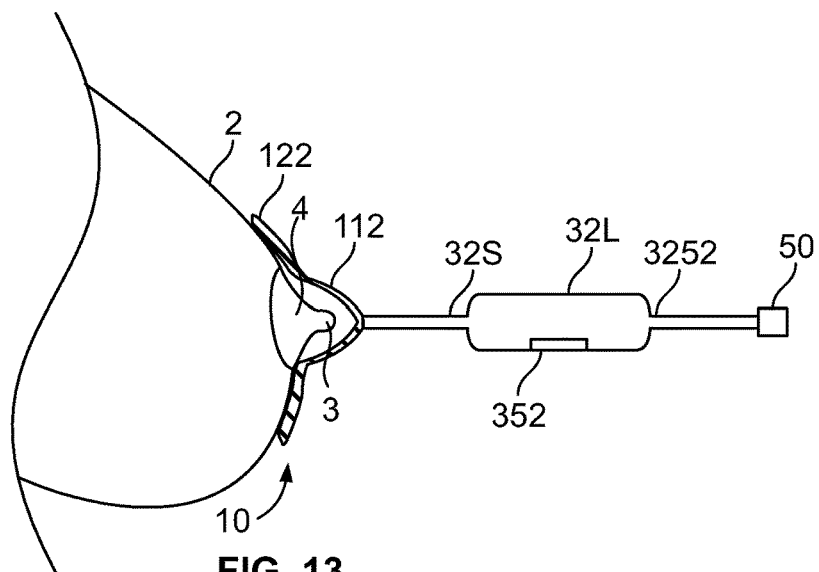
FIG. 13 is a schematic representation showing components defining the total system volume according to an embodiment of the present disclosure.
Figures 14, 17:
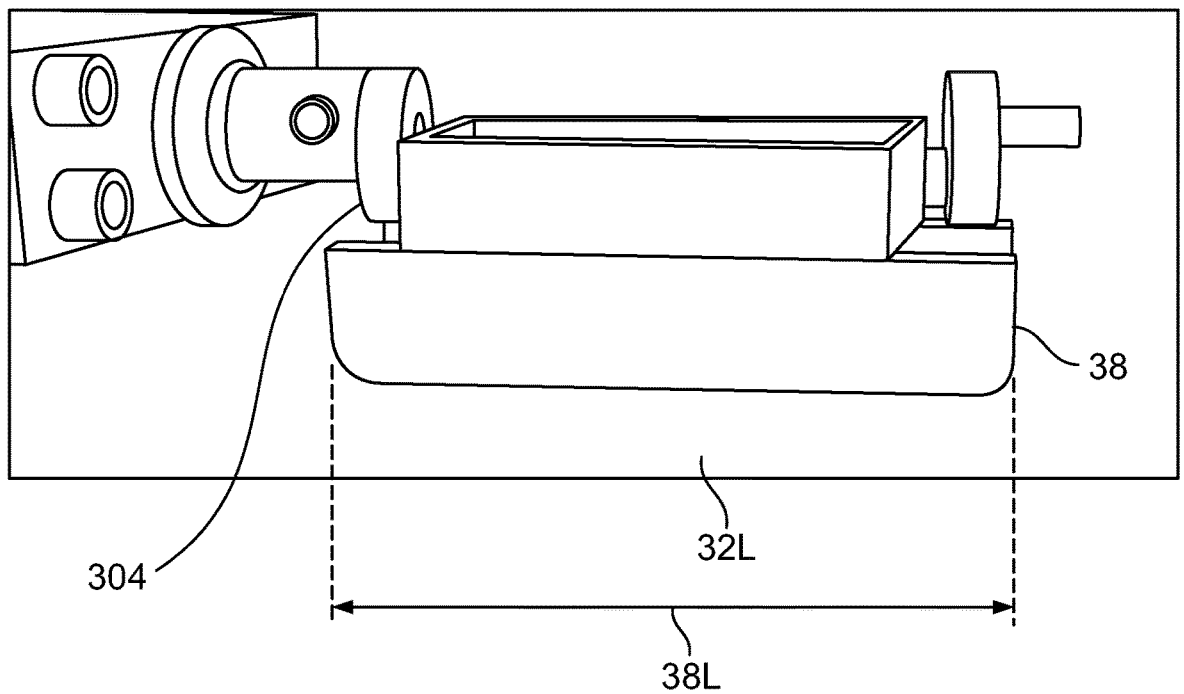
FIG. 14 shows a compression member compressing a tubing portion, according to an embodiment of the present disclosure.
FIG. 17 shows the power consumption data for a system according to an embodiment of the present disclosure.

In one embodiment, the total system volume is about 24.0 cc. The total volume is calculated as the space in the nipple receiving portion 112 (that is not occupied by the nipple 3) and tube portions 32S, 32L and 32S2 up to the one-way valve 50, see the schematic representation in FIG. 13. Other embodiments may have a significantly less total system volume, in the range of about 4 cc to about 24 cc, preferably in the range of about 4.5 cc to about 12 cc, more preferably in the range of about 5 cc to about 8 cc or about 8 cc to about 10 cc. In the embodiment with total system volume of about 24.0 cc, the active pump volume, i.e., the volume displacement achievable by compressing tube portion 32L from fully uncompressed to the limit of compression by compression member 38 is about 3.4 cc. The compression member 38 in this embodiment has a compression member length 38L (with length defined as shown in FIG. 14, 38L) of about 2.5". When there is only air in the tubing 32 of the system 100, pressure swing by moving the compression member 38 inwardly against the tubing portion 32L and outwardly away from the tubing portion is limited, due to the compressibility of the air. In this embodiment, with the system under vacuum of −60 mmHg, a full stroke of the compression member (from compressed to fully uncompressed tube portion 32L) increases the vacuum to −160 mmHg. The ratio of pumping volume to total system volume is important with regard to power and size of the pumping system. In this embodiment, the tube portion 32L was made of silicone (Dow Corning SILASTIC®) having a 0.375' inside diameter and a wall thickness of 0.094", with a hardness of 50 Shore A. Using the 2.5" long compression member, the force applied to the tube portion 32L under full compression was 19.6 lbf.

Figure 15:
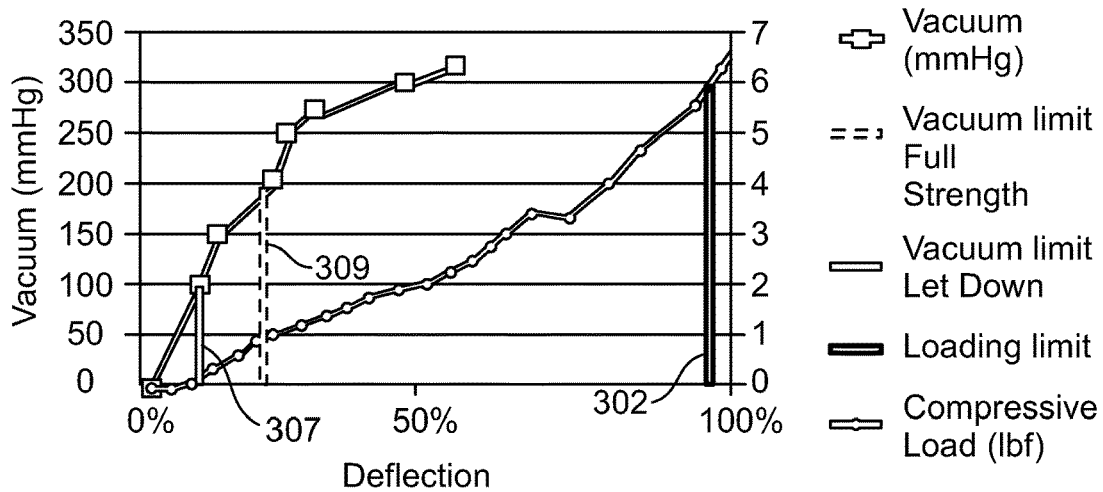
FIG. 15 is a chart illustrating relationships between tubing volume, tubing deflection and load on the compression member, according to an embodiment of the present disclosure.

In a preferred embodiment, it is preferred to avoid both completely compressing the tube portion 32L and well as allowing full rebound of the tubing portion 32L. Near full compression, a sharp increase in compression force is required (see FIG. 15, #302), which is not efficient for the small amount of additional pressure change obtained thereby, given the significant increase in motor power and energy consumption that it would require. Near full rebound of the tubing portion, the resulting pressure changes are less efficient, given the amount of energy expended by the driver 46 to withdraw the compression member 38 fully, see FIG. 15, #305 During let down mode operation of the system 100, the system 100 operates to effect let down of the milk in the breast 2, prior to extraction, with a maximum suction target of up to 120 mmHg (typically, about 100 mmHg (−100 mmHg pressure)) to establish let down. The goal of letdown mode (or non-nutritive suction mode) is to stimulate the breast 2 to express milk. The relatively shallow (small vacuum change range) and relatively fast frequency of the pumping during this phase are meant to mimic the initial suckling action of a child at the breast. In this mode, the first 10% of the tubing compression (FIG. 15, #305) is less productive. This is because during let down phase, the suction pressure is not allowed to exceed the maximum let down suction of 110 mmHg or 120 mmHg, or whatever the maximum let down suction is set at, so the compression member 38 does not cycle to the range of the first 10% of the tubing compression. Therefore, as the compression member 38 is drawn in a direction away from the tube portion 32L, the system 100 is designed to reach −100 mmHg (a suction pressure of 100 mmHg) (or −120 mmHg, or whatever the maximum let down suction is designed to be), by the time that the compression member 38 has reached a position in which tube 32L is 90% uncompressed, see 307. Further movement of the compression member 38 away from the tube portion 32L from 90% to 100% compressed (see region 305) is less helpful to generate additional vacuum as the tube portion 32L functions like a weak spring during this portion of expansion. The chart in FIG. 15 tracks the rebound pressure generation by the tube portion 32L after compression to a specific level. For example, 100% compression of tube portion 32L followed by sealing the tube and letting it rebound would generate >300 mmHg. A small deflection generating 10 mmHg is not 'useful' for pumping purposes of the system 100. 200 mmHg vacuum is established when the tubing 32L is about 25% compressed and then released, see 309. The compression member 38 needs only to actuate within the ranges of vacuum generation that are useful for the pumping purposes of the system 100. Actuating the compression member 38 to compress the tube portion 32L near 100% is inefficient due to the compression load ramping up. Also, actuating the compression member 38 paddle near 0% compression of the tubing portion 32L is only useful for controlling low vacuum peaks. As the tubing portion 32L rebounds it reaches its capacity for vacuum draw and further withdrawal of the compression member 38 away from the tubing portion 32L only causes the paddle to lose contact with the tubing portion 32L.

During let down (non-nutritive) mode the system 100 can be configured to operate between −60 mmHg and −100 mmHg in one example. In this example, the compression member 38 can compress the tubing portion 32L nearly fully (e.g., about 97%) and then be moved away from the tubing portion 32L to generate vacuum. The maximum latch suction pressure of −100 mmHg will be reached with a small amount of rebound of the tubing portion 32L and the compression member 38 can be cycled relative to the tubing portion 32L between −100 mmHg and −60 mmHg in a narrow range or band near full compression of the tube portion 32L. As milk flows, that narrow band shifts (volume in→paddle lifting) until 100 is generated around 10% (90% rebound) at which point the tube portion 32L will be purged by fully compressing it (up to or near 100% compressed) to drive out the contents and thereby regain more capacity for pumping with relatively less compression of the tube portion 32L again. In another embodiment, compression member 38 operates in a range to compress tube portion 32L from about 10% compressed up to about 97% compressed. Additionally, the compression member 38 can move to a position where tube 32L is 0% compressed to allow for installation, changing, etc. of the tubing 32. Typically during purging, the vacuum level is reduced to minimum vacuum (e.g., about −60 mmHg) and the compression member 36 is used to close off (seal) tubing portion 32 to maintain 60 mmHg vacuum against the breast 2. Then the compression member 38 fully compresses the tubing portion 32L to purge the contents of tubing portion 32L.

Figure 16:
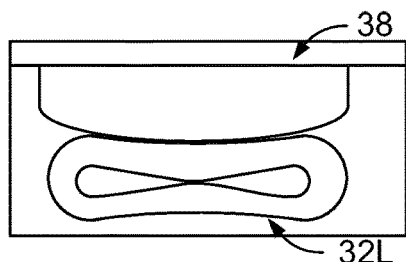
FIG. 16 illustrates compression of a tubing portion by a compression member, according to an embodiment of the present disclosure.

The contact surface of the compression member 38 can be shaped to improve pumping efficiency and reduce power requirements of the system 100. FIG. 16 shows an end view of compression member 38 during compression of tubing portion 32L. The contact surface 38S of compression member 38 is convex in the direction transverse to the longitudinal axis of the compression member 38, such as by radiusing, for example, to avoid unproductive crushing of the side walls of the tube portion 32L. This minimizes the peak load on the driver 46. It can be seen in FIG. 16 that the central portion of the tube 32L is completely closed as the inner walls contact one another, while the portions near the sides of the annulus do not completely close off.

For the embodiment having the total system volume of 24.0 cc, 19.6 lbs. pumping force was provided by the driver 46 and compression member 38. The estimated mechanism capacity was 44 lb. "Mechanism capacity" refers to the maximum compression force that could be applied to the tubing portion 32L by the driver 46 and compression member 38, and is a factor of voltage, driver 46 stall torque, and other characteristics of the drive train, such as gear reduction, etc. The system used a servo motor as the driver 46 connected to the compression member 38 with a 0.188" lever arm 304 (see FIG. 14), to provide a 246:1 gear ratio and 5.9 ft-lb. torque with a 500 mA current draw. The maximum desired speed of this pump system is 90 cycles/min (CPM), with full compression travel limited to about 65 CPM. When the compression travel (stroke) is reduced, such as when in letdown mode, the speed can be increased. The pump system has a 'dry' 100 mmHg swing (i.e., change in vacuum is about 100 mmHg from one end of a full stroke to the other when there is no fluid in the tubing 32), so the full travel stroke may not be required in letdown mode, as the vacuum swing is less than 100 mmHg, e.g., about 60 mmHg latch suction to about 100 mmHg maximum suction. The force requirements of the pumping system can be greatly reduced by reducing the dead space in the total system volume, which in turn then requires less pumping volume per cycle/stroke. By reducing the gear ratio, this can increase the actuation of the compression member to make it quicker and more responsive to pressure changes.

The driver 44 and compression member 36 were configured to apply about 1.0 lbf to the tube having ⅜" inside diameter, to fully close (pinch) it off. Driver 44 included an HS-85MG servo motor having dimensions of 0.51"×1.14"×1.2", a 3.0 in-lb. stall torque and 0.238" lever arm to provide about 12.8 lbf capacity.

FIG. 17 shows the power consumption data for the system described above having 24.0 cc total system volume, 0.375" inside diameter tube 32, and 2.5" compression member 38 described above. The drivers 44, 46 were powered by four alkaline "C" sized batteries which provided a voltage 330 of about 6V. The currents were measured using a multimeter in series with the battery connection to the drivers. The system was set to drive the compression member 38 over the full stroke relative to the tube portion 32L during operation. A single 15 minute pumping session required about 110 mAh of power, see 336. An estimate for a day's worth of pumping was set as four sessions, resulting in the power requirement for a full day 338 to be about 440 mAh. The average current 332 was calculated to be about 440 mA and the maximum current 334 capability was about 0.83 A.

Figure 18:
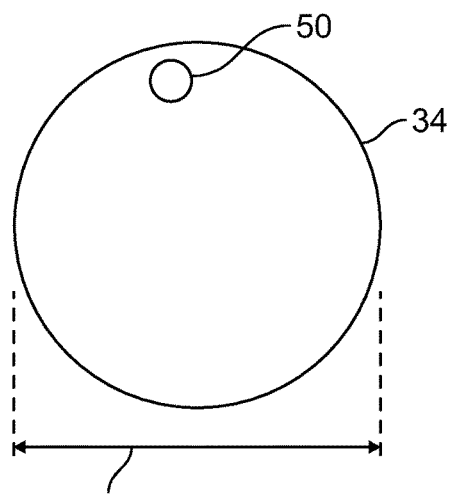
FIG. 18 is an end view of an external shell of a system according to an embodiment of the present disclosure.

In one embodiment, the external shell 34 that contains the other components of the breast pump system (except for the milk collection container which is mountable over the external shell 34) is configured to have about an 11 cm (4.3") diameter 340 (see FIG. 18) and a length 342 (see FIG. 1) of about 4.1 cm (1.6"), although the diameter 340 may be any value within the range of from about 10 cm to about 14 cm and the length 342 may be a value within the range of from about 3.5 cm to about 6 cm. An external shell 34 having a diameter 340 of about 11 cm and length 342 of about 4.1 cm provides a housing volume for the components of about 151.2 cc. Assuming dead volume in the nipple receiving portion 112 to be about 1.8 cc and a 1 cm length of tubing 32 provided for compression by compression member 36 with the nipple receiving portion 112 off center of the breast contact portion 122 by about 1.5 cm, FIG. 19 shows characteristics of systems 100 using various tubing dimensions. These characteristics were measured using tubing 32 that was uniform throughout and thus did not have a smaller tubing portion 32S and larger tubing portion 32L, but the principle still holds for using tubing 32 having both small 32S and large 32L portions. It can be seen that reducing the dead volumes 350 and 352, the pumping efficiency 354 (pumping volume divided by total system volume 352+356) increases. This allows a reduction in the length 38L of compression member 38, resulting in relatively lower pump power and energy consumption requirements.

Figure 20:
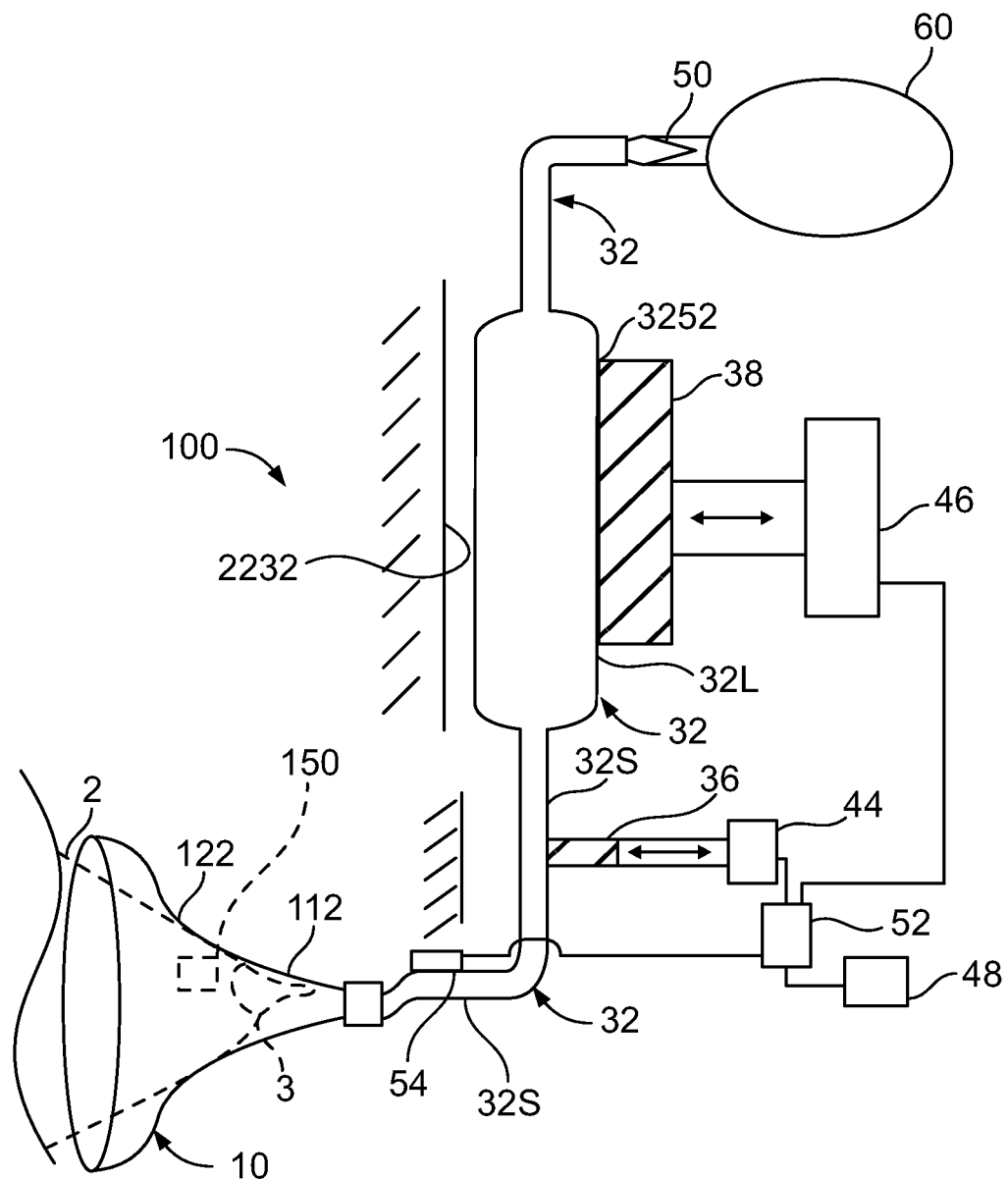
FIG. 20 is a schematic representation of working components of a system according to an embodiment of the present disclosure.

The system 100 is responsive to pressure changes within the tubing 32 caused by entry of milk into the tubing 32. FIG. 20 is a schematic representation of working components of the system 100 according to an embodiment of the present disclosure. The compression elements 36 and 38 are driven by dedicated compression drivers 44, 46. Alternatively, compression elements 36 and 38 could be driven by a single compression driver, controlled by controller 52 to drive each of the compression elements 36, 38 in the manner desired. As shown, the compression elements 36, 38 comprise pistons, but alternative features could be used to accomplish the same function, such as lever arms, screw drives, clamps, cams, pincers, rollers, magnets, electromagnets, linear drives, solenoids, gears, stepper motors, or other features, respectively. Further characteristics of alternative embodiments of compression members and compression surfaces thereof can be found in U.S. Provisional Application Ser. Nos. 62/027,685, filed Jul. 22, 2014; 62/050,810, filed Sep. 16, 2014; 62/052,476, filed Sep. 19, 2014; and 62/053,095, filed Sep. 19, 2014; each of which is incorporated herein, in its entirety, by reference thereto.

Each compression element 36, 38 is operatively connected to a driver 44, 46, respectively, for independent, but coordinated driving and retraction of the compression elements 36, 38. When electrically-powered drivers are used, a battery 48 is electrically connected to the drivers 44, 46, as well as the controller 52 and pressure sensor 54, and supplies the power necessary to operate the drivers 44, 46 to drive the compression and retraction of the compression elements 36, 38.

A sensor 54 is used to provide feedback to the controller 52 for controlling the pumping cycles to achieve and/or maintain desired vacuum levels. Sensor 54 is preferred to be a pressure sensor but could also be a flow, temperature, proximity, motion sensor or other sensor capable of providing information usable to monitor the safety or function of the pump mechanism of system 100. As shown, sensor 54 is a non-contact sensor 54, meaning that it is not in fluid communication with the milk or vacuum space of the system 100. Preferably sensor 54 is located nearby where the tip of the nipple 3 of the breast 2 is located to determine actual pressure being exposed to the breast 2/nipple 3, but other sensors 54 may be located within the system 100, for example, near where the one-way valve 50 is located, and can be used to monitor other features such as container 60 contents or expulsion pressure or flow rate. More generally, sensor 54 can be located anywhere in the system between the breast 2 and the one-way valve 50 into the collection container 60. Sensor 54 can be located either on the breast side of the compression member 36 or the other side of the compression member 36. When located on the breast side (i.e., upstream of the compression member 36), the sensor always provides the pressure experienced by the breast 2 and can thus be used to monitor and determine the pressure environment of the breast 2 even when the compression member 36 has sealed off the tubing portion 32S. If the sensor 54 is on the other side of the compression member 36 (i.e., downstream of the compression member 36), sensor 54 can always provide pressure at the breast 2 except when the compression member 36 has sealed off the tubing portion 32S. Thus, a sensor 54 can be placed anywhere in communication with tube 32 and be used to monitor and control the system via sensor readings feedback to the controller 52. With at least one sensor 54 present, by monitoring either flow or pressure directly or indirectly and also taking into account the cycles and actual positions of the compression elements 36, 38 over time, it is possible to derive/calculate approximately the volume of milk produced during a pumping session as well as understand the flow-rate at any particular time in a pumping session. The accuracy of this measurement is greatest when there is no leak of air around the breast 2 and also when there is negligible air within the tube 32, after elimination by a few cycles of the pumping mechanism.

A one-way valve 50 such as a duckbill valve or other type of one-way valve is provided at the end of tube 32 where it enters the milk collection/storage container 60 (or, alternatively, can be connected in fluid communication with the storage container by another tube. Valve 50 prevents back flow of milk into the tube 32, as well as preventing air from entering the proximal end of the tube 32 and thereby maintains the suction (vacuum) level in the tube 32. Valve 50 can further be designed to open in the reverse direction, for safety purposes, if a predetermined maximum vacuum level is exceed in tubing 32, such as greater than 250 mm Hg vacuum (−250 mm Hg pressure), for example. In at least one embodiment, the pressure at which the valve 50 opens to allow flow into the milk collection container 60 is about 25 mm Hg. In an alternative embodiment, a pressure relief valve 150 can optionally be provided in the system 100, such as in the skin contact member 10, or other location along tubing 32. The pressure relief valve 150 can be configured to release at vacuums greater than a predetermined amount, (e.g., vacuums greater than 250 mm Hg (pressures less than −250 mm Hg), or some other predetermined maximum vacuum level). The one-way valve 50 can be configured and designed such that it allows fluid to flow through it when the pressure in tubing 32 is positive, e.g., about 25 mm Hg, or some other predesigned "crack pressure". The action of the compression elements cycles between increasing vacuum when the compression elements move in a direction away from tube 32 and decreasing when the compression elements compress the tube 32, but typically should not increase the vacuum to greater than the predetermined maximum vacuum. As the compression elements 36, 38 compress the tube 32, the pressure in the system 100 goes up and reaches the minimum suction level (e.g., latch suction level, such as −60 mmHg, −30 mm Hg, or some other predetermined latch suction level), at which time the compression member (pinch valve) 36 seals off portion 32S thereby maintaining the minimum suction (latch suction) against the breast 2. Continued compression of portion 32L by compression member 38 continues to increase the pressure downstream of compression member 36, until the crack pressure is reached (e.g., 25 mm Hg or some other predetermined, positive crack pressure), that opens the one-way valve 50. The compression elements 36, 38 continue compressing tube 32, pumping fluid (milk) through the one-way valve 50 and into the collection container 60 until the compression element 38 reaches an end point in travel (typically before "bottoming out" against the anvil 2232). The end point in travel of the compression element 38 against portion 32L may be predetermined, or may be calculated on the fly by the controller 52 using feedback from pressure sensor 54 and feedback from the driver of the compression element 38, from which the controller 52 can calculate the relative position of the compression element 38 over the course of its travel. The compression member 36 remains closed throughout this process, as it is used to seal off the tube 32 the entire time that the compression element 38 is pumping milk out of the region 42 and into the collection container 60). As the compression elements 36, 38 reverse direction and pull away from the tube 32, they start the cycle again.

As milk enters the system, the suction level decreases (pressure increases). The feedback provided by pressure monitoring via pressure sensor 54 provides input to a feedback loop that adjusts the position of the compression member 38 to maintain the desired vacuum (pressure) within the tubing 32 by compensating for the changes in pressure that occur to changing amounts of milk in the tubing 32. For example, for a relatively larger amount of milk in the tubing, this will require a relatively shorter stroke of the compression member 38 toward anvil surface 2232 to achieve the latch pressure. This modification can be addressed by either slowing the movements of the compression member 38 to achieve the same timing cycle for pumping, or increasing the cycle frequency due to the less time taken for the shorter strokes of the compression member 38.

A contact pressure sensor 54 is shown in FIG. 4, wherein the pressure sensor 54 contacts the vacuum space (and, potentially, the milk) in the system 100. In this embodiment, a T-connector 370 is connected to the proximal end of the nipple receiving portion 112, so that both tube 32S and a tube 32P can be joined in fluid communication with the interior of the nipple receiving portion 112. In this way, pressure sensor 54 is placed in line, in fluid communication with the tube 32 and nipple receiving portion 112, and can measure pressure directly, as a result.

Alternatively, or additionally, one or more non-contact pressure sensors can be employed in the system 100. In the embodiment of FIG. 20, non-contact pressure sensor is located external of the tubing portion 32S. Various different types of non-contact pressure sensors can be used, such as optical sensors, magnetic sensors, linear variable differential transformer (LVDT) sensors, or the like. Further details about non-contact pressure sensors that may be employed in the present disclosure can be found in U.S. Provisional Application Ser. Nos. 62/053,095 and 62/027,685.

Figure 21D:
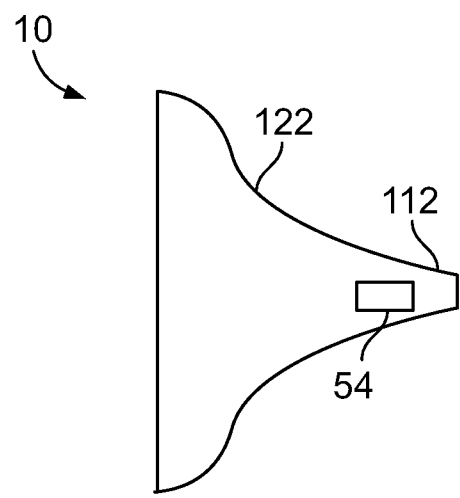
FIG. 21D shows a strain gauge mounted on or in a skin contact member according to an embodiment of the present disclosure.

FIGS. 21A-21B show a proximal perspective view and a side view, respectively, of skin contact member 10 according to an embodiment of the present disclosure, with four different potential locations for placement of a non-contact sensor 54. At location 350A, a thicker wall is provided relative to the thickness of the nipple receiving portion 112. In this example, the thickness of location 350A was 4.12 mm and the thickness of the nipple receiving portion 112 was 2.38 mm. At location 350B, a thinner wall is provided relative to the thickness of the nipple receiving portion 112. In this example, the thickness of location 350B was 1 mm and the thickness of the nipple receiving portion 112 was 2.38 mm. At location 350C, the thickness was the same as the rest of the nipple receiving portion, but protruding outwardly therefrom, see the cross-sectional view of FIG. 21C taken along line 21C-21C in FIG. 21A. The thickness at location 350D is the same as the thickness of the nipple receiving portion; in this example, 2.38 mm. It has been found that all locations 350A-350D will displace relative to vacuum changes within the system according to a linear relationship (although by different scaling factors, which can be determined empirically), see Example 1 below. Accordingly, a non-contact sensor 54 can be employed at any of locations 350A-350D to measure displacement changes in those locations. Pressure change measurements can then be calculated from the displacement change measurements, due to the linear relationship that exists between force applied to the locations 350A-350D and pressure within the system that causes the force. More generally, pressure changes in the system 100 can be measured by measuring opposition forces of any pre-loaded fluid contacting wall of the system 100.

Force versus displacement of a portion of the skin contact member 10, such as a portion of the nipple receiving member 112 also exhibits a linear relationship. Thus, displacement of a portion of the skin contact member 10 can be measured and pressure change can be calculated therefrom. Further, strain measurement can be used to calculate pressure changes. Therefore, attachment of a strain gauge 54 (see FIG. 21D) to skin contact member 10, typically on a region of nipple receiving member 112, can be used to measure strain changes in that region, which measurements can be used to calculate pressure changes within the nipple receiving member 112.

Use of a system 100 provided with a non-contact pressure sensor 54 would include loading the skin contact member 10 onto the main body/pump housing 34 (unless it has already been pre-loaded) and then turning on the pump power. As the pump system 100 goes through a power up routine, the controller 52 reads the force applied by the pressure sensor 54, position of the sensor 54 relative to the potentiometer when a displacement sensor 54 is used, or strain on the strain gauge when a strain gauge is used as the pressure sensor 54. This is the preload force applied by the sensor 54 to the wall of the nipple receiving portion 112 or tube 32, or position, or strain measured by the strain gauge, before the skin contact member 10 has been applied to the breast 2, so it is a state in which the pressure in tube 32 is atmospheric pressure. The controller 52 then calibrates the system such that the preload force or position or measured strain equates to atmospheric pressure. Based upon a look-up table or a best fit equation, the controller 52 can now convert any changes in force, position or strain read by the pressure sensor 54 against the wall of the nipple receiving portion 112 or tube 32 to pressure readings in the system 100 during operation of the breast pump system 100 upon attachment to the breast 2.

Figure 21E:
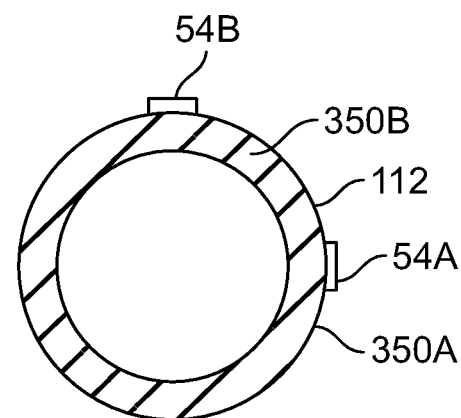
FIG. 21E shows a cross-sectional illustration of a nipple receiving portion in which a first non-contact sensor has been attached to a relatively thinner wall of the nipple receiving portion and a second non-contact sensor has been attached to a relatively thicker wall of the nipple receiving portion.
Figure 21F:
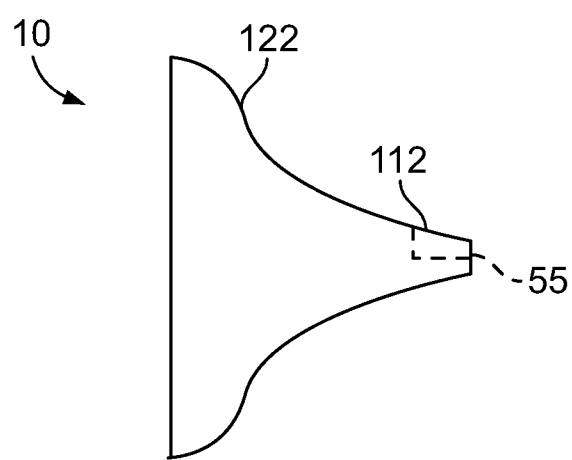
FIG. 21F shows a pressure sensor mounted on or in a skin contact member according to an embodiment of the present disclosure.

Optionally, the system 100 may be provided with two or more non-contact sensors 54 for determining pressure within the system 100. For example, by placing sensors 54 on different regions of the nipple receiving portion 112 that have different wall thicknesses, the linearity of the pressure changes measured by the sensors 54 on the different wall thicknesses will occur within different ranges of pressure (vacuum). FIG. 21E shows a cross-sectional illustration of nipple receiving portion 112 in which a first non-contact sensor 54 (see 54A) has been attached to a relatively thinner wall of the nipple receiving portion 112 and a second non-contact sensor 54 (see 54B) has been attached to a relatively thicker wall of the nipple receiving portion 112. The sensor 54B provides data for pressure change calculations at a higher range of vacuum pressures (lower pressures) than that provided by the sensor 54A. The vacuum ranges in which the sensors 54A, 54B provide accurate data (linear relationship) can be designed to overlap, so that the effective range of linearity and thus the range for accurately measuring changes in vacuum pressure can be extended. Furthermore, when the vacuum pressure measured is in the overlap region, where reliable data is provided by both sensors 54A and 54B, this can be used as a check on the accuracy of each of the sensors 54A, 54B, and/or used for calibration purposes. The present disclosure is not limited to the use of one or two sensors 54, as more than two sensors 54 may be applied in this manner, with or without overlapping pressure measurement ranges, preferably with overlap. FIG. 21F illustrates a pressure sensor 55 that may be employed to trigger or indicate when a predetermined vacuum pressure has been attained within the system. Pressure sensor 55 may be a switch that is in electrical communication with the controller 52. Pressure sensor 55 extends into the nipple receiving portion 112 (or, alternatively, tubing 32) at a predetermined distance from an inner wall of the nipple receiving portion 112/tubing 32 that has been calculated or empirically determined to be the distance that the inner wall deflects when the predetermined vacuum pressure has been attained in the nipple receiving portion 112/tubing 32. Accordingly, when the inner wall contacts the sensor 55 (as indicated by the dashed line in FIG. 21F), sensor 55 sends a signal to the controller 52 and the controller interprets the signal to indicate that the predetermined vacuum level has been reached. This type of sensor 55 could be used, for example, to indicate when maximum vacuum has been achieved. Alternatively, or additionally, sensor 55 could be provided to act as a safety mechanism, wherein the controller 52 would shut down the system if a signal is received from the sensor 55, as this would indicate that an abnormally high level of vacuum has been reached. For example, the system may be shut down if 350 mmHg vacuum is reached, or some other predetermined level of vacuum that is considered to be too much vacuum for safe operation.

To account for the possibility of degradation of pump tubing 32 and/or the skin contact member 10 over time the system can optionally be provided with an indicator that will alert the user when it is time to replace the skin contact member 10 and/or tubing 32. FIG. 22 shows an indicator 352 mounted on the inside of breast contact member 352 so that it can be readily viewed by a user prior to mounting the system 100 to the breast 2. Indicator 352 can measure a predetermined time/lifespan to change tube 32 and/or skin contact member 10 via a time based indicator, such as markings that fade or appear over time, other clocking mechanism that provides a visual and/or audible indication at the end of the measured time. In the event that the skin contact member 10 and/or tubing degrades over time, such as resulting from fatigue and/or oxidation, washing, etc., indicator 352 can track an average expected lifetime of the skin contact member 10 and/or tubing 32, and present a visible and/or audible indication to the user when it is time to replace the current skin contact member 10 and/or tubing with a new component. Average expected lifetimes of these components can be determined experimentally through testing, so that the average expected lifetime can be empirically calculated and programmed into the indicator. Changes in properties (e.g., elasticity, stiffness, etc.) of the tubing 32 and/or skin contact member 10 could result in inaccurate pressure readings, insufficient sealing of the skin contact member 10 to the breast 10 causing air and/or milk leakage, reduced pumping performance etc. Indicator 352 may be a time-based indicator, such as markings that fade or appear over time.

Figure 23:
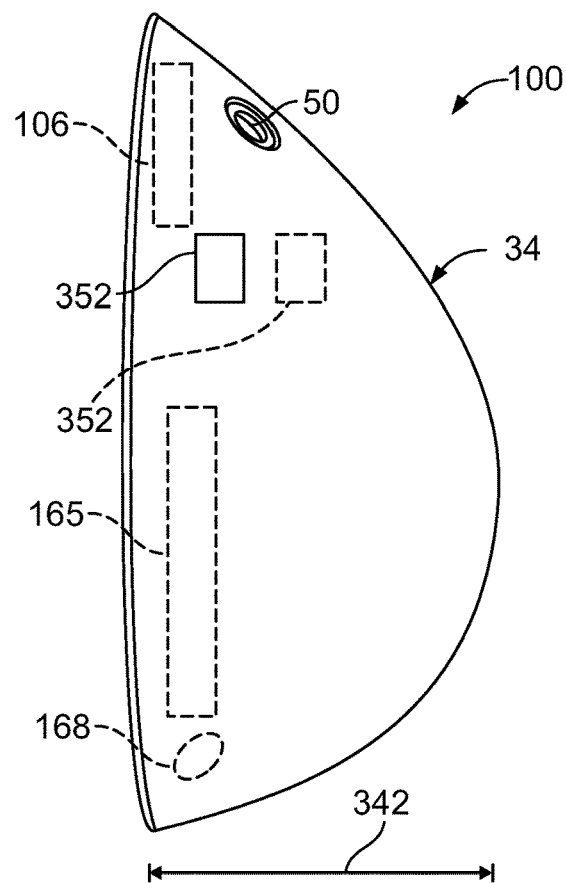
FIG. 23 illustrates another location in which an indicator may be placed, according to an embodiment of the present disclosure.

FIG. 23 illustrates another location in which indicator may be placed, in this case on the external shell 34 of the system 100. If the situation is that the time to replacement of the skin contact member 10 is different from the time to replacement of the tubing 32, and in which the embodiment has a skin contact member 10 that is configured to be separable from the tubing (some embodiments provide the skin contact member 10 and tubing 32 as an integral unit), then two indicators 352 may be provided, one set for a time to replacement of the skin contact member 10 and the other set to the time to replacement of the tubing.

Figure 24:
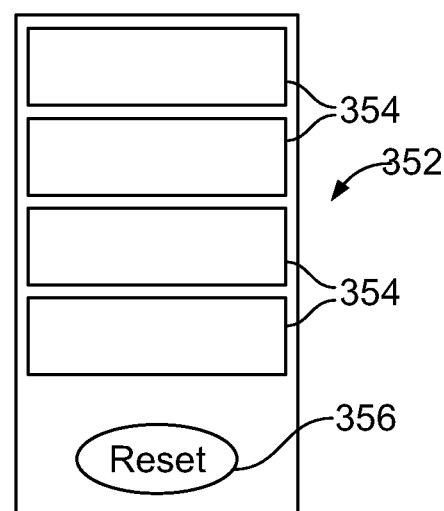
FIG. 24 illustrates an example of a reusable, time-based indicator that may be employed, according to an embodiment of the present disclosure.

Indicator 352 may be disposable, such as the type used on the skin contact member 10 as shown in FIG. 22 or on tubing 32, or may be reusable, where appropriate, such as those mounted on the external shell 34 as shown in FIG. 23 (although indicators 352 on shell 34 could also be made disposable and be removable from and replaceable on shell 34). FIG. 24 illustrates one example of a reusable, time-based indicator 352 that may be employed. In this embodiment, indicator 352 is provided with a plurality of LCD bars 354 that darken upon pressing and holding the reset button 356. Once the bars have darkened, a timer that is initiated, the timer having been programmed for the time to replacement of the skin contact member 10 and/or tubing 32. As shown in FIG. 24, the indicator has four bars 354, although more or fewer could be provided. For the four-bar embodiment, when one-quarter of the time to replacement has elapsed after the resetting of the bars, the top bar becomes clear, or lightens, so that only three bars remain visibly dark. Each bar sequentially lightens or clarifies after each successive passing of a quarter of the time to replacement, until all bars are clear when the time period expires. Thus, this type of indicator not only indicates when the full time to replacement has elapsed, but can also provide the user with an indication of approximately how much time is remaining until replacement is required, i.e., three dark bars indicates that ¾ of the use time still remains prior to the need to replace, etc.

Alternatively, or additionally, other types of indicators 352 may be provided, including, but not limited to: indicators that change with friction, interaction with moving parts, or the like. For example, a wear indicator 352 can be located anywhere on tubing 32, such as in a location where compression member 38 contacts tube 32L, where compression member 36 contacts tube 32S, or in another location such as where tubing 32 snaps into the pump housing/region 30. FIG. 26 shows a wear indictor located on tubing portion 32L. Wear indicator 352 may be placed anywhere on tubing 32 where wear is likely to occur. Wear, such as through friction resulting from interaction between tubing 32 and another component (compression member 36 or 38, pump housing 30, etc.) wears away a color of the indicator 352 as the wear occurs. Thus, when the color disappears or changes color, this indicates that it is time to change the tubing 32.

Likewise, a wear indicator 352 may be used on a component of skin contact member 10 in a location where it contacts the pump housing 30 when it is snapped into position. FIG. 27 illustrates a wear indicator 352 on skin contact member 10. Wear occurs as the skin contact member is attached to, and removed from the pump housing. Color change may be used to indicate when it is time to change the skin contact member, in a way that is described above.

Further alternatively, or additionally, the system 100 may detect tubing 32 wear. Controller 52 can track the position of the compression member 38 relative to tubing 32. FIG. 28 illustrates one example of an arrangement for tracking compression member 38 position, although the present disclosure is not limited to this arrangement, as alternative arrangements may be provided. In the embodiment of FIG. 28, driver 46 includes a motor 46M, a gear box 46G and an encoder 46E mounted to opposite ends of motor 46M. As motor 46M rotates, encoder 46E, which is fixed relative to the rotating motor shaft, rotates with the motor. An optical monitor 1146, such as an infrared laser or the like is beamed against the encoder 46E, such as the rotating blades of the encoder 46E cross the optical beam emitted by the optical monitor 1146 as the motor rotates. As the blades cross the beam, the beam is reflected back to a sensor 1148. By counting the reflections, the sensor 1148 and controller 52 can calculate the position of the motor 46M from a start position, and thus the position of the compression member 38 that it is driving, relative to a reference or starting position of the compression member 38. A similar arrangement can be provided for the driver 44 of compression member 36.

Thus controller 52 can keep track of the position of motor 46 and the position of compression member 38 relative to the tubing 32L. Since the controller 52 also tracks the pressure within tubing 32 via sensor 54 (e.g., as illustrated in FIG. 20), the controller 52 can correlate pressure changes developed in tubing 32 relative to position (and/or optionally, speed) of compression member 38. This correlation can be calculated when tubing 32 is new, i.e., upon initial use. Correlation calculations can be continually performed by controller 52 over subsequent uses of the system, and compared to the correlation values from the first use. The correlation comparisons will show a trend over the lifetime of the tubing 32 with subsequent uses. As the tubing 32 begins to wear out, less pressure change may be produced by the same change in position/speed of compression member 38 compared to when the tubing was new. This difference in pressure change can be tracked, and, when a predetermined amount of difference occurs, the controller 52 can send a warning to display 165 and/or external computer 470, that it is time to change the tubing 32. Also, by tracking the trend in usage of the system 100 over time and the rate of change of difference in pressure change resulting therefrom, the controller can estimate and predict when the time to change the tubing 32 will occur, and thus can send a warning to display 165 and/or external computer 470 at a predetermined time before the tubing 32 will need to be changed. For example, such a warning could be sent one week, one month, or some other predetermined time before it is actually time to change the tubing 32.

Figure 25:
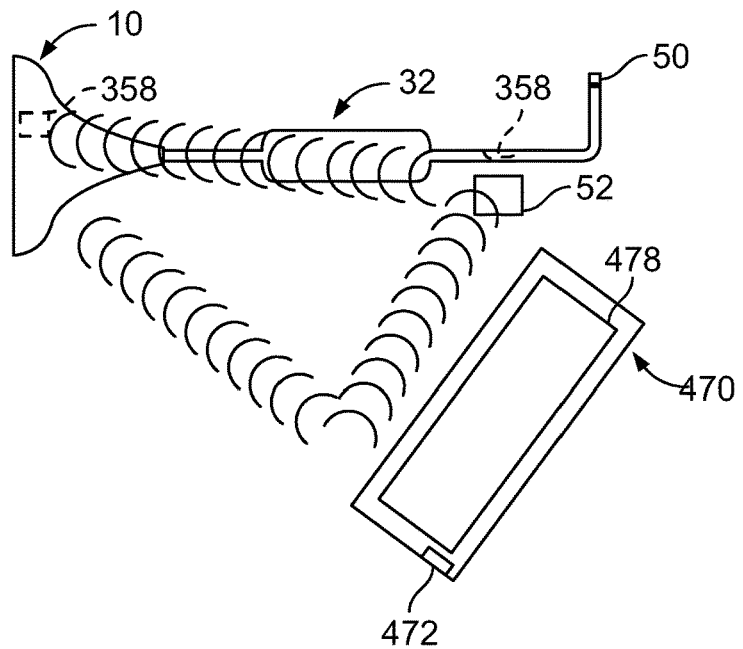
FIG. 25 illustrates tracking of a skin contact member and/or tubing by a controller of the system and/or an external computer, according to an embodiment of the present disclosure.

Further alternatively or additionally, usage of the skin contact member 10 and/or tubing 32 can be tracked by controller 52 and/or external computer 470 using a passive sensor 358 (see FIG. 25) via RFID or NFC, for example. One or more sensors 358, each provided with a unique identifier (ID) can be attached to or embedded into skin contact member 10 and or tubing 32. With each use of the system, this/these unique ID('s) can be identified by the controller 52 and/or external computer 470 to know that the skin contact member 10 and/or tubing 32 has been used, and the number of uses can thus be tracked, and/or times or use and/or cycle counts (number of cycles during use that the compression members 38 and/or 3 have executed). By tracking this data, the controller 52 and/or external computer can then indicate when it is time to change/replace the skin contact member 10 and/or tubing.

Further alternatively or additionally, the usage of the skin contact member 10 and/or tubing 32 can be tracked, such as by using radio-frequency identification (RFID) or near field communication (NFC) tracking. This tracking can be carried out, for example, by embedding a passive sensor/chip 358 configured to RFID or NFC tracking into one or both of the skin contact member 10 and tubing 32, see FIG. 25. The one or more chips 358 can be identified by the controller 52 of the pumping system 100 (by hard wire and/or wirelessly, preferably wirelessly) by an external computer 470, which may be, but is not limited to: a smartphone, a tablet computer, a laptop computer, a notebook computer or a server. The controller 52 and/or external computer 470 communicates with the passive sensor(s)/chip(s) 358 which indicate(s) when the system is in use. By tracking the times of use and/or number of uses, or even pump cycle counts, the controller 52, or external computer can alert the user when it is time to change the skin contact member 10 and/or tube 32. Alerts may be audible and or visual, such as a beep or voice message emitted from the external computer 470 via speaker 472 and/or a visual alert such as text and/or graphics displayed on display 478, or by the controller 52, via optional display 165 and/or optional speaker 168. The tracking provided by the passive sensors 358 provide the ability to assign a unique identifier to each component that a sensor 358 is attached to or embedded in. Thus, the controller 52 and/or external computer 470 can readily distinguish between each skin contact member 10 and tube 32 used.

This same technology can be provided with the milk collection containers 60, so that tracking of extraction date and time, volume extracted, etc. can be recorded and stored with regard to each milk collection container used with the system 100 to extract milk. Thus, the system 100 can register individual milk collection containers 60, so that the user can readily identify when milk in each container 60 was collected, the volume in each container 60, etc. The breast pump system can record the volume of milk in any given container 60 during a pumping session. The data recorded can be sent to an external computer 470 and/or over the Internet, either automatically or manually.

There are multiple ways to link data to a particular milk collection container 60. Containers 60 may be provided with easily identifiable marking 60M (see FIG. 37), such as alphanumeric markings (letters, numbers) of other markings that are readily identifiable and distinguishable from one another. Additionally or alternatively, marking 60M on each container 60 can include a barcode, QR code, RFID, NFC, other magnetic or electromagnetic identifier, or the like pre-printed on the container 60. When initiating a milk pumping session using system 100 with milk collection container 60 mounted thereto, or at the end of the session or anytime in between, the user can scan the mark with a scanner on an external computer 470 (smartphone or the like), or scan using the system 100 itself in embodiments where controller 52 is provided with a scanner 101 on the system 100 as illustrated in FIG. 1, or manually input the identifier of the mark 60M if no barcode is used, and thus link the particular milk collection container with the mark 60M in the database on the external computer. At the end of the milk extraction system, when data is exported to the external computer 470 and/or Internet/cloud-based database, the data, such as volume, extraction date and time, etc. are exported along with the identifier of the mark 60M so the data is linked and stored relative to the identifier for that particular milk collection container 60.

The mark 60M when in range of the controller 52 and/or external computer 470 may automatically activate the system 100 for a pumping session, or activate an activatable feature of the system, such as a power switch that can be operated by the user to initiate a pumping session. If a container 60 contains a mark 60M that is not recognizable by the controller 52 and or external computer 470, or contains no mark 60M at all, then the system 100 may be configured so as to be prevented from operating for a milk extraction session, as no unique ID has been recognized in this instance. By ensuring that a milk collection container 60 used has a recognizable, unique ID, this can provided additional assurances for safety, sterility and quality of the milk collection container 60 used. The presence of the unique identifier 60M allows the system 100 to track when the milk collection container 60 enters into proximity with the system 100 for use in an extraction session, when it leaves the proximity at the end of the session, as well as other data already described, such as volume of milk extracted, date and time of extraction, length of extraction session, etc. These information capabilities can be useful for managing personal use and consumption by the user's baby, as well as for milk donation services, where milk extracted from one mother may be donated to a milk bank, or to a baby having a different mother. With regard to milk donation services, a collection bank can scan the milk collection container 60 into the bank database using the same unique identifier provided by the mark 60M and confirm that this is a container 60 that is qualified for the program. In embodiments where container 60 includes the one-way valve 50, this provides further assurance that no milk has been removed from the container 60 prior to it arriving at the milk collection bank.

The controller 52 and/or external computer 470 may be provided with memory storing a database of registered unique ID's which can be regularly updated by communication with a central database through a network (either wirelessly or by wire) such as the Internet. Alternatively, controller 52 and/or external computer may connect with the central database, such as by WiFi or other wireless connection to the Internet, or even by Ethernet connection.

As already noted milk collection container 60 may be provided with a passive sensor 358, such as an RFID or NFC chip (see also FIG. 34), which may either be attached thereto or embedded therein, which can be used to link the milk collection container 60 to all data recorded in regard to it.

As an alternative to pre-marked collection containers 60, a user could manually mark the containers 60 with unique identifiers and manually enter these identifiers into the external computer. Alternatively, the manual marks could be scanned into the external computer.

The system 100 can calculate the volume of milk pumped into milk collection container 60. By knowing the dimensions of the tubing 32 downstream of the compression member 36 when compression member 36 has sealed off tubing portion 32S, the overall volume capacity of the system 100 downstream of compression member 36 can be calculated. Tracking of the position of the compression member 38 relative to the tube 32 (such as by knowing the driver 46 position at all times, for example), dictates the volume change in the tubing 32. As the pumping process is carried out, pumping/purging of milk into the milk collection container occurs when the compression member 36 has closed off the small tube portion 32S at the location of compression. When the compression member 36 has closed off tube portion 32S, the change in position of compression member 38 that occurs to carry out the purge of milk from the tubing 32 and into the milk collection container 60 can be used to calculate the change in volume of the tubing 32 downstream of the compression member 36, which equates with volume of milk that is pushed into the milk collection container 60 bag through the one way valve 50.

Optionally, an estimation of the percentage of milk and air in the system tubing 32 can be calculated based on a compliance assessment of the tubing 32, such as at tubing portion 32L. The more air in the tubing relative to milk, the more the tube portion 32L will move for a given force thereagainst by compression member 38L or a given pressure change. This relationship can be mapped, for example, to provide a look up table to identify the percentage of air and percentage of milk in the tube 32 before purging. Then, knowing the volume that has been purged by knowing the travel of the compression member 38 during the purge, the volume of milk and the volume of air can be calculated.

Further optionally, the opening of the valve 50 can be monitored or the movement of fluid past the valve 50 can be monitored. By knowing the crack pressure of the valve 50 and knowing the pressure within the tubing 32, this can identify when a purge actually pushes through (i.e., when pressure in tube 32 reaches the crack pressure). This can increase the accuracy of the calculated purge volume by beginning the volume calculation at the position of the compression member at the time that the crack pressure is reached.

In addition to calculating the volume of milk purged with each purge cycle, the system (via controller 52) can sum the volumes from all purge cycles to calculate the total volume pushed into the milk collection container 60 during a milk extraction session. This volume can be stored with a unique identifier provided to the milk container so that the system 100 keeps a record of how much milk is stored in each milk collection container 60. This information can also be time stamped so that the user will know the time and date that milk was collected, regarding each milk collection container. Additional statistics can be calculated, including, but not limited to: average volume per extraction session, total volume extracted for any given day, average milk extraction volume per day, etc. Any and all of this data can be exported to an external computer, either manually, or it may be automatically uploaded to the computer 470 when the computer 470 is within range of the system 100 for wireless communication, or when the computer 470 is connected to the system by wire. Further optionally, any or all of this data can be either manually or automatically uploaded to a cloud service over the Internet, either wirelessly or by wire.

When calculating milk volume pumped from the system 100, there is a need to distinguish between any air pumped by the system versus milk pumped from the system, as well as pumping mixtures of milk and air. When initiating a milk pumping/extraction session, there is air in the tubing 32 this initial volume of air needs to be pumped into the milk collection container 60 to prime the pumping system 100. Distinction between pumping air versus pumping milk can be recognized by correlating pressure changes with the amount of movement of compression member 38 needed to establish the pressure changes. For example, when air is in the tubing, a greater change in position, or more overall travel of the compression member 38 is need to establish the same pressure change than that needed when the tubing 32 is filled with milk. Thus, relatively more motion of the compression member with relatively less pressure change indicates air in the tubing 32. This difference in pressure may also be detected when the compression member 36 is open (i.e., not closing off tube portion 32S) and compression member 38 is retracting and this increasing the vacuum pressure.

FIGS. 31A-31B schematically illustrate breast pump systems 100, according to alternative embodiments of the present disclosure, in which the external shell 34 of the system does not need to be continuously curved, but, instead can have another shape, such as geometrical (all or a portion of which is non-curved) or even irregular or some other custom shape designed to conserve space. In the embodiment of FIG. 31A, shell 34 has substantially flat surfaces that form an angular external surface. These surfaces can more closely contour the internal components of the system than that provided by a continuously convex external shell 34, and thereby eliminate spaces that are devoid of components in a system with a continuously convex external shell 34. In the embodiment of FIG. 32B, external shell has a flat central portion, similar to the embodiment of FIG. 31A, but has convex portions extending radially from the flat central portion. It is noted that these are two non-limiting shapes provided, as the shape of external shell can take on almost any shape that is well suited to receiving the internal components of the system 100, while eliminating as much void space as possible. Milk collection container 60 is mountable over the external shell 34. The milk collection container 60 can be formed so as to have variable volume when filled, so as to conform to the external surface of the external shell, while providing a convex shape externally, so as to mimic the shape of the breast 2. As shown in FIG. 31A, the peripheral portions of the container 60 are thinner when filled than the central portion of the container 60 when filled. In FIG. 31B, the container is pre-shaped to follow the contours of the external shell 34 when filled, including bulbous portions 34B that conform to the concave portions of the external shell 34. These solutions provide for a more compact overall system, while at the same time maintaining the appearance of the system 100 when worn to resemble that of the natural breast. The external surface 60E of the milk collection bag 60 can be formed so as to maintain a continuously convex appearance even when the milk collection bag is empty. The milk collection bag 60 may have a rigid inner surface that mates with the contours of the external shell 34 and a soft, flexible external surface that inflates/moves as milk enters the bag 60, while maintaining a convex/naturally appearing breast shape. Alternatively, the exterior surface of the milk collection bag 60 may be rigid to maintain breast/convex shape and the inner surface may be soft and flexible to match the contours of the external shell 34, as the bag 60 expands while it fills up with milk. Another option is for both surfaces to be rigid and yet allow some motion as the space/bladder in between fills with milk, allowing the surfaces to move apart as needed to accommodate the volume of milk received.

FIGS. 32A-32B illustrate a milk collection container 60 for use in system 100 according to another embodiment of the present disclosure. In this embodiment, container 60 has a preformed convex surface 60C that is shaped to mimic the natural appearance of the breast 2. Surface 60c may be pre-formed such as by molding or the like, and maintains the convex shape shown, even when the container is empty, as well as when it contains milk. When mounted on the system housing 34 the convex shape 30 provides the appearance of a natural breast, with or without containment by a bra. The opposite surface 60F of the container 60 is flexible and may even contain wrinkles or folds 60W when container 60 is empty. As the container 60 fills with milk, the container 60 expands by moving the flexible surface outwardly. During the outward movement of the flexible surface 60W, the flexibility of this surface allows it to conform to the shape of the system housing/external shell 34 to maximize conservation of space of the entire system 100. FIG. 32A illustrates in dashed lines the shape of the flexible surface 60W when is moved to contour to the external shell 34 of the embodiment of FIG. 31A. FIG. 32B illustrates in dashed lines the shape of the flexible surface 60W when is moved to contour to the external shell 34 of the embodiment of FIG. 31B.

In addition or alternative to the flexible surface provided 60F provided with a pre-shaped surface 60C, milk collection container may be further be provided with one or more structural elements, 76, such as baffles, heat seals, struts or other restrictions that restrict the amount of expansion of flexible surface 60F relative to contoured surface 60C and or provide shape to the collection container 60 even when empty. FIG. 33 shows container 60 having baffles 76 that internally connect to the internal walls of portions 60F, 60C to limit the amount of expansion in the areas where the baffles 76 are located, relative to the amount of expansion that the remaining areas can experience. Baffles 76 can be provided in any pattern desired so as to customize the expanded contours of the flexible surface 60F to conform to a particular contour of an external shell 34.

FIG. 32C illustrates a milk collection container 60 that is formed so that the distal surface 60D of the container, when filled with milk has a shape that matches the proximal surface contour of the external shell 34. The proximal surface 60C may be flexible or pre-formed with the convex shape that mimics the appearance of the breast 2.

Even in embodiments of the breast pump system 100 wherein the external shell is convex, the milk collection container 60 used therewith with have varying levels of thickness from top to bottom and side to side when milk is collected into the container 60 while mounted on the system. Accordingly the container 60 can be pre-shaped or preconfigured to take on a shape having varying thicknesses between the rear and front walls when containing milk.

FIG. 34 illustrates a milk collection container 60 that includes a passive sensor 358 that can be either attached to or embedded in the container 60. Sensor 358 may be an RFID or NFC device, or the like that contains a unique identifier (ID) is created in a manner that is recognizable to controller 52 and/or external computer 470. The controller 52 and/or external computer are provided with a reading application that can wirelessly read the unique ID when the container 60 that includes the sensor 358 having the unique ID is brought into close proximity with the controller 52, such as by mounting the collection container 60 to the external shell 34. Once read, this unique ID is then referenced by the controller 52 and/or external computer 470 into a database application that contains detailed information as to what the sensor 358 is attached to. Upon confirming the specific collection container that the sensor 358 is attached to/embedded in, the system 100 can then track usages of that specific container, including, but no limited to: volume of milk collected, date and time of collection, duration of extraction session, etc. Optionally, if a collection container 60 does not include a sensor 358 with a unique ID that is recognizable to the system 100, then the system will not operate with that collection container.

FIG. 35 illustrates a milk collection container 60 wherein the connector 62 contains one-way valve 50, according to an embodiment of the present disclosure. With this embodiment, the external shell 34 or tubing 32 would not be provided with the one-way valve 50, but would be provided with a mating connector to connect to connector 62 containing the one-way valve. Whether one-way valve 50 is provided with the connector 62/collection container 60 or provided at the end of tubing 32, the mating connector for connecting to connector 62 can otherwise be the same. Examples of mating connector arrangements can be found, for example in Provisional Application Ser. No. 62/027,685. Other examples of connector types that can be used for connector 62 and mating connector include, but are not limited to: bayonet-type, threaded connectors, compression fittings, flared fittings, etc.

FIG. 36 illustrates a milk collection container 60 according to another embodiment of the present disclosure. In this embodiment, tubing 32 is made integral with the milk collection container 60 and one-way valve 50 as shown. The open end of tubing 32 is provided with a connector 62 configured to mate with connector 134 of skin contact member 10.

Figure 38:
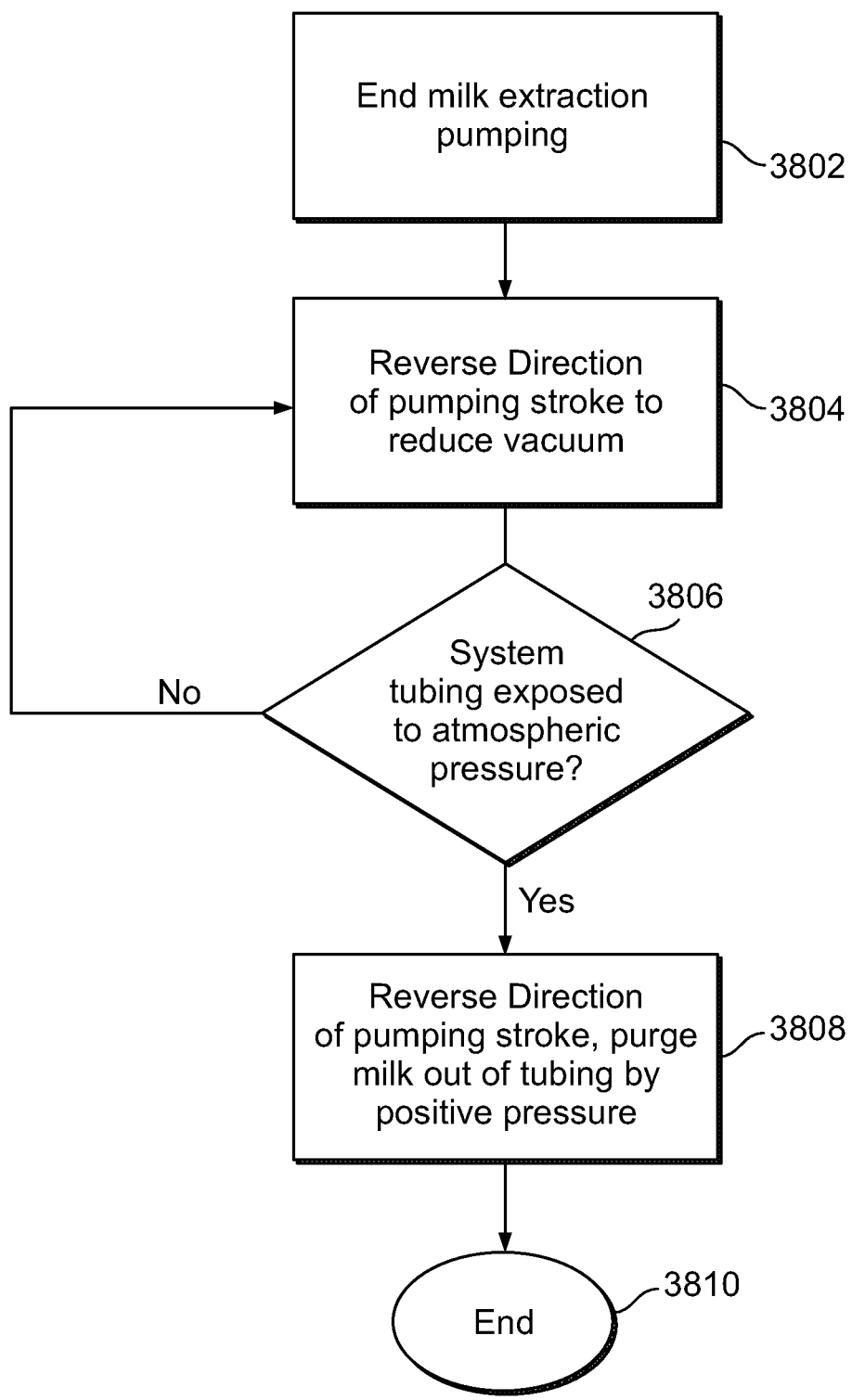
FIG. 38 illustrates events that may be carried out to perform a purge according to an embodiment of the present disclosure.

When a user has completed the pumping phase of extracting milk from a breast 2, it is useful and efficient to purge as much milk that remains in the tubing 32 from the tubing 32 and into the milk collection container 60. FIG. 38 illustrates events that may be carried out to perform a purge according to an embodiment of the present disclosure. At event 3802 the system 100 ends the pumping cycle having been carried out during the extraction phase. Ending of the extraction phase can be performed upon elapse of a predetermined extraction phase time, calculation of a predetermined amount of milk having been pumped, manual cessation of the extraction phase by the operator, or some other predetermined value having been achieved after performing the extraction. At event 3804 the direction of the pumping stroke of compression member 38 is reversed and the compression member 38 is run in the reverse direction to decrease suction within the tubing 32 and optionally create a small positive pressure within the tubing 32 to facilitate removal of the system 100 from the breast 2. Alternatively, the suction may be decreased to a level where a slight suction remains so that the user still pulls the system 100 of the breast 2 to detach it. Preferably the vacuum is reduced to 0 mmHg, or a slightly positive pressure to automatically detach the system 100 from the breast 2. The end pressure value where the pressure reduction by reverse pumping is ceased can be in the range of about −20 mmHG (weak vacuum) to a positive 50 mmHg (e.g., the crack pressure of the valve 50). The compression member 36 does not close off the tubing portion 32S during this process, rather, tubing portion 32S remains open. Initiation of this reverse pumping may occur automatically after executing event 3802 or, alternatively, may be initiated by the user actuating a purge actuator on the optional control panel 166 provided on the system 100 (see FIG. 23). This process continues until the seal of the system 100 to the breast 2 is broken, which is detected by the controller 52 via sensor 54 at event 3806. Once exposure of the tubing 32 to atmospheric pressure is detected at event 3806, the stroke direction of pumping is again reversed thereby pumping the milk in tubing 32 under positive pressure and driving the milk from the tubing 32 into the container 60 at event 3808. At event 3810 the purge process ends. Event 3810 can occur at some predetermined time after initiation of event 3808, or can be initiated by measuring the compliance of tubing portion 32L and executing event 3808 when the compliance of tubing portion 32L indicates that the contents in tubing portion 32L have a least a predetermined percentage of air therein (such as 90% 95%, 97% or some other predetermined percentage). If by chance, the system 100 accidentally or otherwise becomes resealed to the breast 2 during purge pumping, the system 100 can automatically shut down as it senses vacuum pressure being regenerated in the vicinity of the breast 2/skin contact member 10.

FIGS. 39A-39B illustrate various arrangements that may be provided to the system 100 to help prevent loss of milk out of the system upon detachment of the system 100 from the breast 2. These arrangements can be provided in embodiments that are configured to execute a purge operation in a manner described with regard to FIG. 38 above, but can also be provided in systems 100 that used different purge techniques other than that described with regard to FIG. 38.

A weak valve 390, such as a flap valve of the like can be provided in small tube portion 32S, near where it connects to the skin contact member 10, as illustrated in FIGS. 39A-39B. Valve 390 is very flexible so that it opens in a first direction (upwardly as shown in FIGS. 39A-39B) when vacuum is generated in tubing 32. A very small amount of vacuum (much less than latch vacuum, for example about 5-15 mmHg) is sufficient to open the valve 390 in the upward direction, see 390A. The valve 390 is sufficiently stiff to remain closed under a positive pressure equal to the hydrostatic pressure generated when the tubing 32 is completely filled with milk. A positive pressure that is generated which is above this hydrostatic pressure by a predetermined amount (e.g., 5-15 mmHg positive pressure greater than the positive pressure generated by a full column of milk) forces the valve 390 open in the opposite direction, see 390B (i.e., downwardly, as illustrated in FIGS. 39A-39B). With this arrangement, the breast pump system 100 can be unsealed and detached from the breast 2 after extracting milk therefrom and the milk remaining in the tubing 32 will be prevented from escaping out of the skin contact member 10 by the closed valve 390. The system 100 can then be run in a forward stroke motion to generate positive pressure using compression member 38 to drive the milk from the tubing 32 and into the milk collection container 60.

Additionally or alternatively, a valve or flap may be provided to extend radially inwardly from the bottom portion of the breast contact member 122 as shown in FIG. 39A. When the breast 2 is inserted into the breast contact member 122 for carrying out an extraction session, the breast 2 folds down the flap/valve 522 against the inner wall of the breast contact member 122, see 522-2, When the breast 2 is removed from the breast contact member 122, the flap/valve 522 resiliently returns to is its unbiased position (see 522-1), where it extends radially inwardly and thereby retains milk within the breast contact member 122 that would otherwise have spilled out of the system. By tipping the breast contact member 122 up, the user can cause the milk in the breast contact member 122 to flow into the nipple receiving portion 112 under gravity, where it can be pumped into and through the tubing 32 to be purged into the milk collection container. Further alternatively, flap 522 may be provided with a tacky surface that contacts the breast 2 so as to assist in providing tension to the breast 2 to control the amount of breast tissue that enters the nipple receiving portion 112, similar to the function of the tacky regions 360 described above. Further optionally or additionally, the stiffness or strength of the valve/flap 522 can be such that the breast contact member 10 has to be pressed against the breast 2 to deflect the valve/flap 522, which thereby establishes tension. Still further, flap 522 can be provide at both top and bottom locations of the breast contact member 122 (rather than just at the bottom as shown in FIG. 39A), or at other locations intermediate the top and bottom, or could be formed continuously around the entire perimeter of the breast contact member 122.

FIGS. 40A-40B illustrate two different cross-sectional views of a contour element 410 provided with a breast pump system 100. Contour element 410 extends distally from the distal perimeter 34D of the external shell 34 and proximally extends over the distal portion of external shell 34 to provide a contoured extension of the external shell that provides a visually more appealing appearance the more closely mimics the natural appearance of a breast 2 supported by a bra. The contour element 410 tapers distally to form a smoother transition with the breast 2 when the system 100 is mounted on the breast 2, thereby making the system 100 less visible or noticeable when worn by a user. The contour member 410 can be configured to snap around the circumference of the main body 34 of system 100 or form a friction fit therewith, for example.

Figure 41A:
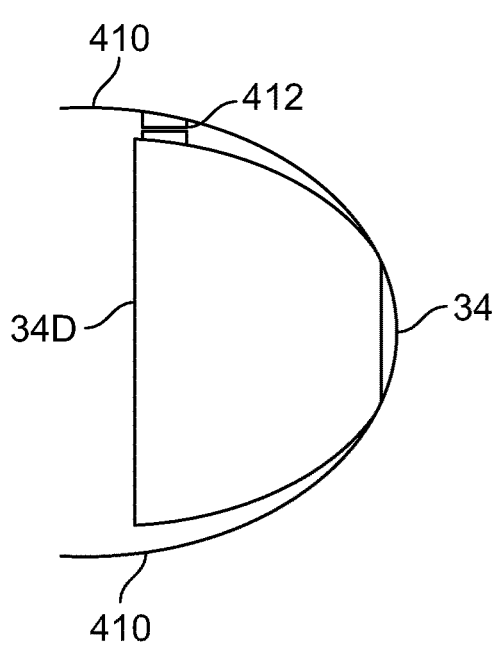
FIG. 41A illustrates a single thin layer of plastic or fabric used as a contour element, according to an embodiment of the present disclosure.
Figure 41B:
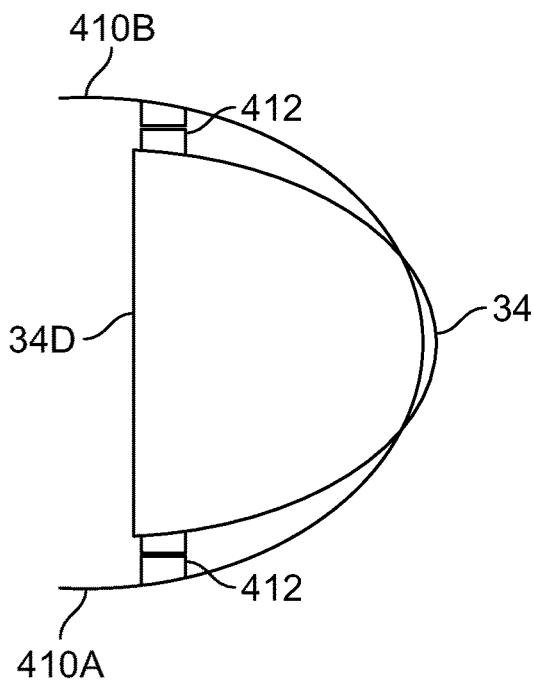
FIG. 41B illustrates a single thin layer of plastic or fabric used as a contour element, according to an embodiment of the present disclosure.

FIG. 40A shows a cross-sectional view illustrating the upper and lower portions of the contour element 410. FIG. 40B shows that contour element on the left and right sides of the external shell 34. The embodiment shown in FIG. 40B is for the right breast. A contour element for the left breast would be a mirror image of that shown in FIG. 40B, as, in both cases, the contour element 410 has a lateral portion 410A that extends further distally from perimeter 34D than the distance that medial portion 410B extends distally from the perimeter 34D. The lateral portions of the systems 100 are contoured more by the contour element 410 then are the medial portions, as the medial portions are where the cleavage of the breasts is formed, so deviation from the natural appearance is less visible on the medial sides. Further, the medial extensions are less as there is less space to extend into. Additionally, the contour element 410 may extend over a portion of the proximal end portion of the external shell 34 to provide additional "flatness" to the proximal end of the system 100 to make it appear more like a natural breast 2 as opposed to a more pointy "ice cream scoop" shape, Although the sections of component 410 in FIGS. 40A-40B are illustrated as solid material in FIGS. 40A-40B, such as being made of foam, plastic, or other lightweight material, they could alternatively be made hollow, or even made of one layer of material to provide the same contouring shapes. Thus a single thin layer of plastic or fabric could be alternatively used, for example as illustrated in FIGS. 41A-41B. The material of the contour element 410 may be resilient so that if it is depressed or distorted, it will naturally spring back to a contour that appears natural.

Figure 42:
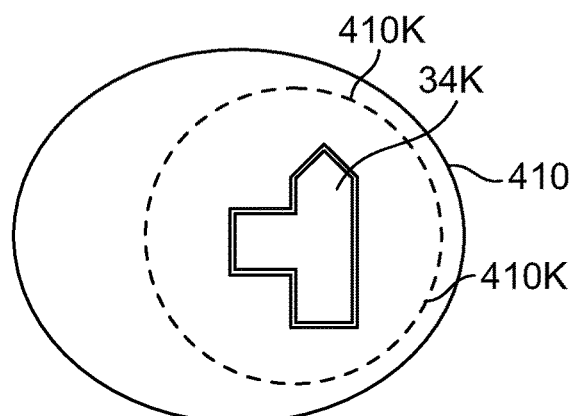
FIG. 42 illustrates a contour element fitted on an external shell in which the external shell is provided with a key that ensures that the contour element is properly oriented on the external shell each time the two components are mated, according to an embodiment of the present disclosure.

Attachment members 412 such as snaps, hook-and-loop type fasteners, buttons, magnets or other attachment members may be provided on one, or preferably more than on locations of the external shell 34 and internal surface(s) of the contour element 410 to ensure securement of the contour element 410 relative to the external shell, and to ensure that the proper orientation of the contour element 410 relative to the external shell 34 is achieved each time they are connected, so as to provide the desired appearance, FIG. 42 illustrates an embodiment of a contour element 410 fitted on an external shell 34 in which the external shell 34 is provided with a key 34K that ensures that the contour element 410 is properly oriented on the external shell 34 each time the two components are mated. The contour element 410 has a mating key 410K that mates with key 34K and ensures that the contour element 410 position relative to the external shell 34 does not rotationally vary nor does it vary superiorly, inferiorly, laterally or medially, but rather is positioned substantially exactly the same relative to the external shell 34 each time it is mounted thereover. As shown, the key 34K extends from the surrounding surface of the external shell 34K and the mating key 410K is an opening in the contour element 410 that mates to the mating key 34K. Alternatively key 34K could be formed as a depression in the external shell 34 and mating key 410K could be a ridge extending inwardly (or a solid shape extending inwardly) from the surrounding inner surface of the contour element 410 and shaped to mate with key 34K. It is further noted that the shapes of the key 34K and mating key 410 are not limited to those shown, but could be any shape that ensures that the contour element 410 can be mounted to the external shell 34 in one orientation and position. Further, the key 34K and mating key 410K do not need to be centrally located, but could be at any location on the external shell 34 (and corresponding location of contour element 410). Also, multiple keys 34K and mating keys 410K could be provided at multiple locations.

Figure 43:
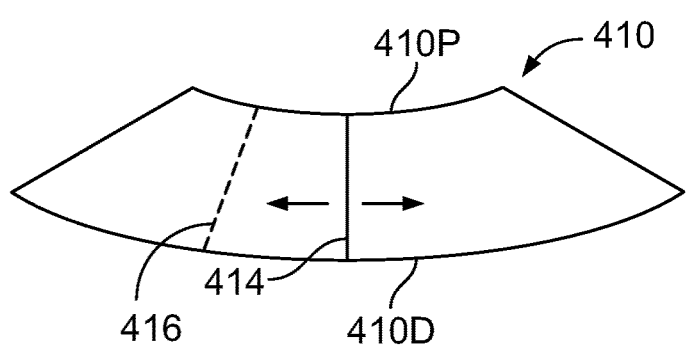
FIG. 43 illustrates a contour element in which a first edge of the contour element overlaps a second edge, and can be adjusted to reduce, increase or maintain the circumference of the distal perimeter, while at the same time reducing, increasing or maintaining the proximal perimeter, according to an embodiment of the present disclosure.

The contour element can be adjustable, so that it can be adjusted for a best fit relative to the breast 2, and so that it can be fitted to different sizes and shapes of breasts 2 and still provided a more natural appearance in each case. FIG. 43 illustrates an embodiment of contour element in which a first edge 414 of the contour element 410 overlaps a second edge 416, and can be adjusted to reduce, increase or maintain the circumference of the distal perimeter 410D, while at the same time reducing, increasing or maintaining the proximal perimeter 410P. After adjustment, the first edge 414 can be fixed to the underlying surface of the contour element 410 that it overlies, such as by use of hook-and-loop type fasteners, snaps, adhesive, or the like. The contour element can be further tailored for a better fit, if needed, but cutting away all or a portion of the distal perimeter 410D to a length desired, so as to adjust the length by which the contour element 410 extends from the distal perimeter 34D on the top, bottom and sides of the device. All of these distances can be tailored to be as needed.

FIG. 44 illustrates an embodiment of contouring element 410 provided with predetermined markings that may be provided to assist the user in adjusting the contouring element 410 to better contour to the breast 2 that it is to be used on. For example, markings 418, 420, 422 and 424 can be provided as suggested starting locations for placement of the edge 414 overlapping edge 416 and placed at the appropriate marking for D cup, C cup, B cup and A cup sizing, respectively. Markings 426, 428 and 430 are suggested locations to cut away the distal edge 410D to fit 36", 34" and 32" breasts 2, respectively.

FIG. 45A illustrates an embodiment in which external shell 334 is provided with two keys 34K1 and 34K2. The contour element of FIG. 45B is provided with mating keys 410K1A and 410K2 that are configured to mate with keys 34K1 and 34K2, respectively, when the contour element 410 is in a first sizing configuration. Additional mating keys 410K1B and 410K1C are provided to mate with key 34K1 when the contouring element 410 is adjusted in a manner described above to better contour with smaller size breasts 2. Although two additional mating keys 410K1 and 410K2 are shown, more or fewer can be provided where more or less adjustability is needed. Likewise, additional mating keys could be provided for 410K2, in addition to, or alternative to the provision of multiple mating keys 410K1.

FIGS. 46A-46B illustrate a contour element 410 according to another embodiment of the present disclosure. In this embodiment, contour element 410 is made of an easily compressible material such as a light, resilient foam that readily conforms to the shapes of objects that it is compressed against. In the embodiment shown, the contour element 410 is a substantially straight plate-shaped element that tapers at its ends, but other shapes could be employed. The center portion of the contour element 410 can be attached to the external shell 34 as shown in FIG. 46A, using any of the connectors, adhesives or the like described previously. When the system 100 is supported by a bra 440 as shown in FIG. 46B, the contour element 410 contours to the external shell 34 of the system, and also contours to the bra 440, thereby providing a natural breast shaped appearance. Further alternatively, the contour element 410 of FIG. 46A could be made thinner and would not be required to contour to the external shell 34, as the bra 440 provides a contouring shape.

The system 100 can be configured to distinguish whether it has been attached to the left breast 2 or the right breast 2 of the user. This can be useful for tracking milk volume output per breast, per session, total daily volume per breast, etc. When using two of the pump systems, the tracking of data for each breast can still be maintained accurately, even when one of the pump systems 100 is attached to the left breast during a current pumping session after having been attached to the right breast during a previous pumping session. In one embodiment, the pumping systems 100 can establish current location (i.e., left or right breast) by receiving a signal from the other pumping system having been attached to the other breast 2. This established relative left-right locations of the two pumping systems 100, so that each system 100 can accurately record as to whether milk is being extracted from the right breast 2 or left breast 2. This identification is automatic, without any user input required and it also relieves the burden on the user to otherwise keep track of which pump system 100 is placed on each breast and to maintain this order with each successive pumping session.

An orientation signal, such as by Wi-Fi, BLUETOOTH, BLUETOOTH Low Energy (BTLE), RFID, NFC or the like may be used to automatically determine which pump 100 is on which breast 2. One or more magnetic coils 450 may optionally be provided in each pump system 100 (e.g., see FIG. 23) such that the relative positions of the pump systems 100 can be determined to each other by the signal, akin to the way that surgical tracking is performed with coil magnetic sensors. By placing magnetic coils on the left and right sides of the pump systems 100, and running a small current through the coil 450 in one of the pump systems 100, the current induces a signal in the coil 450 in the other pump system 100. The signal strength is low and is only induced when the breast pump systems are close together, such as when mounted on adjacent breasts 2. This signal can be used to determine the relative locations of the pump systems 100, i.e., which system 100 is mounted on the left breast 2 and which system 100 is mounted on the right breast 2.

The system 100 can calculate the pressure during operation in any of the manners described above. The suction (pressure) level can be varied as desired, and by continuously or repeatedly measuring/calculating pressure, the feedback provided by sensor(s) 54 to controller 52 provides a control loop that can be used to adjust the compression member 38 position and/or speed to vary the suction pressure to a level desired, or maintain a desired suction pressure. Thus, controller 52 can control the positions and speeds of compression members 36, 38 to achieve any vacuum pressure pumping profile desired, and provide automatic, real time adjustments to maintain a desired vacuum pressure within the system.

The controller 52 tracks the position of the compression member 38 relative to the tubing 32L, such as by keeping track of the driver 46 position or shaft position (interconnecting linkage between driver 46 and compression member 38), and calculates (or looks up) pressure based upon data received from sensor 54. Thus, changes in position and/or speed of the compression member 38 by controller 52 can be controlled by resulting changes in pressure calculated or looked up, relative to the pressure sought to be achieved. Controller 52 can control compression member 36 in a similar manner, but control of member 36 is more focused on position control, as the compression member 36 needs to fully close off tube portion 32S when maintaining latch suction against the breast 2/nipple 3. However, the closing off is timed and performed at the determined latch pressure, which is known from the data received from sensor 54.

During extraction, the compression member 38 cycles between latch suction and maximum suction to extract milk from the breast 2. The suction level of the maximum suction can optionally be adjusted to the comfort of the user, anywhere between latch suction pressure to a maximally allowed suction pressure, such as −250 mmHg or some other predetermined maximally allowed suction pressure. As the tubing 32 receives more and more milk volume, the compression member moves farther and farther in the direction away from tube portion 32L to achieve/maintain maximum suction. As the compression member 38 begins to near its position limit away from the tube portion 32L (near the fully uncompressed state of tube portion 32L), the controller 52, knowing the position of the compression member 38 at all times, controls the driver 46 to purge the milk currently held in the large tube portion 32L, by driving the compression member 38 to its opposite position limit (where it compresses the large tube portion 32L the most). This reestablishes, or resets the compression member, so that it again can establish the maximum suction level without nearing its position limit. This process is repeated each time the compression member 38 comes within a predetermined distance from its position limit.

FIG. 47 illustrates events that may be carried out by the system 100 during an extraction mode of pumping milk from a breast. At event 4702, after latch and let down of milk have been achieved, the system begins operating in extraction mode. In extraction mode, the system cycles between latch suction (e.g., about 55 mmHg, or a value preselected from the range of about 25 mmHg to about 80 mmHg suction) and maximum suction (e.g., about 150 mmHg, or a value preselected from the range of about 130 mmHg to about 200 mmHg suction). The pumping cycle may be a regular, continuous cycle, or may be pre-programmed to provide some irregularity, such as occasional pauses in pumping action to simulate when a breastfeeding baby pauses to take a break before resuming suckling. The cycle speed of the pumping action is predetermined in the embodiment, such as 60 cycles per minute, or some other predetermined rate. Optionally, the operator may be able to set or adjust the cycle speed to be used when initiating the extraction mode and/or at any time during operation in extraction mode. The controller 52 monitors the pressure waves within the system 100 at event 4704 and the motion of the compression member 38. If there has been no expression of milk, the pressure wave profile and the motion of the compression member 38 are fairly consistent, with little or no changes in end points of the travel of the compression member. As milk enters the system, the controller will need to move the compression member further to achieve the same target maximum vacuum level and this change in the pressure versus compression member 38 position relationship is identified by the controller as an indicator that milk has entered the tubing 32. When substantially no change in the pressure versus compression member 38 position has occurred, pumping continues with the current pumping cycle parameters as to speed and movement of the compression member 38. When the pressure versus compression member 38 position changes, such as due to milk entering the system, the controller 52 at event 4704 identifies the change in the relationship between compression member 38 position and vacuum pressure achieved, via feedback from sensor 54 and monitoring of the motor, gear train and/or compression member positions, and adjusts the speed, travel range and/or position of compression member 38 at event 4708 in an effort to maintain the desired pressure profile, cycling between latch vacuum and maximum vacuum levels. If no pressure/position relationship change (within a predetermined minimal range) is sensed at 4704, then the system continues pumping with the current cycle control parameters at event 4706.

At event 4710 the controller checks to determine whether the outward position limit of the compression member 38 has been reached during the attempt to maintain the system operating according to the predetermined pressure profile. If the position limit has been reached, then the controller 52 at event 4712 controls the system to perform a purge procedure by reducing the pressure to latch pressure; sealing off tubing portion 32S by compressing it with compression member 36, and operating driver 46 to drive the compression member 38 inwardly against the tube portion 32L to the other position limit to purge the milk from the tube portion 32L and then processing proceeds to event 4714. If the position limit has not been reached at event 4710 then processing proceeds directly to event 4714. At event 4714 the pressure is again checked to see if predetermined pressure parameters have been achieved. If the pressure profile has been returned to target (the predetermined pressure profile) then the controller checks to see whether processing should continue at event 4716. Optionally, event 4716 can be omitted and the extraction mode can be ended manually by the operator. Even when event 4716 is adopted, the user can manually stop the extraction mode at any time by actuating a manual switch on control panel 166. Extraction mode pumping may automatically end after a predetermined time period, or when some other event has been achieved. For example, flow of milk can be calculated based upon the pressure change calculations made by the controller, and total volume of milk extracted can also be calculated. Accordingly, extraction mode pumping can be ended after a predetermined volume of milk has been pumped, for example, or when the controller 52 estimates that the milk flow has diminished below a predetermined flow rate for a determined amount of time. Further alternatively, the system 100 can be automatically shut down after the controller 52 determines that a predetermined time period (e.g., one minute or some other predetermined time period) has elapsed during which there has been zero flow of milk. Further alternatively, the system can be automatically shut down after the controller 52 has determined that a combination of events have occurred, e.g., after five minutes if flow is at zero for at least one minute, or some other predetermined combined logic.

If extraction mode is to continue at event 4716, the processing proceeds to event 4704. If extraction mode is to end, then the process ends at event 4718. If the predetermined pressure profile has not been achieved at event 4714, the processing proceeds to event 4708.

A build supply mode can be programmed into the system that can be used by the user to help increase milk production. Using characteristics of the system 100, when in build supply mode, with a milk extraction volume goal having been set, the system 100 will conduct the pumping session including the extraction mode as usual, but once the historical volume has been achieved, the system 100 will continue pumping with pumping characteristics that simulate a hungry, growing baby such as increasing the maximum suction and holding that level for slightly longer during a pumping cycle to simulate a baby trying to draw more milk out of the breast 2, before shutting down.

In another embodiment, the predetermined pumping cycle speed of the system 100 in extraction mode can automatically increase according to the age of the user's baby. It has been found that the sucking frequency of a newborn infant is slower than that of the same baby at six months old, for example. By tracking the age of the user's baby, the controller 52 can automatically scale the increase of the predetermined pumping cycle speed to the age of the user's baby. Thus, for example, when using the system 100 when the user's baby is a newborn, the cycle speed might be 60 CPM (cycles per minute), and might be 65 CPM when the baby is two months old, and might be 70 CPM when the baby is six months old. These numbers are only exemplary and the disclosure is not to be limited to them, as the more general concept of automatically increasing the predetermined cycling frequency based on age of the baby is what is disclosed.

If the total volume of the tubing 32 and skin contact member 10 (minus the volume occupied by the breast 2 and nipple 3) is represented as T and the volume that is displaceable by compression member is represented as P, then P should be greater than 16.2% of T for purposes of this disclosure, i.e., P/T>0.162

FIG. 48 illustrates a nipple shield 480 according to an embodiment of the present disclosure. Nipple shield 480 can be attached to the breast 2 as shown in FIG. 48 (such as by suction, reattachable adhesive, etc.) to cover the nipple 3 when the mother is breastfeeding her baby. One of more openings 482 are provided in the tip region of the nipple shield 480 to allow the baby to draw milk through the nipple shield 480. The tip portion 484 that overlies the nipple 3 and at least part of the areola 4 is made much thinner than the attachment portion 486 that surrounds the tip portion 484. For example, the nipple shield 480 may be made of a single material, such as silicone, or other biocompatible elastomer with similar elasticity properties, with the tip section being about 0.25 mm in thickness (or in the range of about 0.1 mm to about 1 mm), while the attachment portion 486 may have a thickness in the range of about 2 mm to about 5 mm. This provides the attachment portion 486 with more structural support and a better retention ability on the breast 2, while the thinner tip portion 484 can easily expand, thereby providing minimal resistance to the engorgement of the nipple 3 and areola 4, so as not to restrict the milk flow from the breast.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g. amounts, forces, pressure, etc.) but some experimental errors and deviations should be accounted for.

Example 1

Testing was done on a light body vinylpolysiloxane breast flange (Danville Star VPS #80011-01 (manufactured by Danville Materials in Ramon, Calif.), to determine the relationship between force applied to the nipple receiving portion 494 and pressure (vacuum) within the nipple receiving portion 494. The nipple receiving portion 494 was immobilized by a support 496 and a predetermined force was applied by a load cell 490 (see FIG. 49 to the nipple receiving portion 494 opposite the supported side of the nipple receiving portion 494. A stopper 498 was used to allow establishment of a vacuum within the nipple receiving portion 494 and a tube 502 was used to connect syringe 504 and pressure gauge 506 in fluid communication with the interior space of the nipple receiving portion 494. Various runs were made with different preload forces applied to the nipple receiving portion 494 by load cell 490, ranging from 1.5N to 4N, which corresponded to preload displacements (at atmospheric pressure) of the wall of the nipple receiving portion ranging from −1.41 mm to −11.60 mm, see FIG. 50. The pressure changes in the nipple receiving portion 494 generated by withdrawing the plunger of syringe 504 were measured by pressure gauge 506 and recorded and plotted relative to the forces on the nipple receiving portion measured by the load cell 490.

Figure 50:
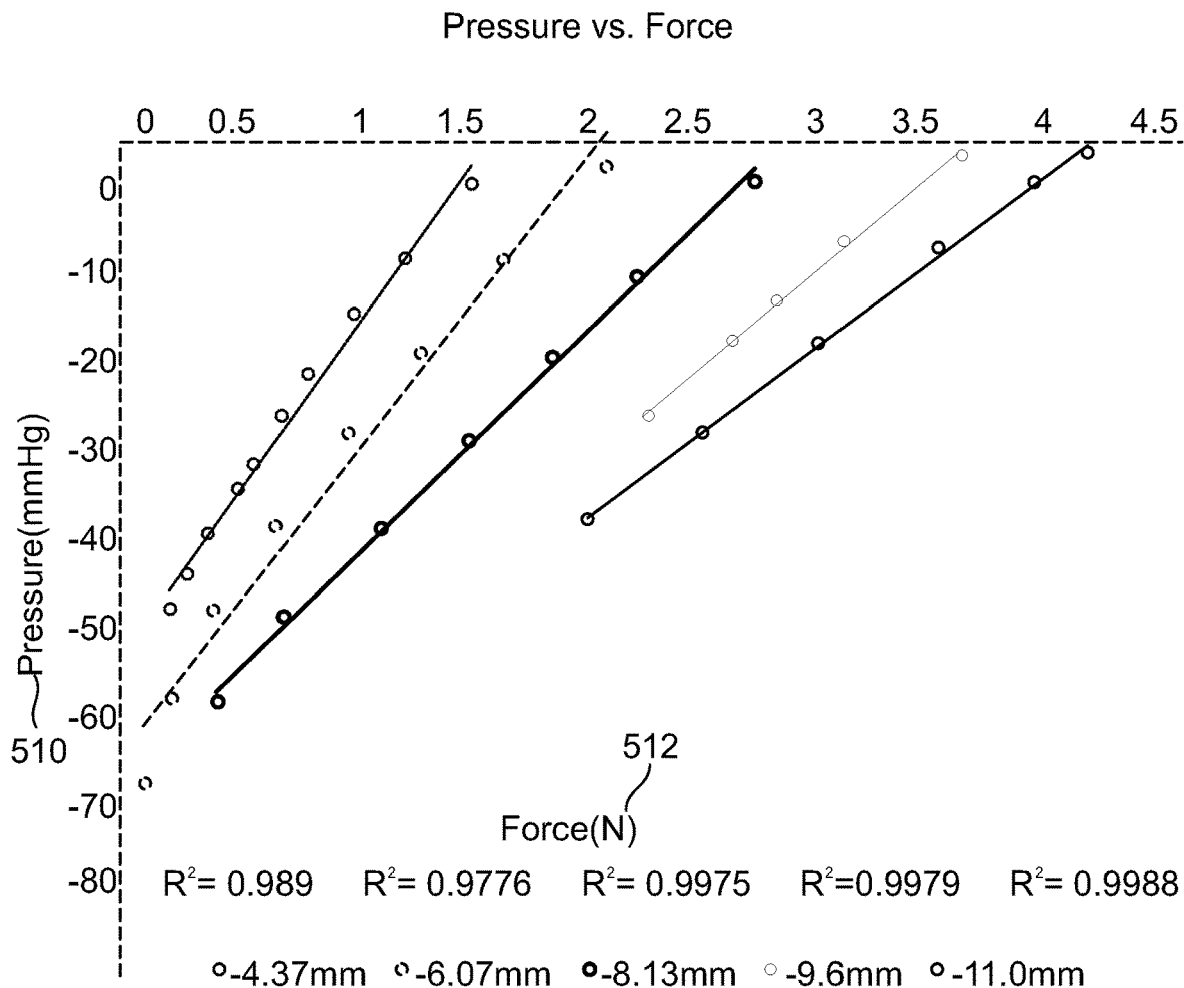
FIG. 50 illustrates results from the testing apparatus used in the testing described with regard to FIG. 49.

FIG. 50 shows the plotted results, with the recorded data points interconnected by best fit lines to show that the data shows a substantially linear relationship between pressure (vacuum) 510 within the nipple receiving portion 494 and force 512 measure on the external surface of the nipple receiving portion 494. As the vacuum increased (pressure decreased), the force exerted by the nipple receiving portion on the load cell sensor 490 decreased according to a linear force-pressure relationship.

Example 2

Figure 53:
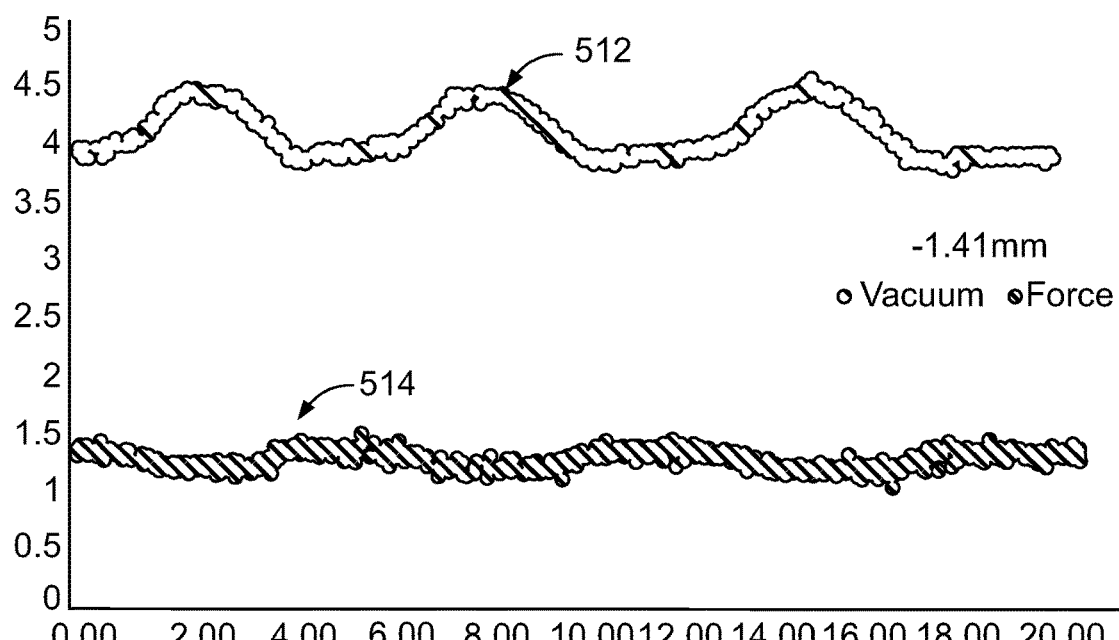
FIG. 53 illustrates results from the testing apparatus used in the testing described with regard to FIG. 51.
Figure 51:
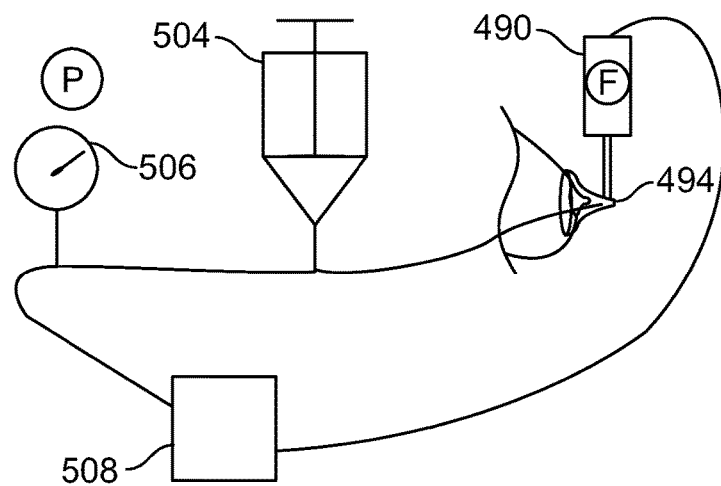
FIG. 51 schematically illustrates modified apparatus used to test the dynamic force-pressure relationship of a system, according to an embodiment of the present disclosure.
Figure 52:
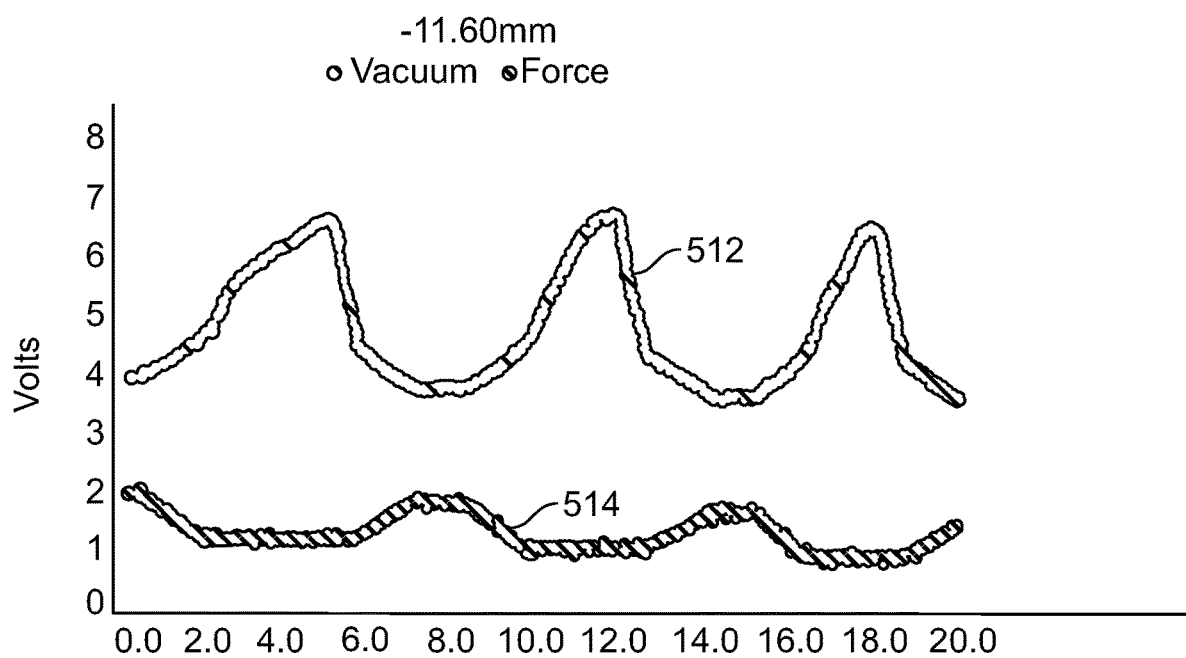
FIG. 52 illustrates results from the testing apparatus used in the testing described with regard to FIG. 51.

The arrangement of Example 1 was modified to test the dynamic force-pressure relationship of the system. An oscilloscope 508 (see FIG. 51) was electrically connected to receive output pressure reading and force readings from pressure gauge 506 and load cell/sensor 490 respectively. Like Example 1, preload displacements at atmospheric pressure were varied for different runs of the test, ranging from −11.60 mm to −1.41 mm. For each run, the vacuum was cycled between high vacuum to low vacuum three times. For each run, the force exerted by the nipple receiving portion on the sensor of load cell 490 was observed to decrease as the vacuum increased, according to a substantially linear force-pressure relationship. FIG. 52 shows a plot of vacuum 512 and force 514 plotted as voltage received by the oscilloscope 508 versus time, for the run with the preload displacement of −11.60 mm. It can be observed that the force 514 decreases linearly proportionally to the increase in vacuum 512 and vice versa. The same can be observed in FIG. 53, which plots vacuum 512 and force 514 as voltage received by the oscilloscope 508 versus time, for the run with the preload displacement of −1.41 mm. Similar results were observed for additional runs having initial displacements of −10.47 mm, −8.50 mm, −7.47 mm, −6.22 mm, −5.65 mm, −3.54 mm, −4.69 mm and −2.44 mm, respectively.

Example 3

Figure 54:
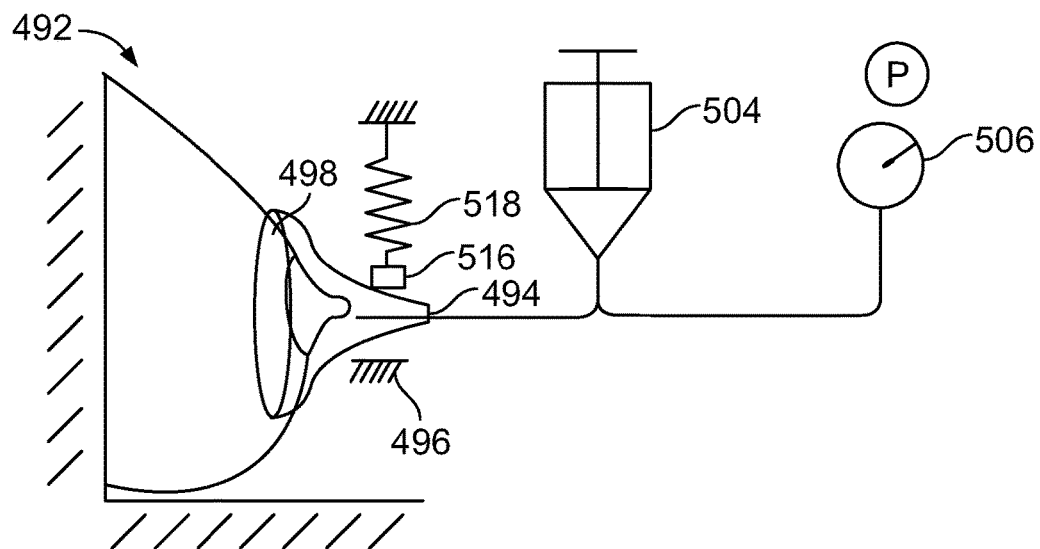
FIG. 54 schematically illustrates apparatus used to test the relationship between the position of a target location of a nipple receiving portion and vacuum level within the nipple receiving portion, according to an embodiment of the present disclosure.

The arrangement of Example 1 was modified to test the relationship between the position of a target location of the nipple receiving portion 494 and vacuum level within the nipple receiving portion 494, see FIG. 54. In this Example, the load cell 490 of Example 1 was replaced by a marker block 516 preloaded against the nipple receiving portion 494 with a spring 518 at atmospheric pressure. Upon pulling a vacuum in the system by withdrawing the plunger of the syringe 504, the marker block 516 moves with the wall of the nipple receiving portion 494 as it flexed inwardly due to the reduction in pressure.

Example 4

Figure 55:
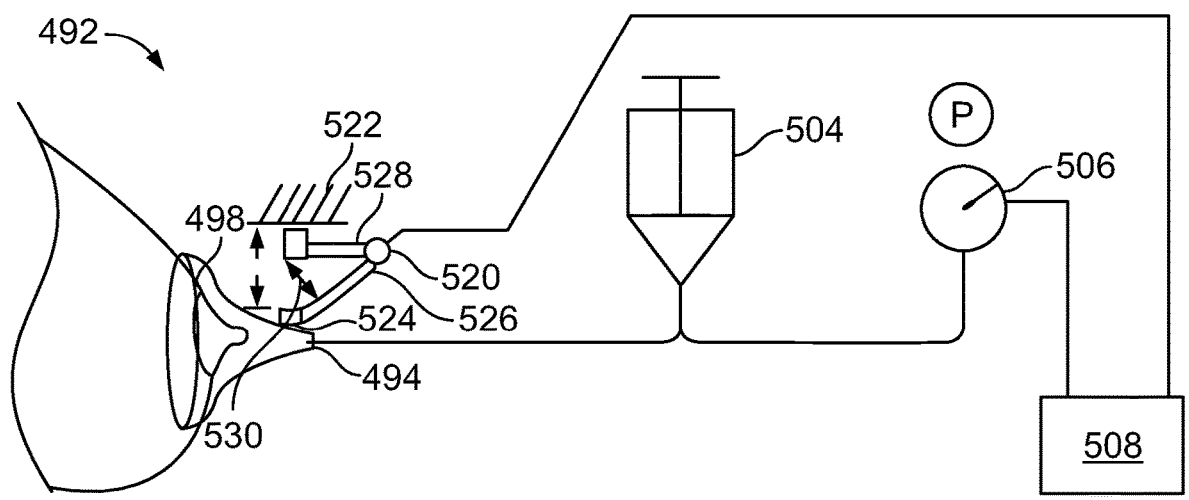
FIG. 55 schematically illustrates apparatus used to test the relationship between the position of a target location of a nipple receiving portion and vacuum level within the nipple receiving portion, according to an embodiment of the present disclosure.

The arrangement of Example 1 was modified to test the relationship between the position of a target location of the nipple receiving portion 494 and vacuum level within the nipple receiving portion 494, see FIG. 55. In this Example, the load cell 490 of Example 1 was replaced by a first and second marker block 522, 524, connected by arms to a potentiometer 520, with the first marker block 522 being fixed to a stationary reference location and the second marker block 524 being fixed to the nipple receiving portion 494 and thus movable directly with movements of the nipple receiving portion. The second marker 524 was preloaded against the nipple receiving portion 494 at atmospheric pressure. Upon pulling a vacuum in the system by withdrawing the plunger of the syringe 504, the marker block 524 moves with the wall of the nipple receiving portion 494, relative to the fixed marker block 522, as the nipple receiving portion 494 is flexed inwardly due to the reduction in pressure. The movement of marker 524 angularly moves the arm 526 relative to arm 528 and this angular movement was registered by the potentiometer and sent to oscilloscope 508. The change in angle 530 was measured by the potentiometer, and the linear change in the distance 532 between the position of marker 524 and marker 522, can be calculated by a difference in the original distance 532 and the distance corresponding to the angle calculated from the angle change measured, relative to the original angle.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure.

That which is claimed is:

1. An automatic breast pump system, comprising:
    a flange sized and shaped to receive and surround a user's nipple;
    an external shell shaped to provide a natural breast profile, the external shell sized and shaped to be received within a bra of a user;
    a pump mechanism configured to provide a suction pressure within the flange, the pump mechanism configured within the external shell;
    a controller associated with the pump mechanism and configured to control pump function, the controller configured within the external shell; and
    a conduit for transporting milk pumped from a breast, the conduit configured within the external shell;
    wherein the controller is responsive to a milk flow within the conduit and provides automatic, real time adjustments to maintain a target pressure within the conduit of the breast pump system in response to the milk flow in the conduit.

2. The breast pump system of claim 1, wherein the controller repeatedly measures and calculates pressure to vary suction pressure.

3. The breast pump system of claim 1, wherein the controller continuously measures and calculates pressure to vary suction pressure.

4. The breast pump system of claim 1, further comprising a sensor in communication with the controller to provide a control loop that is used to adjust suction pressure.

5. The breast pump system of claim 4, further comprising a compression member that creates the suction pressure, wherein the control loop is used to adjust a position of the compression member to vary or maintain suction pressure.

6. The breast pump system of claim 5, further comprising a second compression member, wherein the control loop is used to adjust a position of the second compression member to vary or maintain suction pressure.

7. The breast pump system of claim 4, further comprising a compression member that creates the suction pressure, wherein the control loop is used to adjust a speed of the compression member to vary or maintain suction pressure.

8. The breast pump system of claim 7, further comprising a second compression member, wherein the control loop is used to adjust a speed of the second compression member to vary or maintain suction pressure.

9. The breast pump system of claim 4, wherein a volume of milk pumped is calculated by assessing the position of the compression member.

10. The breast pump system of claim 9, wherein pressure changes are assessed by a comparison with positions of the compression member.

11. The breast pump system of claim 1, wherein a volume of milk pumped is calculated by comparing pressure changes.

12. The breast pump system of claim 1, further comprising at least one compression member that engages the conduit.

13. The breast pump system of claim 1, further comprising a sensor used to provide feedback to the controller for controlling pumping cycles to achieve or maintain desired suction pressure.

14. The breast pump system of claim 13, wherein the sensor is a flow sensor.

15. The breast pump system of claim 13, wherein the sensor is a non-contact sensor.

16. The breast pump system of claim 13, wherein the sensor is a pressure sensor.

17. The breast pump system of claim 13, wherein a volume of milk produced during pumping is calculated.

18. The breast pump system of claim 13, wherein flow-rate at any particular time in a pumping session is calculated.

* * * * *